United States Patent [19]

Hanagan et al.

[11] Patent Number: 4,948,419

[45] Date of Patent: * Aug. 14, 1990

[54] HERBICIDAL PYRIDINE SULFONAMIDES

[75] Inventors: Mary A. Hanagan, Newark; Barry A. Wexler, Wilmington, both of Del.

[73] Assignee: E. I. du Pont de Nemours and Company, Wilmington, Del.

[ * ] Notice: The portion of the term of this patent subsequent to Feb. 13, 2007 has been disclaimed.

[21] Appl. No.: 310,385

[22] Filed: Feb. 15, 1989

Related U.S. Application Data

[60] Division of Ser. No. 94,701, Sep. 14, 1987, Pat. No. 4,838,926, which is a continuation-in-part of Ser. No. 943,137, Dec. 18, 1986, abandoned.

[51] Int. Cl.$^5$ ............... A01N 43/66; A01N 43/68; C07D 401/12; C07D 401/14

[52] U.S. Cl. .................................... 71/93; 71/86; 71/87; 71/90; 544/212; 544/207; 544/209; 544/198; 544/113; 544/195; 544/83; 544/219; 544/214

[58] Field of Search .............. 71/93, 86, 87, 90; 544/212, 207, 209, 198, 113, 195, 83, 219, 214

[56] References Cited

U.S. PATENT DOCUMENTS

| | | | |
|---|---|---|---|
| 4,339,267 | 7/1982 | Levitt | 71/92 |
| 4,342,587 | 8/1982 | Levitt | 71/92 |
| 4,348,220 | 9/1982 | Schwing | 71/92 |
| 4,421,550 | 12/1983 | Selby et al. | 71/92 |
| 4,456,469 | 6/1984 | Adams, Jr. | 71/93 |
| 4,487,626 | 12/1984 | Zimmerman | 71/90 |
| 4,496,392 | 1/1985 | Levitt | 71/93 |
| 4,544,401 | 10/1985 | Levitt | 71/92 |
| 4,662,933 | 5/1987 | Thompson | 71/92 |
| 4,740,229 | 4/1988 | Selby | 71/90 |
| 4,778,512 | 10/1988 | Wexler | 71/92 |
| 4,789,465 | 12/1988 | Barnette et al. | 71/90 |

FOREIGN PATENT DOCUMENTS

| | | |
|---|---|---|
| 24259 | 9/1984 | Australia . |
| 13480 | 7/1980 | European Pat. Off. . |
| 84224 | 7/1983 | European Pat. Off. . |
| 117014 | 8/1984 | European Pat. Off. . |
| 125864 | 11/1984 | European Pat. Off. . |
| 155767 | 9/1985 | European Pat. Off. . |
| 161905 | 11/1985 | European Pat. Off. . |
| 164269 | 12/1985 | European Pat. Off. . |
| 171286 | 2/1986 | European Pat. Off. . |
| 187489 | 7/1986 | European Pat. Off. . |
| 111982 | 5/1987 | Japan . |

*Primary Examiner*—John M. Ford

[57] ABSTRACT

This invention relates to certain novel pyridine sulfonamide compounds, to compositions containing such compounds, and to a method of use of such compositions to control the growth of undesired vegetation.

36 Claims, No Drawings

HERBICIDAL PYRIDINE SULFONAMIDES

RELATED APPLICATIONS

This application is a division of application U.S. Ser. No. 07/094,701 filed Sept. 14, 1987, now U.S. Pat. No. 4,838,926, which is a continuation-in-part of U.S. Ser. No. 943,137 filed Dec. 18, 1986, now abandoned.

TECHNICAL FIELD

This invention relates to certain novel pyridine sulfonamide compounds, to compositions containing such compounds, and to a method of use of such compositions to control the growth of undesired vegetation.

BACKGROUND OF THE INVENTION

The present of undesired vegetation causes substantial damage to agricultural products which helps satisfy man's basic food and fiber needs. The current population explosion and concomitant world food and fiber shortage demand improved productivity in agricultural efforts since virtually all the readily available, relatively fertile cropland in developed countries has already been placed in use [Science, 214, 1087, 1089 (1981)]. Preventing or minimizing loss of a portion of such valuable crops, by inhibiting the growth or killing undesired competing vegetation which is potentially most damaging to crop yields [Science 215, 134 (1982)], is a significant approach to improving agricultural efficiency.

A wide variety of materials, commonly referred to as herbicides, useful for controlling the growth of undesired vegetation (by killing or inhibiting) is available. There still exists a need, however, for effective herbicides which destroy or control weeds while not significantly damaging useful crops. Efficient production on large acreage requires the extensive use of herbicides used by American farmers in 1981 [Chemical Weed, July 7, 1982, p. 36]. At the present time, no existing product provides all features deemed advantageous. Greater persistence, less soil residual, reduced application rates, reduced soil binding, greater selectivity or safety margin between weed control and crop injury, and less dependence on rainfall for activation are currently desirable features for herbicides.

EP-A-No. 13,480 published July 23, 1980, discloses herbicidal sulfonamides of the formula

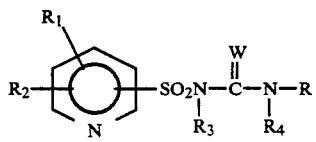

wherein $R_1$ is H, Cl, Br, F, $C_1$–$C_4$ alkyl, $C_1$–$C_4$ alkoxy, $C_1$–$C_4$ alkylthio, $NO_2$ or $CO_2R_5$.

U.S. Pat. No. 4,339,267 discloses herbicidal sulfonamides of the formula

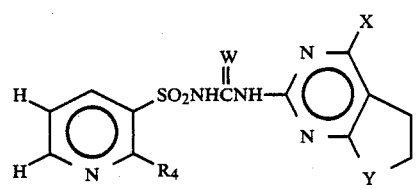

wherein $R_4$ is H, Cl, Br, F, $C_1$–$C_4$ alkyl, $C_1$–$C_4$ alkoxy, $NO_2$, $CO_2R_6$ or $SR_{13}$.

U.S. Pat. No. 4,342,587 discloses herbicidal sulfonamides of the formula

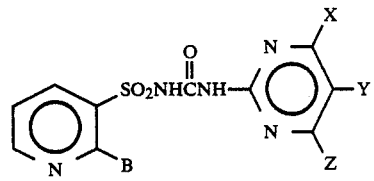

wherein B is Cl or Br.

U.S. Pat. No. 4,456,469 discloses herbicidal sulfonamides of the formula

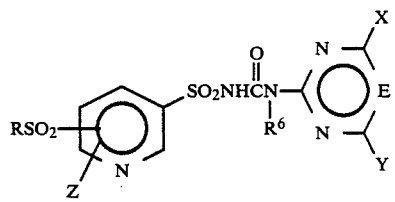

wherein
R is $C_1$–$C_6$ alkyl, $C_3$–$C_6$ alkenyl, $C_2$–$C_4$ alkoxyalkyl, $C_5$–$C_6$ cycloalkyl, $R'OCH_2CH_2OCH_2$, $R'OCH_2CH_2OCH_2CH_2$,

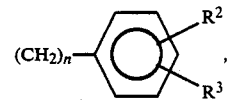

$CF_3$, $CF_3CH_2$, $HGLCCF_2$ or $HCF_2$; and
Z is H, F, Cl, Br, $CH_3$, $OCH_3$ or $SCH_3$.

U.S. Pat. No. 4,487,626 discloses herbicidal sulfonamides of the formula

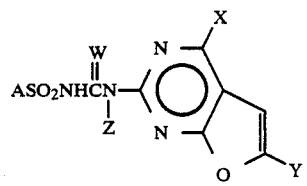

wherein
A is

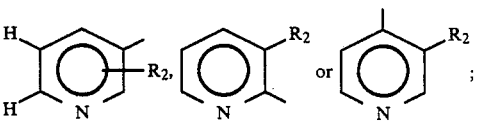

and
$R_2$ is H, F, Cl, Br, $C_1$–$C_4$ alkyl, $C_1$–$C_4$ alkoxy, $NO_2$, $CO_2R_{15}$, $S(O)_mR_{16}$, $SO_2NR_{18}R_{19}$ or $SO_2N(OCH_3)CH_3$.

U.S. Pat. No. 4,421,550 discloses herbicidal sulfonamides of the formula

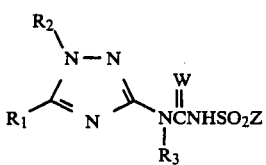

wherein
Z is

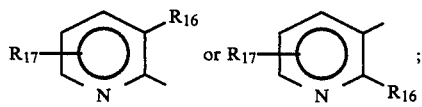

and
R$_{16}$ is H, C$_1$-C$_4$ alkyl, C$_1$-C$_4$ alkoxy, F, Cl, Br, CF$_3$, CO$_2$R$_{20}$, SO$_2$NR$_{10}$R$_{11}$, SO$_2$N(OCH$_3$)CH$_3$ or S(O)$_n$R$_{13}$.

U.S. Pat. No. 4,496,392 discloses herbicidal sulfonamides of the formula

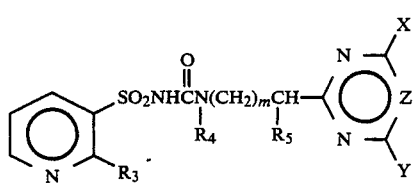

wherein R is Cl, SO$_2$CH$_3$ or SO$_2$N(CH$_3$)$_2$.

EP-A-No. 84,224, published July 27, 1983, discloses herbicidal sulfonamides of the formula

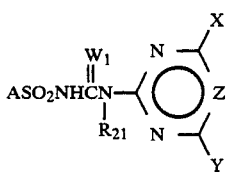

wherein
A is

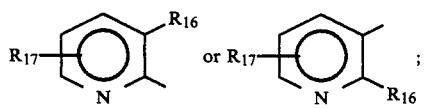

and
R$_{16}$ is H, C$_1$-C$_4$ alkyl, C$_1$-C$_4$ alkoxy, F, Cl, Br, CF$_3$, CO$_2$R$_9$, SO$_2$NR$_{10}$R$_{11}$, SO$_2$N(OCH$_3$)CH$_3$ or S(O)$_n$R$_{13}$.

EP-A-No. 125,846, published Nov. 21, 1984, discloses herbicidal sulfonamides of the formula

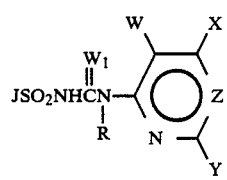

wherein
J is

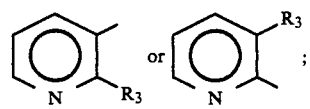

and
R$_3$ is Cl, SO$_2$CH$_3$, SO$_2$N(CH$_3$)$_2$, OCH$_3$, NO$_2$ or N(CH$_3$)$_2$.

EP-A-No. 155,767, published Sept. 25, 1985, discloses herbicidal sulfonamides of the formula

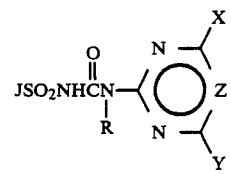

wherein
J is

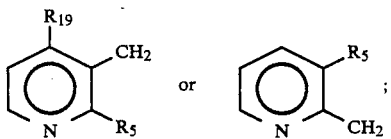

and
R$_5$ is H, CH$_3$, Cl, Br, CO$_2$R$_{15}$, C(O)NR$_{16}$R$_{17}$, SO$_2$NR$_{16}$R$_{17}$, SO$_2$N(OCH$_3$)CH$_3$, SO$_2$R$_{18}$ or NO$_2$.

EP-A-No. 161,905, published Nov. 21, 1985, discloses herbicidal sulfonamides of the formula

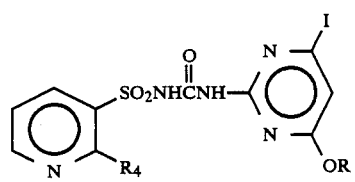

wherein R$_4$ is CH$_3$, CH$_2$CH$_3$, OCH$_3$, OCH$_2$CH$_3$, F, Cl, Br, SO$_2$NR$_{16}$R$_{17}$, SO$_2$N(OCH$_3$)CH$_3$, S(O)$_n$R$_{19}$, C$_3$-C$_4$ alkenyloxy or C$_3$-C$_4$ alkynyloxy.

EP-A-No. 164,269, published Dec. 11, 1985, discloses herbicidal sulfonamides of the formula

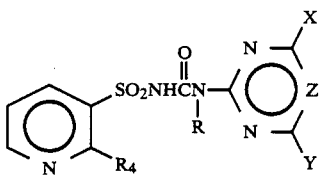

wherein R$_4$ is CH$_3$, CH$_2$CH$_3$, OCH$_3$, OCH$_2$CH$_3$, F, Cl, Br, SO$_2$NR$_{11}$R$_{12}$, SO$_2$N(OCH$_3$)CH$_3$ or S(O)$_n$R$_{13}$.

EP-A-No. 171,286, published Feb. 12, 1986, discloses herbicidal sulfonamides of the formula

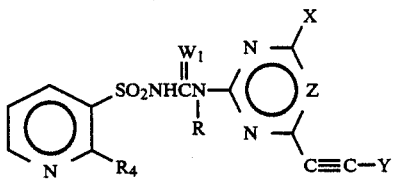

wherein $R_4$ is $CH_3$, $CH_2CH_3$, $OCH_3$, $OCH_2CH_3$, F, Cl, Br, $SO_2NR_{18}R_{19}$, $SO_2N(OCH_3)CH_3$, $S(O)_nR_{21}$, $C_3$-$C_4$ alkenyloxy, $CH_2OCH_3$ or $CH_2OCH_2CH_3$.

EP-A-No. 187,489, published July 16, 1986, discloses herbicidal sulfonamides of the formula

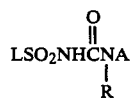

wherein
L is

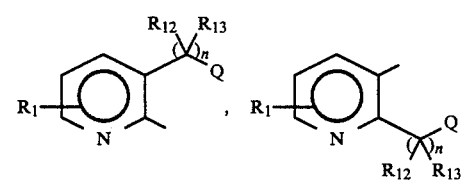

Q is an optionally substituted 3- or 4-membered ring; and
W is substituted alkenyl or alkynyl.

AU-A-No. 24259/84, published Sept. 6, 1984, discloses herbicidal guanidines of the formula

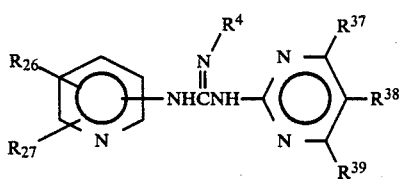

wherein $R_{26}$ and $R_{27}$ are independently H, F, Cl, Br, $NO_2$, CN, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, di-($C_1$-$C_4$ alkyl)aminosulfonyl or $C_1$-$C_4$ alkoxy carbonyl.

EP-A-No. 117,014, published Aug. 29, 1984, discloses herbicidal quanidines of the formula

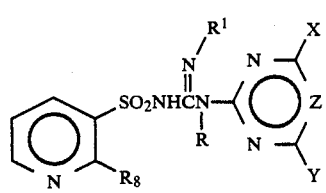

wherein $R_8$ is $CH_3$, $CH_2CH_3$, $OCH_3$, $OCH_2CH_3$, F, Cl, Br, $SO_2NR_{20}R_{21}$, $SO_2N(OCH_3)CH_3$ or $S(O)_nR_{23}$.

JAP No. 62-111,982, published May 22, 1987, discloses herbicidal pyridine sulfonylureas containing a ortho-$CH_2OR_1$ group, wherein $R_1$ is $C_1$-$C_4$ alkyl or $C_1$-$C_4$ haloalkyl.

SUMMARY OF THE INVENTION

The novel pyridine sulfonamide compounds of the present invention are highly active as preemergent and/or postemergent herbicides or plant growth regulants. Specifically, one aspect of the invention relates to compounds having the formula I:

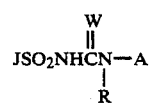

wherein
J is

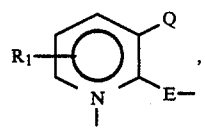 , 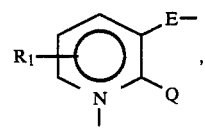 ,

J-1      J-2

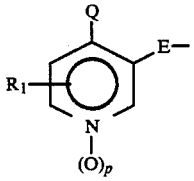 or 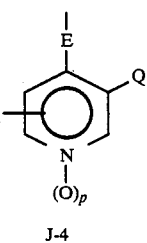 ;

J-3      J-4

R is H or $CH_3$;
E is a single bond or $CH_2$;
W is O, S or $NR_x$;
p is 0 or 1;
$R_x$ is H, OH, $C_1$-$C_3$ alkyl, $C_1$-$C_3$ haloalkyl, $C_1$-$C_3$ alkoxy, $C_1$-$C_3$ haloalkoxy, allyloxy, propargyloxy or $NR_xR_z$;
$R_y$ is H or $C_1$-$C_3$ alkyl;
$R_z$ is $C_1$-$C_3$ alkyl;
$R_1$ is H, $C_1$-$C_3$ alkyl, $C_1$-$C_3$ haloalkyl, halogen, nitro, $C_1$-$C_3$ alkoxy, $SO_2NR_aR_b$, $C_1$-$C_3$ alkylthio, $C_1$-$C_3$ alkylsulfinyl, $C_1$-$C_3$ alkylsulfanyl, CN, $CO_2R_c$, $C_1$-$C_3$ haloalkoxy, $C_1$-$C_3$ haloalkylthio, amino, $C_1$-$C_2$ alkylamino, di($C_1$-$C_3$ alkyl)amino, L or $C(O)NR_dR_e$;
$R_a$ is H, $C_1$-$C_4$ alkyl, $C_2$-$C_3$ cyanoalkyl, methoxy or ethoxy;
$R_b$ is H, $C_1$-$C_4$ alkyl or $C_3$-$C_4$ alkenyl; or
$R_a$ and $R_b$ may be taken together as —$(CH_2)_3$, —$(CH_2)_4$—, —$(CH_2)_5$— or —$CH_2CH_2OCH_2CH_2$—;
$R_c$ is $C_1$-$C_4$ alkyl, $C_3$-$C_4$ alkenyl, $C_3$-$C_3$ alkynyl, $C_2$-$C_4$ haloalkyl, $C_1$-$C_2$ cyanoalkyl, $C_5$-$C_6$ cycloalkyl, $C_4$-$C_7$ cycloalkylalkyl or $C_2$-$C_4$ alkoxyalkyl;
$R_d$ is H or $C_1$-$C_3$ alkyl;
$R_e$ is $C_1$-$C_3$ alkyl;
L is

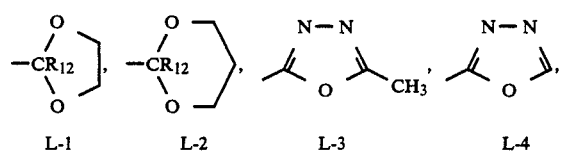

L-1, L-2, L-3, L-4

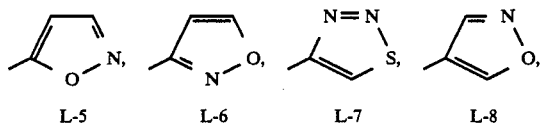

L-5, L-6, L-7, L-8

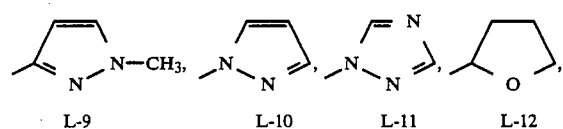

L-9, L-10, L-11, L-12

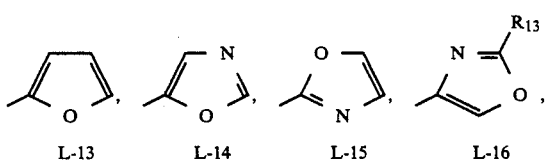

L-13, L-14, L-15, L-16

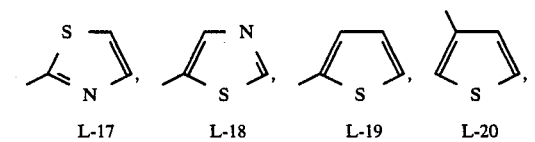

L-17, L-18, L-19, L-20

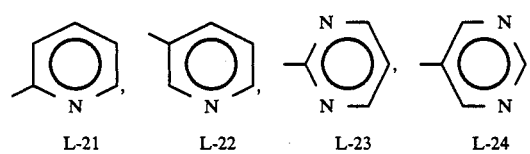

L-21, L-22, L-23, L-24 or

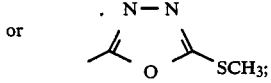

L-25

Q is $C_1$–$C_4$ alkyl substituted with $R_2$;
$R_2$ is $OR_3$, $S(O)_n R_4$, $CO_2 R_4'$, $CONR_5 R_6$,

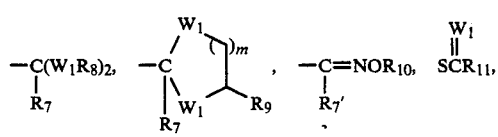

CN, $NO_2$, $\overset{O}{\underset{\|}{P}}R_{14}R_{15}$ or $\overset{S}{\underset{\|}{P}}R_{14}R_{15}$;

$R_3$ is H, $C_1$–$C_4$ alkyl, $C_3$–$C_4$ alkenyl, $C_3$–$C_4$ alkynyl, $C_1$–$C_4$ haloalkyl, $C_3$–$C_4$ haloalkenyl, $C_3$–$C_4$ haloalkynyl, $C_2$–$C_4$ alkylcarbonyl, $C_2$–$C_4$ haloalkylcarbonyl, $C_1$–$C_4$ alkylsulfonyl, $C_2$–$C_4$ alkoxyalkyl, $C_2$–$C_4$ alkylthioalkyl or $C_2$–$C_4$ cyanoalkyl;

$R_4$ is $C_1$–$C_4$ alkyl, $C_3$–$C_4$ alkenyl, $C_3$–$C_4$ alkynyl, $C_1$–$C_4$ haloalkyl, $C_3$–$C_4$ haloalkenyl, $C_3$–$C_4$ haloalkynyl, $C_2$–$C_4$ alkoxyalkyl, $C_2$–$C_4$ alkylthioalkyl or $C_2$–$C_4$ cyanoalkyl;

$R_4'$ is $C_1$–$C_4$ alkyl, $C_3$–$C_4$ alkenyl, $C_2$–$C_4$ haloalkyl, $C_3$–$C_4$ haloalkenyl, $C_3$–$C_4$ haloalkynyl, $C_2$–$C_4$ alkoxyalkyl, $C_2$–$C_4$ alkylthioalkyl or $C_2$–$C_4$ cyanoalkyl;

$R_5$ is H or $C_1$–$C_3$ alkyl;

$R_6$ is $C_1$–$C_4$ alkyl, $C_1$–$C_4$ haloalkyl, cyclopropyl, allyl or propargyl;

$R_5$ and $R_6$ may be taken together to form $+CH_2+_3$, $+CH_2+_4$, $+CH_2+_5$ or $-CH_2CH_2OCH_2CH_2-$;

$R_7$ is H, $C_1$–$C_4$ alkyl or $C_1$–$C_4$ haloalkyl;

$R_7'$ is H, $C_1$–$C_4$ alkyl, $C_1$–$C_4$ haloalkyl, Cl or CN;

$R_8$ is $C_1$–$C_2$ alkyl;

$R_9$ is H or $CH_3$;

$R_{10}$ is H, $C_1$–$C_4$ alkyl, $C_3$–$C_4$ alkenyl or $C_3$–$C_4$ alkynyl;

$R_{11}$ is $C_1$–$C_4$ alkyl, $C_1$–$C_4$ alkoxy, $C_1$–$C_4$ alkylthio, $C_1$–$C_4$ alkylamino or di($C_1$–$C_4$ alkyl)amino;

$W_1$ is O or S;

n is 0, 1 or 2;

m is 1 or 2;

$R_{12}$ is H or $CH_3$;

$R_{13}$ is H or $CH_3$;

$R_{14}$ and $R_{15}$ are independently $C_1$–$C_2$ alkyl, $C_1$–$C_2$ alkoxy, $C_1$–$C_2$ alkylthio, $NHCH_3$ or $N(CH_3)_2$;

A is

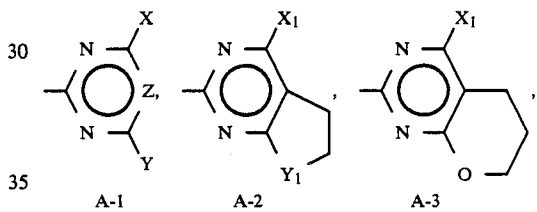

A-1, A-2, A-3

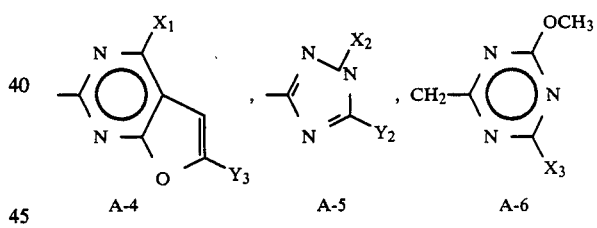

A-4, A-5, A-6 or

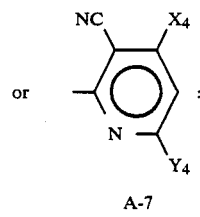

A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido, cyano,

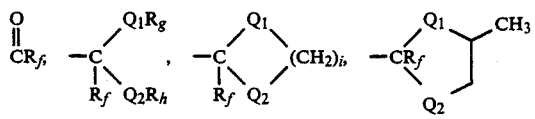

or N(OCH$_3$)CH$_3$;

i is 2 or 3;
Q$_1$ and Q$_2$ are independently O or S;
R$_f$ is H or C$_1$–C$_3$ alkyl;
R$_g$ and R$_h$ are independently C$_1$–C$_3$ alkyl;
Z is CH, N, CCH$_3$, CC$_2$H$_5$, CCl or CBr;
Y$_1$ is O or CH$_2$;
X$_1$ is CH$_3$, OCH$_3$, OC$_2$H$_5$ or OCF$_2$H;
X$_2$ is CH$_3$, C$_2$H$_5$ or CH$_2$CF$_3$;
Y$_2$ is OCH$_3$, OC$_2$H$_5$, SCH$_3$, SC$_2$H$_5$, CH$_3$ or CH$_2$CH$_3$;
X$_3$ is CH$_3$ or OCH$_3$;
Y$_3$ is H or CH$_3$;
X$_4$ is CH$_3$, OCH$_3$, OC$_2$H$_5$, CH$_2$OCH$_3$ or Cl;
Y$_4$ is CH$_3$, OCH$_3$, OC$_2$H$_5$ or Cl;
and their agriculturally suitable salts; provided that
(1) when X is halogen, then Z is CH and Y is OCH$_3$, OC$_2$H$_5$, NH$_2$, NHCH$_3$, N(CH$_3$)$_2$, OCF$_2$H, OCF$_2$Br or N(OCH$_3$)CH$_3$;
(2) when X or Y is C$_1$ haloalkoxy, then Z is CH;
(3) when W is S, then R is H, E is a single bond, A is A-1, Z is CH or N, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

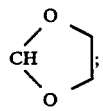

(4) when the total number of carbon atoms of X and Y is greater than four, then the combined number of carbons of R$_1$ and Q is less than or equal to six;
(5) X$_4$ and Y$_4$ are not simultaneously Cl;
(6) when Y is CN then Q is other than CH$_2$OCH$_3$ or CH$_2$OCH$_2$CH$_3$; and
(7) when Y is C$_2$–C$_4$ alkynyl then Q is other than CH$_2$OCH$_3$ or CH$_2$OCH$_2$CH$_3$;

Another aspect of this invention relates to a composition suitable for controlling the growth of undesired vegetation which comprises a herbicidally effective amount of a compound or the compounds of formula I and a diluent, surfactant, or mixture thereof. Yet another aspect of the invention relates to a method for the control of undesired vegetation which comprises applying to the locus of the undesired vegetation a herbicidally effective amount of the compounds of formula I.

Preferred compounds for reasons of increased ease of synthesis and/or greater herbicidal efficacy are:

(1) Compounds of Formula I where when J is J-1, R$_1$ is H, Q is CH$_2$OR$_3$ and both of X and Y are selected from CH$_3$, OCH$_3$, OC$_2$H$_5$ or halogen; then R$_3$ is other than C$_1$–C$_4$ alkyl or C$_1$–C$_4$ haloalkyl.

(2) Compounds of Preferred 1 where
X is C$_1$–C$_2$ alkyl, C$_1$–C$_2$ alkoxy, Cl, F, Br, I, OCF$_2$H, CH$_2$F, CF$_3$, OCH$_2$CH$_2$F, OCH$_2$CHF$_2$, OCH$_2$CF$_3$, CH$_2$Cl or CH$_2$Br; and
Y is H, C$_1$–C$_2$ alkyl, C$_1$–C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$, C(O)R$_f$,

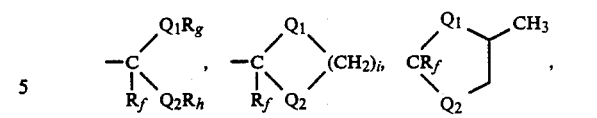

SCF$_2$H, OCF$_2$Br, cyclopropyl, C≡CH or C≡CCH$_3$; and
Z is CH or N.

(3) Compounds of Preferred 2 where
E is a single bond;
W is O.

(4) Compounds of Preferred 3 where
R$_1$ is H, CH$_3$, C$_1$ haloalkyl, halogen, NO$_2$, OCH$_3$, SO$_2$N(CH$_3$)$_2$, SCH$_3$, S(O)CH$_3$, SO$_2$CH$_3$, CO$_2$R$_c$, C$_1$ haloalkoxy, C$_1$ haloalkylthio, NH$_2$, NHCH$_3$, N(CH$_3$)$_2$, N(CH$_3$)CH$_2$CH$_3$ or CON(CH$_3$)$_2$;
R$_c$ is C$_1$–C$_3$ alkyl, allyl, propargyl, CH$_2$CH$_2$OCH$_3$ or CH$_2$CH$_2$Cl;
Q is C$_1$–C$_2$ alkyl substituted with R$_2$;
R$_2$ is OR$_3$, S(O)$_n$R$_4$, CO$_2$R$_4$', CONR$_5$R$_6$;

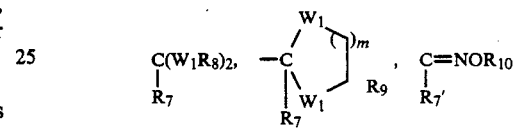

or CN;
R$_3$ is H, C$_1$–C$_2$ alkyl, allyl, propargyl, C$_1$–C$_2$ haloalkyl, C$_2$–C$_3$ alkylcarbonyl or SO$_2$CH$_3$;
R$_4$ is C$_1$–C$_2$ alkyl, allyl, propargyl, C$_1$–C$_2$ haloalkyl or C$_2$–C$_3$ alkoxycarbonyl;
R$_4$' is C$_1$–C$_2$ alkyl, allyl, propargyl, C$_2$ haloalkyl or CH$_2$CH$_2$OCH$_3$;
R$_5$ is H or CH$_3$;
R$_6$ is C$_1$–C$_2$ alkyl;
R$_7$ is H or CH$_3$;
R$_7$' is H or CH$_3$;
R$_{10}$ is CH$_3$ or CH$_2$CH$_3$; and
R$_g$ is H or CH$_3$.

(5) Compounds of Preferred 4 where J is J-1.
(6) Compounds of Preferred 4 where J is J-2.
(7) Compounds of Preferred 4 where J is J-3.
(8) Compounds of Preferred 4 where J is J-4.
(9) Compounds of Preferred 8 where
p is 0;
R is H;
A is A-1;
X is CH$_3$, OCH$_3$, OCH$_2$CH$_3$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

(10) Compounds of Preferred 5 where
p is 0;
R is H;
A is A-1;
X is CH$_3$, OCH$_3$, OCH$_2$CH$_3$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

(11) Compounds of Preferred 6 where
p is 0;
R is H;
A is A-1;
X is CH$_3$, OCH$_3$, OCH$_2$CH$_3$, Cl, OCF$_2$H or OCH$_2$CF$_3$; and Y is CH$_3$, OCH$_3$, C$_2$H$_5$, CH$_2$OCH$_3$, NHCH$_3$ or CH(OCH$_3$)$_2$.

(12) Compounds of Preferred 7 where
p is 0;
R is H;
A is A-1;
X is CH$_3$, OCH$_3$, OCH$_2$CH$_3$, Cl, OCF$_2$H or OCH$_2$CF$_3$; and
Y is CH$_3$, OCH$_3$, C$_2$H$_5$, CH$_2$OCH$_3$, NHCH$_3$ or CH(OCH$_3$)$_2$.

(13) Compounds of Formula I wherein
J is J-1;
R$_1$ is H;
Q is CH$_2$OR$_3$;
R$_3$ is C$_1$–C$_4$ alkyl or C$_1$–C$_4$ haloalkyl.

Specifically preferred for reasons of greatest ease of synthesis and/or greatest herbicidal efficacy are N-[(4,6-dimethoxypyrimidin-2-yl)aminocarbonyl]-3-(methylthiomethyl)-2-pyridinesulfonamide, m.p. 145°–147° C.; and N-[(4-chloro-6-methoxypyrimidin-2-yl)aminocarbonyl]-3-(methylthiomethyl)-2-pyridine sulfonamide, m.p. 145°–147° C.

In the above definitions, the term "alkyl", used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

Cycloalkyl denotes cyclopropyl, cyclobutyl, cyclopentyl and cyclohexyl.

The term "halogen", either alone or in compound words such as "haloalkyl", denote fluorine, chlorine, bromine or iodine. Further, when used in compound words such as "haloalkyl" said alkyl may be monohalogenated or fully substituted with halogen atoms, which may be the same or different. Examples of haloalkyl include CH$_2$CH$_2$F, CF$_2$CF$_3$ and CH$_2$CHFCl. Similarly, haloalkenyl, haloalkoxy and halothioalkyl would be said to include compounds which were monosubstituted or polysubstituted by halogen atoms, which may be the same or different.

The total number of carbon atoms in a substituent group is indicated by the C$_i$–C$_j$ prefix where i and j are numbers from 1 to 5. For example, C$_1$–C$_3$ alkylsulfonyl would designate methylsulfonyl through propylsulfonyl, C$_2$ alkoxyalkoxy would designate OCH$_2$OCH$_3$; C$_4$ alkoxyalkoxy would designate the various isomers of an alkoxy group substituted with a second alkoxy group containing a total of 4 carbon atoms, examples including OCH$_2$OCH$_2$CH$_2$CH$_3$ and OCH$_2$CH$_2$OCH$_2$CH$_3$; as a further example C$_2$ cyanoalkyl would designate CH$_2$CN and C$_3$ cyanoalkyl would designate CH$_2$CH$_2$CN and CH(CN)CH$_3$.

DETAILED DESCRIPTION OF THE INVENTION

Synthesis

Compounds of Formula I can be prepared by the methods described in Equations 1 and 2.

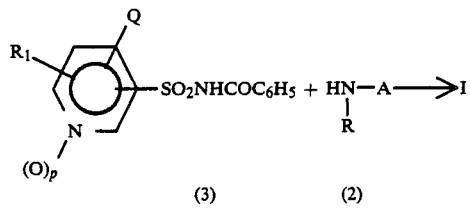

Equation 1

(3)    (2)

The reaction shown in Equation 1 is carried out by contacting the phenyl carbamate of Formula (3) with the aminoheterocycle of Formula (2) in an inert organic solvent such as dioxane or tetrahydrofuran at temperatures of about 20° to 100° C. for a period of about one-half to twenty-four hours. The product can be isolated by evaporation of the reaction solvent and purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

The phenyl carbamates of Formula (3) can be prepared by the methods described (or modifications thereof) in EPO No. 44,808 or South African Patent Application No. 825042.

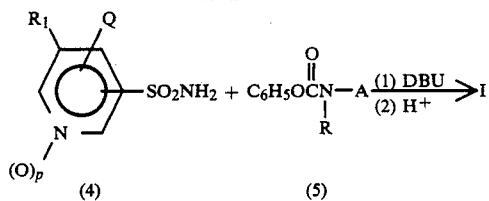

Equation 2

(4)    (5)

The reaction of Equation 2 can be carried out by contacting equimolar amounts of the sulfonamide of Formula (4) with a heterocyclic phenyl carbamate of Formula (5) in the presence of an equimolar amount of 1,8-diazabicyclo[5.4.0]undec-7-ene (DBU), by methods analogous to those described in South African Patent Application No. 830441. The phenyl carbamates of Formula (5) can be prepared by methods (or modifications thereof) described in South African Patent Application No. 825671 and South African Patent Application No. 825045.

The sulfonamide (4) can be prepared via the routes shown in Equations 3, 4 and 5 or by modifications thereof.

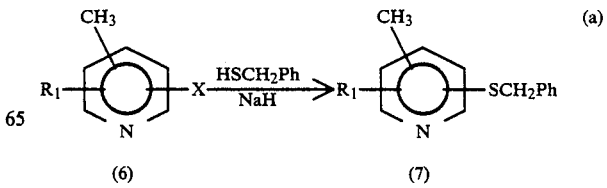

Equation 3

(a)

(6)    (7)

-continued
Equation 3

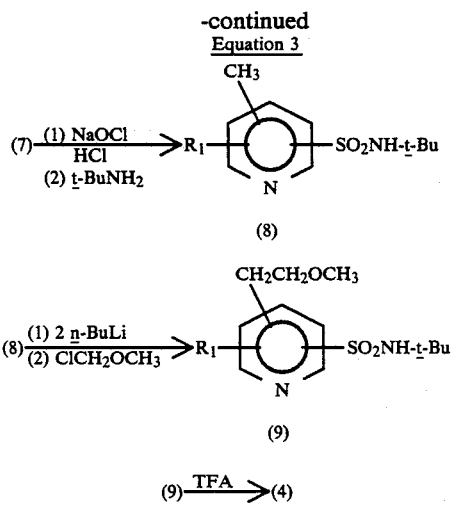

where X is F, Br, Cl.

The halopyridine (6) (*The Chemistry of Heterocyclic Compounds*, Vol. 14, Wiley-Interscience, New York (1964)) is added to a solution of sodium benzylthiolate in dimethylformamide and stirred for 12 to 24 hours. The mixture is partitioned between water and ether. The ether phase is washed with brine, dried over sodium sulfate and filtered. Evaporation of the ether leaves sulfide (7) (Equation 3a).

The compound (7) is converted to the sulfonamide (8) with hypochlorite solution as described in South African Patent Application No. 848845 (Equation 3b).

To a solution of (8) in an aprotic solvent such as tetrahydrofuran at −75° to −80° is added at least two equivalents of n-butyl lithium, the mixture is stirred at −78° for 30 to 60 minutes, followed by addition of chloromethyl methyl ether. The reaction mixture is quenched with brine, extracted with methylene chloride, dried over sodium sulfate, and concentrated to leave ether (9) (Equation 3c).

A solution of ether (9) and trifluoroacetic acid is stirred at 25° to 40° for one to two days and then concentrated to leave sulfonamide (4).

Equation 4

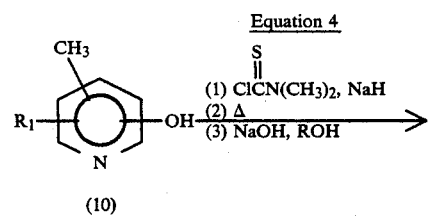

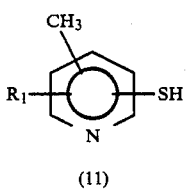

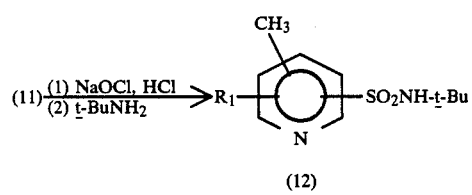

-continued
Equation 4

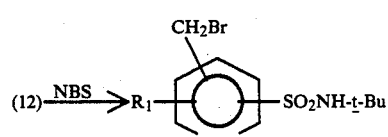

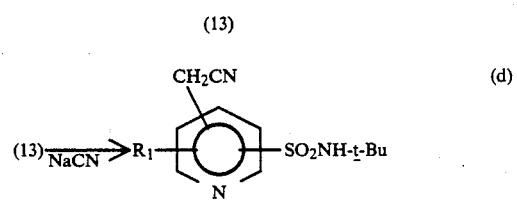

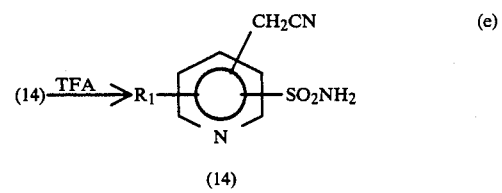

The hydroxypyridine (10) (*The Chemistry of Heterocyclic Compounds*, Vol. 14, Wiley-Interscience, New York (1964)) is converted to mercaptopyridine (11) via the thiocarbamate according to the procedure of Newman et al. in *J. Org. Chem.* 1966, 31, 3980 (Equation 4a).

Mercaptopyridine (11) is converted to sulfonamide (12) as described previously in Equation 3b (Equation 4b).

A solution of N-bromosuccinimide, benzoyl-peroxide, and sulfonamide (12) in carbon tetrachloride is refluxed for four to twenty-four hours according to the procedures of Camirez et al. (*J. Org. Chem.* 1954, 19, 183). The cooled solution is filtered and the filtrate is concentrated to leave bromide (13) (Equation 4c).

Bromide (13) is contacted with a solution of potassium cyanide in a water-methanol mixture and refluxed for 10 to 60 minutes using the procedure of Tessieri et al. in *J. Org. Chem.* 1954, 19, 711. The reaction mixture is cooled, and diluted with a saturated solution of sodium carbonate. The mixture is extracted with ether, dried over sodium sulfate and concentrated to leave cyanomethyl (14) (Equation 4d).

Compound (14) is treated with trifluoroacetic acid as described previously in Equation 3d to yield sulfonamide (4) (Equation 4e).

Equation 5

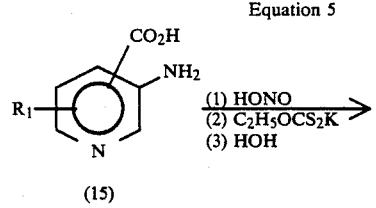

-continued
Equation 5

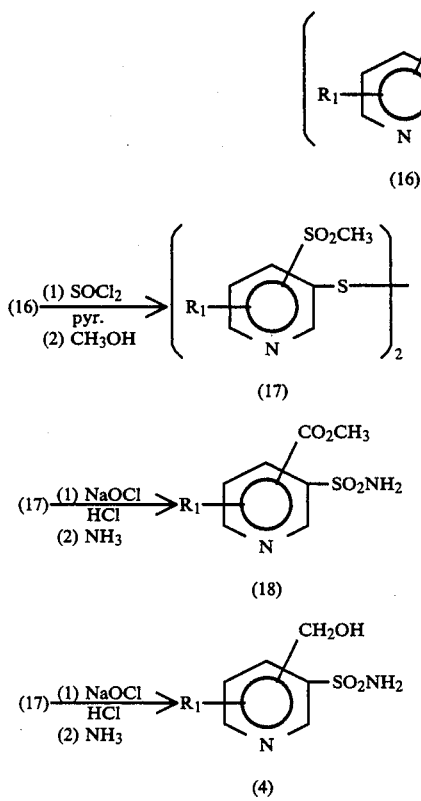

The 3-aminopyridine (15) (*The Chemistry of Heterocyclic Compounds*, Vol. 14, Wiley-Interscience, New York (1964)) is diazotized and contacted with potassium ethyl xanthate according to the procedure of Katz et al. in *J. Amer. Chem. Soc.* 1951, 73, 4925 to give disulfide (16) (Equation 5a).

Esterification of (16) using thionyl chloride, pyridine and methanol (ibid.), is followed by the oxidation of the disulfide using the procedure previously described in Equation 3b (Equation 5b and 5c).

The ester (18) is dissolved in ether and added to a solution of lithium aluminum hydride in ether. The mixture is stirred for 15 to 60 minutes and ethanol is added to decompose the excess lithium aluminum hydride. The mixture is filtered and the ether filtrate is concentrated to an oil. This oil is treated with 10% sodium hydroxide and continuously extracted with ether. The ether extracts are concentrated to leave alcohol (4).

The heterocyclic amines of Formula (2) are known compounds.

The synthesis of heterocyclic amines such as those represented by Formula 2 has been reviewed in "The Chemistry of Heterocyclic Compounds," a series published by Interscience Publ., New York and London. Aminopyrimidines are described by D. J. Brown in "The Pyrimidines," Vol. XVI of the series mentioned above which is herein incorporated by reference. The 2-amino-1,3,5-triazines of Formula 2, where A is A-1 and Z is N, can be prepared according to the methods described by E. M. Smolin and L. Rapaport in "s-Triazines and Derivatives," Vol. XIII.

Pyrimidines of Formula 2, where A is A-1 and Y is an acetal or thioacetal substituent, can be prepared by methods taught in European Patent Application No. 84,224 (published July 27, 1983).

Pyrimidines of Formula 2, where A is A-1 and Y is cyclopropyl or $OCF_2H$ can be synthesized according to the methods taught in U.S. Pat. No. 4,515,626 and U.S. Pat. No. 4,540,782, respectively.

Compounds of Formula 2, where A is A-2 or A-3, can be prepared by procedures disclosed in U.S. Pat. No. 4,339,267.

Compounds of Formula 2, where A is A-4, can be prepared by methods taught in U.S. Pat. No. 4,487,626.

Additional reference dealing with the synthesis of bicyclic pyrimidines of Formula 2, where A is A-2, A-3, or A-4 are Braker, Sheehan, Spitzmiller and Lott, *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula 2, where A is A-5, can be prepared by methods taught in U.S. Pat. No. 4,421,550.

Compounds of Formula 2, where A is A-6, can be prepared by methods taught in U.S. Pat. No. 4,496,392.

Compounds of Formula 2, where A is A-7, can be prepared by methods taught in EP-A-No. 125,864.

Agriculturally suitable salts of compounds of Formula I are also useful herbicides and can be prepared by well-known methods including those described in U.S. Pat. No. 4,127,405.

The following Example illustrates syntheses of the compounds of this invention. Temperatures are in degrees Celsius.

EXAMPLE 1

Step A. 3-Methyl-2-(phenylmethylthio)-pyridine

A suspension of 4.8 g (100 mmole) of sodium hydride in 50 mls of dimethylformamide was cooled to 0° and 11.6 ml (100 mmole) of benzyl mercaptan was added dropwise at 0°. After addition was complete, the reaction mixture was allowed to warm to 25° and stirred at this temperature for 1 hour. The reaction mixture was then re-cooled to 0° and 10.0 g (91 mmole) of 2-fluoro-3-methyl pyridine was added dropwise. The mixture was allowed to warm to 25° and stirred at this temperature for 18 hours. The mixture was poured into 100 mls of water and extracted twice with ethyl ether and ethylacetate. The combined organic extracts were washed with a saturated solution of sodium bicarbonate and dried over sodium sulfate. Concentration gave 24 g of a yellow oil. Flash chromatography in a 10% ethyl ether/hexanes mixture gave 6.3 g clear oil.

NMR ($CDCl_3$) 2.25 (s, 3H, $CH_3$),
4.52 (s, 2H, $SCH_2C_6H_5$),
6.95 (dd, 1H),
7.30 (m, 4H),
7.48 (m, 2H),
8.34 (dd, 1H).

Step B.
N-(1,1-dimethylethyl)-3-methyl-2-pyridinesulfonamide

A mixture of 45 mls of concentrated hydrochloric acid, 500 mls of methylene chloride, 260 ml of water, and 25.0 g (116 mmole) of 3-methyl-2-(phenylmethylthio)pyridine was cooled to 0°. Maintaining a temperature of −5° to 0°, 500 mls (338 mmole) of 5% sodium hypochlorite was added dropwise. The resulting yellow emulsion was stirred at 0° an additional 30 minutes. The reaction mixture was then extracted with methylene chloride and dried over sodium sulfate. The solution was filtered into a reaction flask and cooled to −78° and 50 mls (476 mmole) of t-butyl amine added. The reaction mixture was allowed to warm to room temperature, poured into water, and extracted with methylene chloride. The solution was dried over sodium sulfate and concentrated to a brown oil. The resulting oil was triturated with ethyl ether and hexane to yield 10 g of tan solid, m.p. 107–110.

NMR (CDCl$_3$) 1.27 (s, 9H, C(CH$_3$)$_3$),
2.68 (s, 3H, CH$_3$),
5.14 (s, 1H),
7.34 (m, 1H),
7.66 (dd, 1H),
8.46 (dd, 1H).

Step C.
N-(1,1-dimethylethyl)-3-(methylthiomethyl)-2-pyridine-sulfonamide A solution of 5.0 g (21.9 mmole) of the 3-methyl-2-(1,1-dimethyl-2-(1, 1-dimethylethyl)aminosulfonyl-pyridine in 50 mls of tetrahydrofuran was cooled to −78° and 52 mls (67.6 mmole) of 1.3M n-butyllithium was added. After addition was complete, the reaction mixture was stirred at this temperature for 20 minutes, then 7.3 mls (81.0 mmole) of dimethyl disulfide was added dropwise at −78°. The reaction mixture was quenched with brine, extracted with methylene chloride and the combined organic extracts were dried over sodium sulfate. Concentration gave a yellow oil. Flash chromatography in a 20% ethyl acetate/hexanes mixture gave 2.3 g solid, m.p. 89–92.

NMR (CDCl$_3$) 1.27 (s, 9H, C(CH$_3$)$_3$),
2.08 (s, 3H, SCH$_3$),
4.20 (s, 2H, CH$_2$S)),
5.34 (s, 1H),
7.45 (dd, 1H),
7.93 (dd, 1H),
8.55 (dd, 1H).

Step D. 3-(Methylthiomethyl)-2-pyridinesulfonamide

A solution of 2.1 g (7.7 mmole) in 35 mls trifluoroacetic acid was stirred at room temperature for 24 hours and then warmed to 40° for 24 hours. The trifluoroacetic acid was removed under vacuum. The resulting brown oil was triturated with n-butylchloride to yield 0.75 g solid, m.p. 68–70.

NMR (CDCl$_3$) 2.06 (s, 3H, SCH$_3$),
4.17 (s, 2H, SCH$_2$),
5.55 (s, 2H),
7.49 (dd, 1H),
7.98 (dd, 1H),
8.53 (dd, 1H).

Step E.
2-[[(4,6-dimethoxypyrimidin-2-yl)amino-carbonyl-]aminosulfonyl]-3-methylthiomethyl-pyridine To a suspension of 0.18 g (0.82 mmole) 3-(methyl-thiomethyl)-2-aminosulfonylpyridine and 0.227 g (0.82 mmole) of 4,6-dimethoxypyrimidin-2-yl phenyl carbamate in 3 mls acetonitrile was added 0.126 mls (0.82 mmole) of 1,8-diazabicyclo[5.4.0]undec-7-ene. The resulting solution was stirred at room temperature for 5 minutes. The addition of 2 mls of water, followed by the dropwise addition of 10% hydrochloric acid produced a white precipitate which was collected by filtration to provide 0.270 g of the subject compound, m.p. 145°–147°.

NMR (CDCl$_3$) 2.09 (s, 3H, SCH$_3$),
3.50 (s, 6H, OCH$_3$),
4.27 (s, 2H, SCH$_2$),
5.80 (s, 1H),
7.33 (s, 1H),
7.49 (dd, 1H),
8.10 (d, 1H),
8.50 (d, 1H),
12.83 (s, 1H).

Using these methods and those described in Equations 1–5, the compounds of Tables 1–14 can be prepared.

TABLE 1

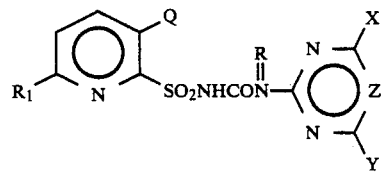

| R$_1$ | Q | R | Z | X | Y | m.p. (°C.) |
|---|---|---|---|---|---|---|
| H | CH$_2$OCH$_3$ | H | CH | CH$_3$ | CH$_3$ | |
| H | CH$_2$OCH$_3$ | H | CH | CH$_3$ | OCH$_3$ | |
| H | CH$_2$OCH$_3$ | H | CH | CH$_3$ | C$_2$H$_5$ | |
| H | CH$_2$OCH$_3$ | H | CH | CH$_3$ | NHCH$_3$ | |
| H | CH$_2$OCH$_3$ | H | CH | CH$_3$ | CH$_2$OCH$_3$ | |
| H | CH$_2$OCH$_3$ | H | CH | CH$_3$ | CH(OCH$_3$)$_2$ | |
| H | CH$_2$OCH$_3$ | H | CH | OCH$_3$ | CH$_2$OCH$_3$ | |
| H | CH$_2$OCH$_3$ | H | CH | OCH$_3$ | OCH$_3$ | 163–168 |
| H | CH$_2$OCH$_3$ | H | CH | OCH$_3$ | C$_2$H$_5$ | |
| H | CH$_2$OCH$_3$ | H | CH | OCH$_3$ | NHCH$_3$ | |
| H | CH$_2$OCH$_3$ | H | CH | OCH$_3$ | CH(OCH$_3$)$_2$ | |
| H | CH$_2$OCH$_3$ | H | CH | OCH$_2$CH$_3$ | CH$_3$ | |
| H | CH$_2$OCH$_3$ | H | CH | OCH$_2$CH$_3$ | OCH$_3$ | |
| H | CH$_2$OCH$_3$ | H | CH | OCH$_2$CH$_3$ | C$_2$H$_5$ | |

TABLE 1-continued $$\text{R}_1\text{-pyridine(Q)-SO}_2\text{NHCON(R)-triazine/pyrimidine(X,Y,Z)}$$

| R₁ | Q | R | Z | X | Y | m.p. (°C.) |
|---|---|---|---|---|---|---|
| H | CH₂OCH₃ | H | CH | OCH₂CH₃ | NHCH₃ | |
| H | CH₂OCH₃ | H | CH | OCH₂CH₃ | CH₂OCH₃ | |
| H | CH₂OCH₃ | H | CH | OCH₂CH₃ | CH(OCH₃)₂ | |
| H | CH₂OCH₃ | H | CH | Cl | OCH₃ | 149–150 |
| H | CH₂OCH₃ | H | CH | Cl | NHCH₃ | |
| H | CH₂OCH₃ | H | CH | OCF₂H | CH₃ | |
| H | CH₂OCH₃ | H | CH | OCF₂H | OCH₃ | |
| H | CH₂OCH₃ | H | CH | OCF₂H | C₂H₅ | |
| H | CH₂OCH₃ | H | CH | OCF₂H | NHCH₃ | |
| H | CH₂OCH₃ | H | CH | OCF₂H | CH₂OCH₃ | |
| H | CH₂OCH₃ | H | CH | OCF₂H | CH(OCH₃)₂ | |
| H | CH₂OCH₃ | H | CH | CH₂CF₃ | CH₃ | |
| H | CH₂OCH₃ | H | CH | CH₂CF₃ | OCH₃ | |
| H | CH₂OCH₃ | H | CH | CH₂CF₃ | C₂H₅ | |
| H | CH₂OCH₃ | H | CH | CH₂CF₃ | NHCH₃ | |
| H | CH₂OCH₃ | H | CH | CH₂CF₃ | CH₂OCH₃ | |
| H | CH₂OCH₃ | H | CH | CH₂CF₃ | CH(OCH₃)₂ | |
| H | CH₂OCH₃ | H | N | CH₃ | CH₃ | |
| H | CH₂OCH₃ | H | N | CH₃ | OCH₃ | 139–141 |
| H | CH₂OCH₃ | H | N | CH₃ | C₂H₅ | |
| H | CH₂OCH₃ | H | N | CH₃ | NHCH₃ | |
| H | CH₂OCH₃ | H | N | CH₃ | CH₂OCH₃ | |
| H | CH₂OCH₃ | H | N | OCH₃ | CH(OCH₃)₂ | |
| H | CH₂OCH₃ | H | N | OCH₃ | CH₂OCH₃ | |
| H | CH₂OCH₃ | H | N | OCH₃ | OCH₃ | 158–160 |
| H | CH₂OCH₃ | H | N | OCH₃ | C₂H₅ | |
| H | CH₂OCH₃ | H | N | OCH₃ | NHCH₃ | |
| H | CH₂OCH₃ | H | N | OCH₃ | CH(OCH₃)₂ | |
| H | CH₂OCH₃ | H | N | OCH₂CH₃ | CH₃ | |
| H | CH₂OCH₃ | H | N | OCH₂CH₃ | OCH₃ | |
| H | CH₂OCH₃ | H | N | OCH₂CH₃ | C₂H₅ | |
| H | CH₂OCH₃ | H | N | OCH₂CH₃ | NHCH₃ | 156–158 |
| H | CH₂OCH₃ | H | N | OCH₂CH₃ | CH₂OCH₃ | |
| H | CH₂OCH₃ | H | N | OCH₂CH₃ | CH(OCH₃)₂ | |
| H | CH₂OCH₃ | H | N | CH₂CF₃ | CH₃ | |
| H | CH₂OCH₃ | H | N | CH₂CF₃ | OCH₃ | |
| H | CH₂OCH₃ | H | N | CH₂CF₃ | C₂H₅ | |
| H | CH₂OCH₃ | H | N | CH₂CF₃ | NHCH₃ | |
| H | CH₂OCH₃ | H | N | CH₂CF₃ | CH₂OCH₃ | |
| H | CH₂OCH₃ | H | N | CH₂CF₃ | CH₂(OCH₃)₂ | |
| CH₃ | CH₂OCH₃ | H | CH | CH₃ | CH₃ | |
| CH₃ | CH₂OCH₃ | H | CH | CH₃ | OCH₃ | |
| CH₃ | CH₂OCH₃ | H | CH | OCH₃ | OCH₃ | |
| CH₃ | CH₂OCH₃ | H | CH | Cl | OCH₃ | |
| CH₃ | CH₂OCH₃ | H | N | CH₃ | CH₃ | |
| CH₃ | CH₂OCH₃ | H | N | CH₃ | OCH₃ | |
| CH₃ | CH₂OCH₃ | H | N | OCH₃ | OCH₃ | |
| CH₃ | CH₂OCH₃ | H | N | OCH₂CH₃ | NHCH₃ | |
| CH₂Cl | CH₂OCH₃ | H | CH | CH₃ | OCH₃ | |
| CH₂Cl | CH₂OCH₃ | H | N | CH₃ | OCH₃ | |
| CH₂Br | CH₂OCH₃ | H | CH | CH₃ | OCH₃ | |
| CH₂Br | CH₂OCH₃ | H | N | CH₃ | OCH₃ | |
| CH₂F | CH₂OCH₃ | H | CH | CH₃ | OCH₃ | |
| CH₂F | CH₂OCH₃ | H | N | CH₃ | OCH₃ | |
| CH₂I | CH₂OCH₃ | H | CH | CH₃ | OCH₃ | |
| CH₂I | CH₂OCH₃ | H | N | CH₃ | OCH₃ | |
| F | CH₂OCH₃ | H | CH | CH₃ | CH₃ | |
| F | CH₂OCH₃ | H | CH | CH₃ | OCH₃ | |
| F | CH₂OCH₃ | H | CH | OCH₃ | OCH₃ | |
| F | CH₂OCH₃ | H | CH | Cl | OCH₃ | |
| F | CH₂OCH₃ | H | N | CH₃ | CH₃ | |
| F | CH₂OCH₃ | H | N | CH₃ | OCH₃ | |
| F | CH₂OCH₃ | H | N | OCH₃ | OCH₃ | |
| F | CH₂OCH₃ | H | N | OCH₂CH₃ | NHCH₃ | |
| Cl | CH₂OCH₃ | H | CH | CH₃ | OCH₃ | 165–169 |
| Cl | CH₂OCH₃ | H | CH | OCH₃ | OCH₃ | 138–142 |
| Cl | CH₂OCH₃ | H | CH | Cl | OCH₃ | 161–164 |
| Cl | CH₂OCH₃ | H | N | CH₃ | CH₃ | |
| Cl | CH₂OCH₃ | H | N | CH₃ | OCH₃ | 130–135 |
| Cl | CH₂OCH₃ | H | N | OCH₃ | OCH₃ | 135–140 |
| Cl | CH₂OCH₃ | H | N | OCH₂CH₃ | NHCH₃ | 136–142 |

TABLE 1-continued

| R₁ | Q | R | Z | X | Y | m.p. (°C.) |
|---|---|---|---|---|---|---|
| Cl | CH₂OCH₃ | H | CH | CH₃ | CH₃ | 168–171 |
| Cl | CH₂OCH₃ | CH₃ | N | OCH₃ | CH₃ | 121–124 |
| Cl | CH₂OCH₃ | CH₃ | CH | OCH₃ | OCH₃ | 130–134 |
| Br | CH₂OCH₃ | H | CH | CH₃ | CH₃ | |
| Br | CH₂OCH₃ | H | CH | CH₃ | OCH₃ | |
| Br | CH₂OCH₃ | H | CH | OCH₃ | OCH₃ | |
| Br | CH₂OCH₃ | H | CH | Cl | OCH₃ | |
| Br | CH₂OCH₃ | H | N | CH₃ | CH₃ | |
| Br | CH₂OCH₃ | H | N | CH₃ | OCH₃ | |
| Br | CH₂OCH₃ | H | N | OCH₃ | OCH₃ | |
| Br | CH₂OCH₃ | H | N | OCH₂CH₃ | NHCH₃ | |
| I | CH₂OCH₃ | H | CH | CH₃ | OCH₃ | |
| I | CH₂OCH₃ | H | N | CH₃ | OCH₃ | |
| NO₂ | CH₂OCH₃ | H | CH | CH₃ | CH₃ | |
| NO₂ | CH₂OCH₃ | H | CH | CH₃ | OCH₃ | |
| NO₂ | CH₂OCH₃ | H | CH | OCH₃ | OCH₃ | |
| NO₂ | CH₂OCH₃ | H | CH | Cl | OCH₃ | |
| NO₂ | CH₂OCH₃ | H | N | CH₃ | CH₃ | |
| NO₂ | CH₂OCH₃ | H | N | CH₃ | OCH₃ | |
| NO₂ | CH₂OCH₃ | H | N | OCH₃ | OCH₃ | |
| NO₂ | CH₂OCH₃ | H | N | OCH₂CH₃ | NHCH₃ | |
| OCH₃ | CH₂OCH₃ | H | CH | CH₃ | CH₃ | |
| OCH₃ | CH₂OCH₃ | H | CH | CH₃ | OCH₃ | |
| OCH₃ | CH₂OCH₃ | H | CH | OCH₃ | OCH₃ | |
| OCH₃ | CH₂OCH₃ | H | CH | Cl | OCH₃ | |
| OCH₃ | CH₂OCH₃ | H | N | CH₃ | CH₃ | |
| OCH₃ | CH₂OCH₃ | H | N | CH₃ | OCH₃ | |
| OCH₃ | CH₂OCH₃ | H | N | OCH₃ | OCH₃ | |
| OCH₃ | CH₂OCH₃ | H | N | OCH₂CH₃ | NHCH₃ | |
| SO₂N(CH₃)₂ | CH₂OCH₃ | H | CH | CH₃ | CH₃ | |
| SO₂N(CH₃)₂ | CH₂OCH₃ | H | CH | CH₃ | OCH₃ | |
| SO₂N(CH₃)₂ | CH₂OCH₃ | H | CH | OCH₃ | OCH₃ | |
| SO₂N(CH₃)₂ | CH₂OCH₃ | H | CH | Cl | OCH₃ | |
| SO₂N(CH₃)₂ | CH₂OCH₃ | H | N | CH₃ | CH₃ | |
| SO₂N(CH₃)₂ | CH₂OCH₃ | H | N | CH₃ | OCH₃ | |
| SO₂N(CH₃)₂ | CH₂OCH₃ | H | N | OCH₃ | OCH₃ | |
| SO₂N(CH₃)₂ | CH₂OCH₃ | H | N | OCH₂CH₃ | NHCH₃ | |
| SCH₃ | CH₂OCH₃ | H | CH | CH₃ | CH₃ | |
| SCH₃ | CH₂OCH₃ | H | CH | CH₃ | OCH₃ | |
| SCH₃ | CH₂OCH₃ | H | CH | OCH₃ | OCH₃ | |
| SCH₃ | CH₂OCH₃ | H | CH | Cl | OCH₃ | |
| SCH₃ | CH₂OCH₃ | H | N | CH₃ | CH₃ | |
| SCH₃ | CH₂OCH₃ | H | N | CH₃ | OCH₃ | |
| SCH₃ | CH₂OCH₃ | H | N | OCH₃ | OCH₃ | |
| SCH₃ | CH₂OCH₃ | H | N | OCH₂CH₃ | NHCH₃ | |
| S(O)CH₃ | CH₂OCH₃ | H | CH | CH₃ | CH₃ | |
| S(O)CH₃ | CH₂OCH₃ | H | CH | CH₃ | OCH₃ | |
| S(O)CH₃ | CH₂OCH₃ | H | CH | OCH₃ | OCH₃ | |
| S(O)CH₃ | CH₂OCH₃ | H | CH | Cl | OCH₃ | |
| S(O)CH₃ | CH₂OCH₃ | H | N | CH₃ | CH₃ | |
| S(O)CH₃ | CH₂OCH₃ | H | N | CH₃ | OCH₃ | |
| S(O)CH₃ | CH₂OCH₃ | H | N | OCH₃ | OCH₃ | |
| S(O)CH₃ | CH₂OCH₃ | H | N | OCH₂CH₃ | NHCH₃ | |
| SO₂CH₃ | CH₂OCH₃ | H | CH | CH₃ | CH₃ | |
| SO₂CH₃ | CH₂OCH₃ | H | CH | CH₃ | OCH₃ | |
| SO₂CH₃ | CH₂OCH₃ | H | CH | OCH₃ | OCH₃ | |
| SO₂CH₃ | CH₂OCH₃ | H | CH | Cl | OCH₃ | |
| SO₂CH₃ | CH₂OCH₃ | H | N | CH₃ | CH₃ | |
| SO₂CH₃ | CH₂OCH₃ | H | N | CH₃ | OCH₃ | |
| SO₂CH₃ | CH₂OCH₃ | H | N | OCH₃ | OCH₃ | |
| SO₂CH₃ | CH₂OCH₃ | H | N | OCH₂CH₃ | NHCH₃ | |
| CO₂CH₃ | CH₂OCH₃ | H | CH | CH₃ | CH₃ | |
| CO₂CH₃ | CH₂OCH₃ | H | CH | CH₃ | OCH₃ | |
| CO₂CH₃ | CH₂OCH₃ | H | CH | CH₃ | C₂H₅ | |
| CO₂CH₃ | CH₂OCH₃ | H | CH | CH₃ | NHCH₃ | |
| CO₂CH₃ | CH₂OCH₃ | H | CH | CH₃ | CH₂OCH₃ | |
| CO₂CH₃ | CH₂OCH₃ | H | CH | CH₃ | CH(OCH₃)₂ | |
| CO₂CH₃ | CH₂OCH₃ | H | CH | OCH₃ | CH₂OCH₃ | |
| CO₂CH₃ | CH₂OCH₃ | H | CH | OCH₃ | OCH₃ | |
| CO₂CH₃ | CH₂OCH₃ | H | CH | OCH₃ | C₂H₅ | |
| CO₂CH₃ | CH₂OCH₃ | H | CH | OCH₃ | NHCH₃ | |

TABLE 1-continued

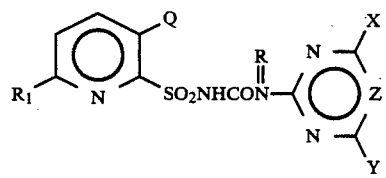

| R₁ | Q | R | Z | X | Y | m.p. (°C.) |
|---|---|---|---|---|---|---|
| CO₂CH₃ | CH₂OCH₃ | H | CH | OCH₃ | CH(OCH₃)₂ | |
| CO₂CH₃ | CH₂OCH₃ | H | CH | OCH₂CH₃ | CH₃ | |
| CO₂CH₃ | CH₂OCH₃ | H | CH | OCH₂CH₃ | OCH₃ | |
| CO₂CH₃ | CH₂OCH₃ | H | CH | OCH₂CH₃ | C₂H₅ | |
| CO₂CH₃ | CH₂OCH₃ | H | CH | OCH₂CH₃ | NHCH₃ | |
| CO₂CH₃ | CH₂OCH₃ | H | CH | OCH₂CH₃ | CH₂OCH₃ | |
| CO₂CH₃ | CH₂OCH₃ | H | CH | OCH₂CH₃ | CH(OCH₃)₂ | |
| CO₂CH₃ | CH₂OCH₃ | H | CH | Cl | OCH₃ | |
| CO₂CH₃ | CH₂OCH₃ | H | CH | Cl | NHCH₃ | |
| CO₂CH₃ | CH₂OCH₃ | H | CH | OCF₂H | CH₃ | |
| CO₂CH₃ | CH₂OCH₃ | H | CH | OCF₂H | OCH₃ | |
| CO₂CH₃ | CH₂OCH₃ | H | CH | OCF₂H | C₂H₅ | |
| CO₂CH₃ | CH₂OCH₃ | H | CH | OCF₂H | NHCH₃ | |
| CO₂CH₃ | CH₂OCH₃ | H | CH | OCF₂H | CH₂OCH₃ | |
| CO₂CH₃ | CH₂OCH₃ | H | CH | OCF₂H | CH(OCH₃)₂ | |
| CO₂CH₃ | CH₂OCH₃ | H | CH | CH₂CF₃ | CH₃ | |
| CO₂CH₃ | CH₂OCH₃ | H | CH | CH₂CF₃ | OCH₃ | |
| CO₂CH₃ | CH₂OCH₃ | H | CH | CH₂CF₃ | C₂H₅ | |
| CO₂CH₃ | CH₂OCH₃ | H | CH | CH₂CF₃ | NHCH₃ | |
| CO₂CH₃ | CH₂OCH₃ | H | CH | CH₂CF₃ | CH₂OCH₃ | |
| CO₂CH₃ | CH₂OCH₃ | H | CH | CH₂CF₃ | CH(OCH₃)₂ | |
| CO₂CH₃ | CH₂OCH₃ | H | N | CH₃ | CH₃ | |
| CO₂CH₃ | CH₂OCH₃ | H | N | CH₃ | OCH₃ | |
| CO₂CH₃ | CH₂OCH₃ | H | N | CH₃ | C₂H₅ | |
| CO₂CH₃ | CH₂OCH₃ | H | N | CH₃ | NHCH₃ | |
| CO₂CH₃ | CH₂OCH₃ | H | N | CH₃ | CH₂OCH₃ | |
| CO₂CH₃ | CH₂OCH₃ | H | N | CH₃ | CH(OCH₃)₂ | |
| CO₂CH₃ | CH₂OCH₃ | H | N | OCH₃ | CH₂OCH₃ | |
| CO₂CH₃ | CH₂OCH₃ | H | N | OCH₃ | OCH₃ | |
| CO₂CH₃ | CH₂OCH₃ | H | N | OCH₃ | C₂H₅ | |
| CO₂CH₃ | CH₂OCH₃ | H | N | OCH₃ | NHCH₃ | |
| CO₂CH₃ | CH₂OCH₃ | H | N | OCH₃ | CH(OCH₃)₂ | |
| CO₂CH₃ | CH₂OCH₃ | H | N | OCH₂CH₃ | CH₃ | |
| CO₂CH₃ | CH₂OCH₃ | H | N | OCH₂CH₃ | OCH₃ | |
| CO₂CH₃ | CH₂OCH₃ | H | N | OCH₂CH₃ | C₂H₅ | |
| CO₂CH₃ | CH₂OCH₃ | H | N | OCH₂CH₃ | NHCH₃ | |
| CO₂CH₃ | CH₂OCH₃ | H | N | OCH₂CH₃ | CH₂OCH₃ | |
| CO₂CH₃ | CH₂OCH₃ | H | N | OCH₂CH₃ | CH(OCH₃)₂ | |
| CO₂CH₃ | CH₂OCH₃ | H | N | CH₂CF₃ | CH₃ | |
| CO₂CH₃ | CH₂OCH₃ | H | N | CH₂CF₃ | OCH₃ | |
| CO₂CH₃ | CH₂OCH₃ | H | N | CH₂CF₃ | C₂H₅ | |
| CO₂CH₃ | CH₂OCH₃ | H | N | CH₂CF₃ | NHCH₃ | 5 |
| CO₂CH₃ | CH₂OCH₃ | H | N | CH₂CF₃ | CH₂OCH₃ | |
| CO₂CH₃ | CH₂OCH₃ | H | N | CH₂CF₃ | CH₂(OCH₃)₂ | |
| CO₂CH₂CH₃ | CH₂OCH₃ | H | CH | CH₃ | CH₃ | |
| CO₂CH₂CH₃ | CH₂OCH₃ | H | CH | CH₃ | OCH₃ | |
| CO₂CH₂CH₃ | CH₂OCH₃ | H | CH | OCH₃ | OCH₃ | |
| CO₂CH₂CH₃ | CH₂OCH₃ | H | CH | Cl | OCH₃ | |
| CO₂CH₂CH₃ | CH₂OCH₃ | H | N | CH₃ | CH₃ | |
| CO₂CH₂CH₃ | CH₂OCH₃ | H | N | CH₃ | OCH₃ | |
| CO₂CH₂CH₃ | CH₂OCH₃ | H | N | OCH₃ | OCH₃ | |
| CO₂CH₂CH₃ | CH₂OCH₃ | H | N | OCH₂CH₃ | NHCH₃ | |
| CO₂(CH₂)₂CH₃ | CH₂OCH₃ | H | CH | CH₃ | CH₃ | |
| CO₂(CH₂)₂CH₃ | CH₂OCH₃ | H | CH | CH₃ | OCH₃ | |
| CO₂(CH₂)₂CH₃ | CH₂OCH₃ | H | CH | OCH₃ | OCH₃ | |
| CO₂(CH₂)₂CH₃ | CH₂OCH₃ | H | CH | Cl | OCH₃ | |
| CO₂(CH₂)₂CH₃ | CH₂OCH₃ | H | N | CH₃ | CH₃ | |
| CO₂(CH₂)₂CH₃ | CH₂OCH₃ | H | N | CH₃ | OCH₃ | |
| CO₂(CH₂)₂CH₃ | CH₂OCH₃ | H | N | OCH₃ | OCH₃ | |
| CO₂(CH₂)₂CH₃ | CH₂OCH₃ | H | N | OCH₂CH₃ | NHCH₃ | |
| CO₂CH₂CH=CH₂ | CH₂OCH₃ | H | CH | CH₃ | CH₃ | |
| CO₂CH₂CH=CH₂ | CH₂OCH₃ | H | CH | CH₃ | OCH₃ | |
| CO₂CH₂CH=CH₂ | CH₂OCH₃ | H | CH | OCH₃ | OCH₃ | |
| CO₂CH₂CH=CH₂ | CH₂OCH₃ | H | CH | Cl | OCH₃ | |
| CO₂CH₂CH=CH₂ | CH₂OCH₃ | H | N | CH₃ | CH₃ | |
| CO₂CH₂CH=CH₂ | CH₂OCH₃ | H | N | CH₃ | OCH₃ | |
| CO₂CH₂CH=CH₂ | CH₂OCH₃ | H | N | OCH₃ | OCH₃ | |
| CO₂CH₂CH=CH₂ | CH₂OCH₃ | H | N | OCH₂CH₃ | NHCH₃ | |
| CO₂CH₂C≡CH | CH₂OCH₃ | H | CH | CH₃ | CH₃ | |
| CO₂CH₂C≡CH | CH₂OCH₃ | H | CH | CH₃ | OCH₃ | |
| CO₂CH₂C≡CH | CH₂OCH₃ | H | CH | OCH₃ | OCH₃ | |

TABLE 1-continued

| $R_1$ | Q | R | Z | X | Y | m.p. (°C.) |
|---|---|---|---|---|---|---|
| $CO_2CH_2C\equiv CH$ | $CH_2OCH_3$ | H | CH | Cl | $OCH_3$ | |
| $CO_2CH_2C\equiv CH$ | $CH_2OCH_3$ | H | N | $CH_3$ | $CH_3$ | |
| $CO_2CH_2C\equiv CH$ | $CH_2OCH_3$ | H | N | $CH_3$ | $OCH_3$ | |
| $CO_2CH_2C\equiv CH$ | $CH_2OCH_3$ | H | N | $OCH_3$ | $OCH_3$ | |
| $CO_2CH_2C\equiv CH$ | $CH_2OCH_3$ | H | N | $OCH_2CH_3$ | $NHCH_3$ | |
| $CO_2(CH_2)_2OCH_3$ | $CH_2OCH_3$ | H | CH | $CH_3$ | $OCH_3$ | |
| $CO_2(CH_2)_2OCH_3$ | $CH_2OCH_3$ | H | N | $CH_3$ | $OCH_3$ | |
| $CO_2(CH_2)_2Cl$ | $CH_2OCH_3$ | H | CH | $CH_3$ | $OCH_3$ | |
| $CO_2(CH_2)_2Cl$ | $CH_2OCH_3$ | H | N | $CH_3$ | $OCH_3$ | |
| $OCH_2Cl$ | $CH_2OCH_3$ | H | CH | $CH_3$ | $CH_3$ | |
| $OCH_2Cl$ | $CH_2OCH_3$ | H | CH | $CH_3$ | $OCH_3$ | |
| $OCH_2Cl$ | $CH_2OCH_3$ | H | CH | $OCH_3$ | $OCH_3$ | |
| $OCH_2Cl$ | $CH_2OCH_3$ | H | CH | Cl | $OCH_3$ | |
| $OCH_2Cl$ | $CH_2OCH_3$ | H | N | $CH_3$ | $CH_3$ | |
| $OCH_2Cl$ | $CH_2OCH_3$ | H | N | $CH_3$ | $OCH_3$ | |
| $OCH_2Cl$ | $CH_2OCH_3$ | H | N | $OCH_3$ | $OCH_3$ | |
| $OCH_2Cl$ | $CH_2OCH_3$ | H | N | $OCH_2CH_3$ | $NHCH_3$ | |
| $SCH_2Cl$ | $CH_2OCH_3$ | H | CH | $CH_3$ | $CH_3$ | |
| $SCH_2Cl$ | $CH_2OCH_3$ | H | CH | $CH_3$ | $OCH_3$ | |
| $SCH_2Cl$ | $CH_2OCH_3$ | H | CH | $OCH_3$ | $OCH_3$ | |
| $SCH_2Cl$ | $CH_2OCH_3$ | H | CH | Cl | $OCH_3$ | |
| $SCH_2Cl$ | $CH_2OCH_3$ | H | N | $CH_3$ | $CH_3$ | |
| $SCH_2Cl$ | $CH_2OCH_3$ | H | N | $CH_3$ | $OCH_3$ | |
| $SCH_2Cl$ | $CH_2OCH_3$ | H | N | $OCH_3$ | $OCH_3$ | |
| $SCH_2Cl$ | $CH_2OCH_3$ | H | N | $OCH_2CH_3$ | $NHCH_3$ | |
| $NH_2$ | $CH_2OCH_3$ | H | CH | $CH_3$ | $OCH_3$ | |
| $NH_2$ | $CH_2OCH_3$ | H | N | $CH_3$ | $OCH_3$ | |
| $NHCH_3$ | $CH_2OCH_3$ | H | CH | $CH_3$ | $OCH_3$ | |
| $NHCH_3$ | $CH_2OCH_3$ | H | N | $CH_3$ | $OCH_3$ | |
| $N(CH_3)_2$ | $CH_2OCH_3$ | H | CH | $CH_3$ | $CH_3$ | |
| $N(CH_3)_2$ | $CH_2OCH_3$ | H | CH | $CH_3$ | $OCH_3$ | |
| $N(CH_3)_2$ | $CH_2OCH_3$ | H | CH | $OCH_3$ | $OCH_3$ | |
| $N(CH_3)_2$ | $CH_2OCH_3$ | H | CH | Cl | $OCH_3$ | |
| $N(CH_3)_2$ | $CH_2OCH_3$ | H | N | $CH_3$ | $CH_3$ | |
| $N(CH_3)_2$ | $CH_2OCH_3$ | H | N | $CH_3$ | $OCH_3$ | |
| $N(CH_3)_2$ | $CH_2OCH_3$ | H | N | $OCH_3$ | $OCH_3$ | |
| $N(CH_3)_2$ | $CH_2OCH_3$ | H | N | $OCH_2CH_3$ | $NHCH_3$ | |
| $N(CH_3)CH_2CH_3$ | $CH_2OCH_3$ | H | CH | $CH_3$ | $OCH_3$ | |
| $N(CH_3)CH_2CH_3$ | $CH_2OCH_3$ | H | N | $CH_3$ | $OCH_3$ | |
| $C(O)N(CH_3)_2$ | $CH_2OCH_3$ | H | CH | $CH_3$ | $CH_3$ | |
| $C(O)N(CH_3)_2$ | $CH_2OCH_3$ | H | CH | $CH_3$ | $OCH_3$ | |
| $C(O)N(CH_3)_2$ | $CH_2OCH_3$ | H | CH | $OCH_3$ | $OCH_3$ | |
| $C(O)N(CH_3)_2$ | $CH_2OCH_3$ | H | CH | Cl | $OCH_3$ | |
| $C(O)N(CH_3)_2$ | $CH_2OCH_3$ | H | N | $CH_3$ | $CH_3$ | |
| $C(O)N(CH_3)_2$ | $CH_2OCH_3$ | H | N | $CH_3$ | $OCH_3$ | |
| $C(O)N(CH_3)_2$ | $CH_2OCH_3$ | H | N | $OCH_3$ | $OCH_3$ | |
| $C(O)N(CH_3)_2$ | $CH_2OCH_3$ | H | N | $OCH_2CH_3$ | $NHCH_3$ | |
| H | $CH_2OCH_3$ | $CH_3$ | CH | $CH_3$ | $CH_3$ | |
| H | $CH_2OCH_3$ | $CH_3$ | CH | $CH_3$ | $OCH_3$ | |
| H | $CH_2OCH_3$ | $CH_3$ | CH | $CH_3$ | $C_2H_5$ | |
| H | $CH_2OCH_3$ | $CH_3$ | CH | $CH_3$ | $NHCH_3$ | |
| H | $CH_2OCH_3$ | $CH_3$ | CH | $CH_3$ | $CH_2OCH_3$ | |
| H | $CH_2OCH_3$ | $CH_3$ | CH | $CH_3$ | $CH(OCH_3)_2$ | |
| H | $CH_2OCH_3$ | $CH_3$ | CH | $OCH_3$ | $CH_2OCH_3$ | |
| H | $CH_2OCH_3$ | $CH_3$ | CH | $OCH_3$ | $OCH_3$ | |
| H | $CH_2OCH_3$ | $CH_3$ | CH | $OCH_3$ | $C_2H_5$ | |
| H | $CH_2OCH_3$ | $CH_3$ | CH | $OCH_3$ | $NHCH_3$ | |
| H | $CH_2OCH_3$ | $CH_3$ | CH | $OCH_3$ | $CH(OCH_3)_2$ | |
| H | $CH_2OCH_3$ | $CH_3$ | CH | $OCH_3$ | $CH_2OCH_3$ | |
| H | $CH_2OCH_3$ | $CH_3$ | CH | $OCH_2CH_3$ | $CH_3$ | |
| H | $CH_2OCH_3$ | $CH_3$ | CH | $OCH_2CH_3$ | $OCH_3$ | |
| H | $CH_2OCH_3$ | $CH_3$ | CH | $OCH_2CH_3$ | $C_2H_5$ | |
| H | $CH_2OCH_3$ | $CH_3$ | CH | $OCH_2CH_3$ | $NHCH_3$ | |
| H | $CH_2OCH_3$ | $CH_3$ | CH | $OCH_2CH_3$ | $CH_2OCH_3$ | |
| H | $CH_2OCH_3$ | $CH_3$ | CH | $OCH_2CH_3$ | $CH(OCH_3)_2$ | |
| H | $CH_2OCH_3$ | $CH_3$ | CH | Cl | $OCH_3$ | |
| H | $CH_2OCH_3$ | $CH_3$ | CH | Cl | $NHCH_3$ | |
| H | $CH_2OCH_3$ | $CH_3$ | CH | $OCF_2H$ | $CH_3$ | |
| H | $CH_2OCH_3$ | $CH_3$ | CH | $OCF_2H$ | $OCH_3$ | |
| H | $CH_2OCH_3$ | $CH_3$ | CH | $OCF_2H$ | $C_2H_5$ | |
| H | $CH_2OCH_3$ | $CH_3$ | CH | $OCF_2H$ | $NHCH_3$ | |

TABLE 1-continued

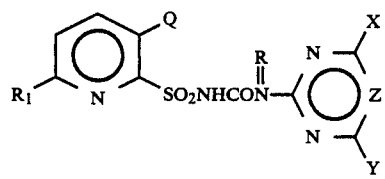

| R₁ | Q | R | Z | X | Y | m.p. (°C.) |
|---|---|---|---|---|---|---|
| H | CH₂OCH₃ | CH₃ | CH | OCF₂H | CH₂OCH₃ | |
| H | CH₂OCH₃ | CH₃ | CH | OCF₂H | CH(OCH₃)₂ | |
| H | CH₂OCH₃ | CH₃ | CH | CH₂CF₃ | CH₃ | |
| H | CH₂OCH₃ | CH₃ | CH | CH₂CF₃ | OCH₃ | |
| H | CH₂OCH₃ | CH₃ | CH | CH₂CF₃ | C₂H₅ | |
| H | CH₂OCH₃ | CH₃ | CH | CH₂CF₃ | NHCH₃ | |
| H | CH₂OCH₃ | CH₃ | CH | CH₂CF₃ | CH₂OCH₃ | |
| H | CH₂OCH₃ | CH₃ | CH | CH₂CF₃ | CH(OCH₃)₂ | |
| H | CH₂OCH₃ | CH₃ | N | CH₃ | CH₃ | |
| H | CH₂OCH₃ | CH₃ | N | CH₃ | OCH₃ | |
| H | CH₂OCH₃ | CH₃ | N | CH₃ | C₂H₅ | |
| H | CH₂OCH₃ | CH₃ | N | CH₃ | NHCH₃ | |
| H | CH₂OCH₃ | CH₃ | N | CH₃ | CH₂OCH₃ | |
| H | CH₂OCH₃ | CH₃ | N | CH₃ | CH(OCH₃)₂ | |
| H | CH₂OCH₃ | CH₃ | N | OCH₃ | CH₂OCH₃ | |
| H | CH₂OCH₃ | CH₃ | N | OCH₃ | OCH₃ | |
| H | CH₂OCH₃ | CH₃ | N | OCH₃ | C₂H₅ | |
| H | CH₂OCH₃ | CH₃ | N | OCH₃ | NHCH₃ | |
| H | CH₂OCH₃ | CH₃ | N | OCH₃ | CH(OCH₃)₂ | |
| H | CH₂OCH₃ | CH₃ | N | OCH₂CH₃ | CH₃ | |
| H | CH₂OCH₃ | CH₃ | N | OCH₂CH₃ | OCH₃ | |
| H | CH₂OCH₃ | CH₃ | N | OCH₂CH₃ | C₂H₅ | |
| H | CH₂OCH₃ | CH₃ | N | OCH₂CH₃ | NHCH₃ | |
| H | CH₂OCH₃ | CH₃ | N | OCH₂CH₃ | CH(OCH₃)₂ | |
| H | CH₂OCH₃ | CH₃ | N | OCH₂CH₃ | CH₂OCH₃ | |
| H | CH₂OCH₃ | CH₃ | N | CH₂CF₃ | CH₃ | |
| H | CH₂OCH₃ | CH₃ | N | CH₂CF₃ | OCH₃ | |
| H | CH₂OCH₃ | CH₃ | N | CH₂CF₃ | C₂H₅ | |
| H | CH₂OCH₃ | CH₃ | N | CH₂CF₃ | NHCH₃ | |
| H | CH₂OCH₃ | CH₃ | N | CH₂CF₃ | CH₂OCH₃ | |
| H | CH₂OCH₃ | CH₃ | N | CH₂CF₃ | CH₂(OCH₃)₂ | |
| H | (CH₂)₂OCH₃ | H | CH | CH₃ | CH₃ | |
| H | (CH₂)₂OCH₃ | H | CH | CH₃ | OCH₃ | 132–135 |
| H | (CH₂)₂OCH₃ | H | CH | CH₃ | C₂H₅ | |
| H | (CH₂)₂OCH₃ | H | CH | CH₃ | NHCH₃ | |
| H | (CH₂)₂OCH₃ | H | CH | CH₃ | CH₂OCH₃ | |
| H | (CH₂)₂OCH₃ | H | CH | CH₃ | CH(OCH₃)₂ | |
| H | (CH₂)₂OCH₃ | H | CH | OCH₃ | CH₂OCH₃ | |
| H | (CH₂)₂OCH₃ | H | CH | OCH₃ | OCH₃ | 145–147 |
| H | (CH₂)₂OCH₃ | H | CH | OCH₃ | C₂H₅ | |
| H | (CH₂)₂OCH₃ | H | CH | OCH₃ | NHCH₃ | |
| H | (CH₂)₂OCH₃ | H | CH | OCH₃ | CH(OCH₃)₂ | |
| H | (CH₂)₂OCH₃ | H | CH | OCH₂CH₃ | CH₃ | |
| H | (CH₂)₂OCH₃ | H | CH | OCH₂CH₃ | OCH₃ | |
| H | (CH₂)₂OCH₃ | H | CH | OCH₂CH₃ | C₂H₅ | |
| H | (CH₂)₂OCH₃ | H | CH | OCH₂CH₃ | NHCH₃ | |
| H | (CH₂)₂OCH₃ | H | CH | OCH₂CH₃ | CH₂OCH₃ | |
| H | (CH₂)₂OCH₃ | H | CH | OCH₂CH₃ | CH(OCH₃)₂ | |
| H | (CH₂)₂OCH₃ | H | CH | Cl | OCH₃ | |
| H | (CH₂)₂OCH₃ | H | CH | Cl | NHCH₃ | |
| H | (CH₂)₂OCH₃ | H | CH | OCF₂H | CH₃ | |
| H | (CH₂)₂OCH₃ | H | CH | OCF₂H | OCH₃ | |
| H | (CH₂)₂OCH₃ | H | CH | OCF₂H | C₂H₅ | |
| H | (CH₂)₂OCH₃ | H | CH | OCF₂H | NHCH₃ | |
| H | (CH₂)₂OCH₃ | H | CH | OCF₂H | CH₂OCH₃ | |
| H | (CH₂)₂OCH₃ | H | CH | OCF₂H | CH(OCH₃)₂ | |
| H | (CH₂)₂OCH₃ | H | CH | CH₂CF₃ | CH₃ | |
| H | (CH₂)₂OCH₃ | H | CH | CH₂CF₃ | OCH₃ | |
| H | (CH₂)₂OCH₃ | H | CH | CH₂CF₃ | C₂H₅ | |
| H | (CH₂)₂OCH₃ | H | CH | CH₂CF₃ | NHCH₃ | |
| H | (CH₂)₂OCH₃ | H | CH | CH₂CF₃ | CH₂OCH₃ | |
| H | (CH₂)₂OCH₃ | H | CH | CH₂CF₃ | CH(OCH₃)₂ | |
| H | (CH₂)₂OCH₃ | H | N | CH₃ | CH₃ | |
| H | (CH₂)₂OCH₃ | H | N | CH₃ | OCH₃ | 125d |
| H | (CH₂)₂OCH₃ | H | N | CH₃ | C₂H₅ | |
| H | (CH₂)₂OCH₃ | H | N | CH₃ | NHCH₃ | |
| H | (CH₂)₂OCH₃ | H | N | CH₃ | CH₂OCH₃ | |
| H | (CH₂)₂OCH₃ | H | N | CH₃ | CH(OCH₃)₂ | |
| H | (CH₂)₂OCH₃ | H | N | OCH₃ | CH₂OCH₃ | |
| H | (CH₂)₂OCH₃ | H | N | OCH₃ | OCH₃ | 155d |
| H | (CH₂)₂OCH₃ | H | N | OCH₃ | C₂H₅ | |

TABLE 1-continued

| R₁ | Q | R | Z | X | Y | m.p. (°C.) |
|---|---|---|---|---|---|---|
| H | (CH₂)₂OCH₃ | H | N | OCH₃ | NHCH₃ | |
| H | (CH₂)₂OCH₃ | H | N | OCH₃ | CH(OCH₃)₂ | |
| H | (CH₂)₂OCH₃ | H | N | OCH₂CH₃ | CH₃ | |
| H | (CH₂)₂OCH₃ | H | N | OCH₂CH₃ | OCH₃ | |
| H | (CH₂)₂OCH₃ | H | N | OCH₂CH₃ | C₂H₅ | |
| H | (CH₂)₂OCH₃ | H | N | OCH₂CH₃ | NHCH₃ | |
| H | (CH₂)₂OCH₃ | H | N | OCH₂CH₃ | CH₂OCH₃ | |
| H | (CH₂)₂OCH₃ | H | N | OCH₂CH₃ | CH(OCH₃)₂ | |
| H | (CH₂)₂OCH₃ | H | N | CH₂CF₃ | CH₃ | |
| H | (CH₂)₂OCH₃ | H | N | CH₂CF₃ | OCH₃ | |
| H | (CH₂)₂OCH₃ | H | N | CH₂CF₃ | C₂H₅ | |
| H | (CH₂)₂OCH₃ | H | N | CH₂CF₃ | NHCH₃ | |
| H | (CH₂)₂OCH₃ | H | N | CH₂CF₃ | CH₂OCH₃ | |
| H | (CH₂)₂OCH₃ | H | N | CH₂CF₃ | CH₂(OCH₃)₂ | |
| CH₃ | (CH₂)₂OCH₃ | H | CH | CH₃ | CH₃ | |
| CH₃ | (CH₂)₂OCH₃ | H | CH | CH₃ | OCH₃ | |
| CH₃ | (CH₂)₂OCH₃ | H | CH | OCH₃ | OCH₃ | |
| CH₃ | (CH₂)₂OCH₃ | H | CH | Cl | OCH₃ | |
| CH₃ | (CH₂)₂OCH₃ | H | N | CH₃ | CH₃ | |
| CH₃ | (CH₂)₂OCH₃ | H | N | CH₃ | OCH₃ | |
| CH₃ | (CH₂)₂OCH₃ | H | N | OCH₃ | OCH₃ | |
| CH₃ | (CH₂)₂OCH₃ | H | N | OCH₂CH₃ | NHCH₃ | |
| CH₂Cl | (CH₂)₂OCH₃ | H | CH | CH₃ | CH₃ | |
| CH₂Cl | (CH₂)₂OCH₃ | H | CH | CH₃ | OCH₃ | |
| CH₂Cl | (CH₂)₂OCH₃ | H | N | CH₃ | OCH₃ | |
| CH₂Br | (CH₂)₂OCH₃ | H | CH | CH₃ | OCH₃ | |
| CH₂Br | (CH₂)₂OCH₃ | H | N | CH₃ | OCH₃ | |
| Cl | (CH₂)₂OCH₃ | H | CH | CH₃ | CH₃ | |
| Cl | (CH₂)₂OCH₃ | H | CH | CH₃ | OCH₃ | |
| Cl | (CH₂)₂OCH₃ | H | CH | OCH₃ | OCH₃ | |
| Cl | (CH₂)₂OCH₃ | H | CH | Cl | OCH₃ | |
| Cl | (CH₂)₂OCH₃ | H | N | CH₃ | CH₃ | |
| Cl | (CH₂)₂OCH₃ | H | N | CH₃ | OCH₃ | |
| Cl | (CH₂)₂OCH₃ | H | N | OCH₃ | OCH₃ | |
| Cl | (CH₂)₂OCH₃ | H | N | OCH₂CH₃ | NHCH₃ | |
| Br | (CH₂)₂OCH₃ | H | CH | CH₃ | OCH₃ | |
| Br | (CH₂)₂OCH₃ | H | N | CH₃ | OCH₃ | |
| F | (CH₂)₂OCH₃ | H | CH | CH₃ | CH₃ | |
| F | (CH₂)₂OCH₃ | H | CH | CH₃ | OCH₃ | |
| F | (CH₂)₂OCH₃ | H | CH | OCH₃ | OCH₃ | |
| F | (CH₂)₂OCH₃ | H | CH | Cl | OCH₃ | |
| F | (CH₂)₂OCH₃ | H | N | CH₃ | CH₃ | |
| F | (CH₂)₂OCH₃ | H | N | CH₃ | OCH₃ | |
| F | (CH₂)₂OCH₃ | H | N | OCH₃ | OCH₃ | |
| F | (CH₂)₂OCH₃ | H | N | OCH₂CH₃ | NHCH₃ | |
| NO₂ | (CH₂)₂OCH₃ | H | CH | CH₃ | CH₃ | |
| NO₂ | (CH₂)₂OCH₃ | H | CH | CH₃ | OCH₃ | |
| NO₂ | (CH₂)₂OCH₃ | H | CH | OCH₃ | OCH₃ | |
| NO₂ | (CH₂)₂OCH₃ | H | CH | Cl | OCH₃ | |
| NO₂ | (CH₂)₂OCH₃ | H | N | CH₃ | CH₃ | |
| NO₂ | (CH₂)₂OCH₃ | H | N | CH₃ | OCH₃ | |
| NO₂ | (CH₂)₂OCH₃ | H | N | OCH₃ | OCH₃ | |
| NO₂ | (CH₂)₂OCH₃ | H | N | OCH₂CH₃ | NHCH₃ | |
| OCH₃ | (CH₂)₂OCH₃ | H | CH | CH₃ | CH₃ | |
| OCH₃ | (CH₂)₂OCH₃ | H | CH | CH₃ | OCH₃ | |
| OCH₃ | (CH₂)₂OCH₃ | H | CH | OCH₃ | OCH₃ | |
| OCH₃ | (CH₂)₂OCH₃ | H | CH | Cl | OCH₃ | |
| OCH₃ | (CH₂)₂OCH₃ | H | N | CH₃ | CH₃ | |
| OCH₃ | (CH₂)₂OCH₃ | H | N | CH₃ | OCH₃ | |
| OCH₃ | (CH₂)₂OCH₃ | H | N | OCH₃ | OCH₃ | |
| OCH₃ | (CH₂)₂OCH₃ | H | N | OCH₂CH₃ | NHCH₃ | |
| SO₂N(CH₃)₂ | (CH₂)₂OCH₃ | H | CH | CH₃ | CH₃ | |
| SO₂N(CH₃)₂ | (CH₂)₂OCH₃ | H | CH | CH₃ | OCH₃ | |
| SO₂N(CH₃)₂ | (CH₂)₂OCH₃ | H | CH | OCH₃ | OCH₃ | |
| SO₂N(CH₃)₂ | (CH₂)₂OCH₃ | H | CH | Cl | OCH₃ | |
| SO₂N(CH₃)₂ | (CH₂)₂OCH₃ | H | N | CH₃ | CH₃ | |
| SO₂N(CH₃)₂ | (CH₂)₂OCH₃ | H | N | CH₃ | OCH₃ | |
| SO₂N(CH₃)₂ | (CH₂)₂OCH₃ | H | N | OCH₃ | OCH₃ | |
| SO₂N(CH₃)₂ | (CH₂)₂OCH₃ | H | N | OCH₂CH₃ | NHCH₃ | |
| SCH₃ | (CH₂)₂OCH₃ | H | CH | CH₃ | CH₃ | |
| SCH₃ | (CH₂)₂OCH₃ | H | CH | CH₃ | OCH₃ | |

TABLE 1-continued

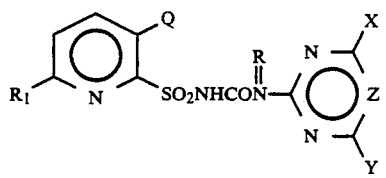

| R₁ | Q | R | Z | X | Y | m.p. (°C.) |
|---|---|---|---|---|---|---|
| SCH₃ | (CH₂)₂OCH₃ | H | CH | OCH₃ | OCH₃ | |
| SCH₃ | (CH₂)₂OCH₃ | H | CH | Cl | OCH₃ | |
| SCH₃ | (CH₂)₂OCH₃ | H | N | CH₃ | CH₃ | |
| SCH₃ | (CH₂)₂OCH₃ | H | N | CH₃ | OCH₃ | |
| SCH₃ | (CH₂)₂OCH₃ | H | N | OCH₃ | OCH₃ | |
| SCH₃ | (CH₂)₂OCH₃ | H | N | OCH₂CH₃ | NHCH₃ | |
| S(O)CH₃ | (CH₂)₂OCH₃ | H | CH | CH₃ | CH₃ | |
| S(O)CH₃ | (CH₂)₂OCH₃ | H | CH | CH₃ | OCH₃ | |
| S(O)CH₃ | (CH₂)₂OCH₃ | H | CH | OCH₃ | OCH₃ | |
| S(O)CH₃ | (CH₂)₂OCH₃ | H | CH | Cl | OCH₃ | |
| S(O)CH₃ | (CH₂)₂OCH₃ | H | N | CH₃ | CH₃ | |
| S(O)CH₃ | (CH₂)₂OCH₃ | H | N | CH₃ | OCH₃ | |
| S(O)CH₃ | (CH₂)₂OCH₃ | H | N | OCH₃ | OCH₃ | |
| S(O)CH₃ | (CH₂)₂OCH₃ | H | N | OCH₂CH₃ | NHCH₃ | |
| SO₂CH₃ | (CH₂)₂OCH₃ | H | CH | CH₃ | CH₃ | |
| SO₂CH₃ | (CH₂)₂OCH₃ | H | CH | CH₃ | OCH₃ | |
| SO₂CH₃ | (CH₂)₂OCH₃ | H | CH | OCH₃ | OCH₃ | |
| SO₂CH₃ | (CH₂)₂OCH₃ | H | CH | Cl | OCH₃ | |
| SO₂CH₃ | (CH₂)₂OCH₃ | H | N | CH₃ | CH₃ | |
| SO₂CH₃ | (CH₂)₂OCH₃ | H | N | CH₃ | OCH₃ | |
| SO₂CH₃ | (CH₂)₂OCH₃ | H | N | OCH₃ | OCH₃ | |
| SO₂CH₃ | (CH₂)₂OCH₃ | H | N | OCH₂CH₃ | NHCH₃ | |
| CO₂CH₃ | (CH₂)₂OCH₃ | H | CH | CH₃ | CH₃ | |
| CO₂CH₃ | (CH₂)₂OCH₃ | H | CH | CH₃ | OCH₃ | |
| CO₂CH₃ | (CH₂)₂OCH₃ | H | CH | OCH₃ | OCH₃ | |
| CO₂CH₃ | (CH₂)₂OCH₃ | H | CH | Cl | OCH₃ | |
| CO₂CH₃ | (CH₂)₂OCH₃ | H | N | CH₃ | CH₃ | |
| CO₂CH₃ | (CH₂)₂OCH₃ | H | N | CH₃ | OCH₃ | |
| CO₂CH₃ | (CH₂)₂OCH₃ | H | N | OCH₃ | OCH₃ | |
| CO₂CH₃ | (CH₂)₂OCH₃ | H | N | OCH₂CH₃ | NHCH₃ | |
| CO₂CH₂CH₃ | (CH₂)₂OCH₃ | H | CH | CH₃ | CH₃ | |
| CO₂CH₂CH₃ | (CH₂)₂OCH₃ | H | CH | CH₃ | OCH₃ | |
| CO₂CH₂CH₃ | (CH₂)₂OCH₃ | H | CH | OCH₃ | OCH₃ | |
| CO₂CH₂CH₃ | (CH₂)₂OCH₃ | H | CH | Cl | OCH₃ | |
| CO₂CH₂CH₃ | (CH₂)₂OCH₃ | H | N | CH₃ | CH₃ | |
| CO₂CH₂CH₃ | (CH₂)₂OCH₃ | H | N | CH₃ | OCH₃ | |
| CO₂CH₂CH₃ | (CH₂)₂OCH₃ | H | N | OCH₃ | OCH₃ | |
| CO₂CH₂CH₃ | (CH₂)₂OCH₃ | H | N | OCH₂CH₃ | NHCH₃ | |
| CO₂(CH₂)₂CH₃ | (CH₂)₂OCH₃ | H | CH | CH₃ | CH₃ | |
| CO₂(CH₂)₂CH₃ | (CH₂)₂OCH₃ | H | CH | CH₃ | OCH₃ | |
| CO₂(CH₂)₂CH₃ | (CH₂)₂OCH₃ | H | CH | OCH₃ | OCH₃ | |
| CO₂(CH₂)₂CH₃ | (CH₂)₂OCH₃ | H | CH | Cl | OCH₃ | |
| CO₂(CH₂)₂CH₃ | (CH₂)₂OCH₃ | H | N | CH₃ | CH₃ | |
| CO₂(CH₂)₂CH₃ | (CH₂)₂OCH₃ | H | N | CH₃ | OCH₃ | |
| CO₂(CH₂)₂CH₃ | (CH₂)₂OCH₃ | H | N | OCH₃ | OCH₃ | |
| CO₂(CH₂)₂CH₃ | (CH₂)₂OCH₃ | H | N | OCH₂CH₃ | NHCH₃ | |
| CO₂CH₂CH=CH₂ | (CH₂)₂OCH₃ | H | CH | CH₃ | CH₃ | |
| CO₂CH₂CH=CH₂ | (CH₂)₂OCH₃ | H | CH | CH₃ | OCH₃ | |
| CO₂CH₂CH=CH₂ | (CH₂)₂OCH₃ | H | CH | OCH₃ | OCH₃ | |
| CO₂CH₂CH=CH₂ | (CH₂)₂OCH₃ | H | CH | Cl | OCH₃ | |
| CO₂CH₂CH=CH₂ | (CH₂)₂OCH₃ | H | N | CH₃ | CH₃ | |
| CO₂CH₂CH=CH₂ | (CH₂)₂OCH₃ | H | N | CH₃ | OCH₃ | |
| CO₂CH₂CH=CH₂ | (CH₂)₂OCH₃ | H | N | OCH₃ | OCH₃ | |
| CO₂CH₂CH=CH₂ | (CH₂)₂OCH₃ | H | N | OCH₂CH₃ | NHCH₃ | |
| OCH₂Cl | (CH₂)₂OCH₃ | H | CH | CH₃ | OCH₃ | |
| OCH₂Cl | (CH₂)₂OCH₃ | H | N | CH₃ | OCH₃ | |
| SCH₂Cl | (CH₂)₂OCH₃ | H | CH | CH₃ | OCH₃ | |
| SCH₂Cl | (CH₂)₂OCH₃ | H | N | CH₃ | OCH₃ | |
| NH₂ | (CH₂)₂OCH₃ | H | CH | CH₃ | OCH₃ | |
| NH₂ | (CH₂)₂OCH₃ | H | N | CH₃ | OCH₃ | |
| NHCH₃ | (CH₂)₂OCH₃ | H | CH | CH₃ | OCH₃ | |
| NHCH₃ | (CH₂)₂OCH₃ | H | N | CH₃ | OCH₃ | |
| N(CH₃)₂ | (CH₂)₂OCH₃ | H | CH | CH₃ | CH₃ | |
| N(CH₃)₂ | (CH₂)₂OCH₃ | H | CH | CH₃ | OCH₃ | |
| N(CH₃)₂ | (CH₂)₂OCH₃ | H | CH | OCH₃ | OCH₃ | |
| N(CH₃)₂ | (CH₂)₂OCH₃ | H | CH | Cl | OCH₃ | |
| N(CH₃)₂ | (CH₂)₂OCH₃ | H | N | CH₃ | CH₃ | |
| N(CH₃)₂ | (CH₂)₂OCH₃ | H | N | CH₃ | OCH₃ | |
| N(CH₃)₂ | (CH₂)₂OCH₃ | H | N | OCH₃ | OCH₃ | |
| N(CH₃)₂ | (CH₂)₂OCH₃ | H | N | OCH₂CH₃ | NHCH₃ | |
| N(CH₃)CH₂CH₃ | (CH₂)₂OCH₃ | H | CH | CH₃ | OCH₃ | |

TABLE 1-continued

| $R_1$ | Q | R | Z | X | Y | m.p. (°C.) |
|---|---|---|---|---|---|---|
| N(CH₃)CH₂CH₃ | (CH₂)₂OCH₃ | H | N | CH₃ | OCH₃ | |
| C(O)N(CH₃)₂ | (CH₂)₂OCH₃ | H | CH | CH₃ | CH₃ | |
| C(O)N(CH₃)₂ | (CH₂)₂OCH₃ | H | CH | CH₃ | OCH₃ | |
| C(O)N(CH₃)₂ | (CH₂)₂OCH₃ | H | CH | OCH₃ | OCH₃ | |
| C(O)N(CH₃)₂ | (CH₂)₂OCH₃ | H | CH | Cl | OCH₃ | |
| C(O)N(CH₃)₂ | (CH₂)₂OCH₃ | H | N | CH₃ | CH₃ | |
| C(O)N(CH₃)₂ | (CH₂)₂OCH₃ | H | N | CH₃ | OCH₃ | |
| C(O)N(CH₃)₂ | (CH₂)₂OCH₃ | H | N | OCH₃ | OCH₃ | |
| C(O)N(CH₃)₂ | (CH₂)₂OCH₃ | H | N | OCH₂CH₃ | NHCH₃ | |
| H | CH₂OH | H | CH | CH₃ | CH₃ | |
| H | CH₂OH | H | CH | CH₃ | OCH₃ | |
| H | CH₂OH | H | CH | OCH₃ | OCH₃ | |
| H | CH₂OH | H | CH | Cl | OCH₃ | |
| H | CH₂OH | H | N | CH₃ | CH₃ | |
| H | CH₂OH | H | N | CH₃ | CH₃ | |
| H | CH₂OH | H | N | OCH₃ | OCH₃ | |
| H | CH₂OH | H | N | OCH₂CH₃ | NHCH₃ | |
| H | CH₂OH | CH₃ | N | CH₃ | OCH₃ | |
| H | CH(CH₃)OH | H | CH | CH₃ | CH₃ | 183–185 |
| H | CH(CH₃)OH | H | CH | CH₃ | OCH₃ | 153–156 |
| H | CH(CH₃)OH | H | CH | OCH₃ | OCH₃ | 135–139 |
| H | CH(CH₃)OH | H | CH | Cl | OCH₃ | 128–130 |
| H | CH(CH₃)OH | H | N | OCH₃ | OCH₃ | 142–145 |
| H | CH(OH)CH₂CH₃ | H | CH | CH₃ | CH₃ | 161–164 |
| H | CH(OH)CH₂CH₃ | H | CH | OCH₃ | OCH₃ | 133–135 |
| H | CH(OH)CH₂CH₃ | H | CH | Cl | OCH₃ | 124–127 |
| H | CH(OH)CH₂CH₃ | H | N | CH₃ | OCH₃ | 138–141 |
| H | CH(OH)CH₂CH₃ | H | N | OCH₃ | OCH₃ | 199–202 |
| H | CH(OH)CH(CH₃)₂ | H | CH | CH₃ | CH₃ | 179–181 |
| H | CH(OH)CH(CH₃)₂ | H | CH | CH₃ | OCH₃ | 140–142 |
| H | CH(OH)CH(CH₃)₂ | H | CH | OCH₃ | OCH₃ | 135–138 |
| H | CH(OH)CH(CH₃)₂ | H | CH | Cl | OCH₃ | 144–146 |
| H | CH(OH)CH(CH₃)₂ | H | N | CH₃ | OCH₃ | 129–131 |
| H | CH(OH)CH(CH₃)₂ | H | N | OCH₃ | OCH₃ | 148–150 |
| H | (CH₂)₃OCH₃ | H | CH | CH₃ | OCH₃ | 127–129 |
| H | (CH₂)₃OCH₃ | H | CH | OCH₃ | OCH₃ | 133–134 |
| H | (CH₂)₃OCH₃ | H | N | CH₃ | OCH₃ | 121–123 |
| H | (CH₂)₃OCH₃ | H | N | OCH₃ | OCH₃ | 174–181 |
| H | (CH₂)₃OCH₃ | H | CH | Cl | OCH₃ | 113–115 |
| H | (CH₂)₂OH | H | CH | CH₃ | CH₃ | |
| H | (CH₂)₂OH | H | CH | OCH₃ | CH₃ | |
| H | (CH₂)₂OH | H | CH | OCH₃ | OCH₃ | 115–119 |
| H | (CH₂)₂OH | H | CH | Cl | OCH₃ | |
| H | (CH₂)₂OH | H | N | CH₃ | CH₃ | |
| H | (CH₂)₂OH | H | N | CH₃ | OCH₃ | |
| H | (CH₂)₂OH | H | N | OCH₃ | OCH₃ | 105–112d |
| H | (CH₂)₂OH | H | N | OCH₂CH₃ | NHCH₃ | |
| H | (CH₂)₂OH | CH₃ | N | CH₃ | OCH₃ | |
| H | CH₂OCH₂CH₃ | H | CH | CH₃ | CH₃ | |
| H | CH₂OCH₂CH₃ | H | CH | CH₃ | OCH₃ | 150–153 |
| H | CH₂OCH₂CH₃ | H | CH | OCH₃ | OCH₃ | 138–143 |
| H | CH₂OCH₂CH₃ | H | CH | Cl | OCH₃ | |
| H | CH₂OCH₂CH₃ | H | N | CH₃ | CH₃ | |
| H | CH₂OCH₂CH₃ | H | N | CH₃ | OCH₃ | 141–145 |
| H | CH₂OCH₂CH₃ | H | N | OCH₃ | OCH₃ | 156–160 |
| H | CH₂OCH₂CH₃ | H | N | OCH₂CH₃ | NHCH₃ | |
| H | CH₂OCH₂CH₃ | CH₃ | N | CH₃ | OCH₃ | |
| H | (CH₂)₂OCH₂CH₃ | H | CH | CH₃ | CH₃ | |
| H | (CH₂)₂OCH₂CH₃ | H | CH | CH₃ | OCH₃ | |
| H | (CH₂)₂OCH₂CH₃ | H | CH | OCH₃ | OCH₃ | |
| H | (CH₂)₂OCH₂CH₃ | H | CH | Cl | OCH₃ | |
| H | (CH₂)₂OCH₂CH₃ | H | N | CH₃ | CH₃ | |
| H | (CH₂)₂OCH₂CH₃ | H | N | CH₃ | OCH₃ | |
| H | (CH₂)₂OCH₂CH₃ | H | N | OCH₃ | OCH₃ | |
| H | (CH₂)₂OCH₂CH₃ | H | N | OCH₂CH₃ | NHCH₃ | |
| H | (CH₂)₂OCH₂CH₃ | CH₃ | N | CH₃ | OCH₃ | |
| H | CH₂OCH₂CH=CH₂ | H | CH | CH₃ | CH₃ | |
| H | CH₂OCH₂CH=CH₂ | H | CH | CH₃ | OCH₃ | |
| H | CH₂OCH₂CH=CH₂ | H | CH | OCH₃ | OCH₃ | |
| H | CH₂OCH₂CH=CH₂ | H | CH | Cl | OCH₃ | |
| H | CH₂OCH₂CH=CH₂ | H | N | CH₃ | CH₃ | |

TABLE 1-continued

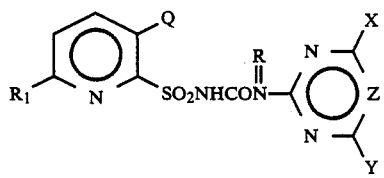

| R₁ | Q | R | Z | X | Y | m.p. (°C.) |
|---|---|---|---|---|---|---|
| H | CH₂OCH₂CH=CH₂ | H | N | CH₃ | OCH₃ | |
| H | CH₂OCH₂CH=CH₂ | H | N | OCH₃ | OCH₃ | |
| H | CH₂OCH₂CH=CH₂ | H | N | OCH₂CH₃ | NHCH₃ | |
| H | CH₂OCH₂CH=CH₂ | CH₃ | N | CH₃ | OCH₃ | |
| H | CH₂OCH₂C≡CH | H | CH | CH₃ | CH₃ | |
| H | CH₂OCH₂C≡CH | H | CH | CH₃ | OCH₃ | |
| H | CH₂OCH₂C≡CH | H | CH | OCH₃ | OCH₃ | |
| H | CH₂OCH₂C≡CH | H | CH | Cl | OCH₃ | |
| H | CH₂OCH₂C≡CH | H | N | CH₃ | CH₃ | |
| H | CH₂OCH₂C≡CH | H | N | CH₃ | OCH₃ | |
| H | CH₂OCH₂C≡CH | H | N | OCH₃ | OCH₃ | |
| H | CH₂OCH₂C≡CH | H | N | OCH₂CH₃ | NHCH₃ | |
| H | CH₂OCH₂C≡CH | CH₃ | N | CH₃ | OCH₃ | |
| H | CH₂OCH₂Cl | H | CH | CH₃ | CH₃ | |
| H | CH₂OCH₂Cl | H | CH | CH₃ | OCH₃ | |
| H | CH₂OCH₂Cl | H | CH | OCH₃ | OCH₃ | |
| H | CH₂OCH₂Cl | H | CH | Cl | OCH₃ | |
| H | CH₂OCH₂Cl | H | N | CH₃ | CH₃ | |
| H | CH₂OCH₂Cl | H | N | CH₃ | OCH₃ | |
| H | CH₂OCH₂Cl | H | N | OCH₃ | OCH₃ | |
| H | CH₂OCH₂Cl | H | N | OCH₂CH₃ | NHCH₃ | |
| H | CH₂OCH₂Cl | CH₃ | N | CH₃ | OCH₃ | |
| H | CH₂O(CH₂)₂Cl | H | CH | CH₃ | CH₃ | |
| H | CH₂O(CH₂)₂Cl | H | CH | CH₃ | OCH₃ | |
| H | CH₂O(CH₂)₂Cl | H | CH | OCH₃ | OCH₃ | |
| H | CH₂O(CH₂)₂Cl | H | CH | Cl | OCH₃ | |
| H | CH₂O(CH₂)₂Cl | H | N | CH₃ | CH₃ | |
| H | CH₂O(CH₂)₂Cl | H | N | CH₃ | OCH₃ | |
| H | CH₂O(CH₂)₂Cl | H | N | OCH₃ | OCH₃ | |
| H | CH₂O(CH₂)₂Cl | H | N | OCH₂CH₃ | NHCH₃ | |
| H | CH₂O(CH₂)₂Cl | CH₃ | N | CH₃ | OCH₃ | |
| H | CH₂OSO₂CH₃ | H | CH | CH₃ | CH₃ | |
| H | CH₂OSO₂CH₃ | H | CH | CH₃ | OCH₃ | |
| H | CH₂OSO₂CH₃ | H | CH | OCH₃ | OCH₃ | |
| H | CH₂OSO₂CH₃ | H | CH | Cl | OCH₃ | |
| H | CH₂OSO₂CH₃ | H | N | CH₃ | CH₃ | |
| H | CH₂OSO₂CH₃ | H | N | CH₃ | OCH₃ | |
| H | CH₂OSO₂CH₃ | H | N | OCH₃ | OCH₃ | |
| H | CH₂OSO₂CH₃ | H | N | OCH₂CH₃ | NHCH₃ | |
| H | CH₂OSO₂CH₃ | CH₃ | N | CH₃ | OCH₃ | |
| H | CH₂OC(O)CH₃ | H | CH | CH₃ | OCH₃ | |
| H | CH₂OC(O)CH₃ | H | CH | CH₃ | OCH₃ | |
| H | CH₂OC(O)CH₃ | H | CH | OCH₃ | OCH₃ | |
| H | CH₂OC(O)CH₃ | H | CH | Cl | OCH₃ | |
| H | CH₂OC(O)CH₃ | H | N | CH₃ | CH₃ | |
| H | CH₂OC(O)CH₃ | H | N | CH₃ | OCH₃ | |
| H | CH₂OC(O)CH₃ | H | N | OCH₃ | OCH₃ | |
| H | CH₂OC(O)CH₃ | H | N | OCH₂CH₃ | NHCH₃ | |
| H | CH₂OC(O)CH₃ | CH₃ | N | CH₃ | OCH₃ | |
| H | CH₂OC(O)CH₂CH₃ | H | CH | CH₃ | CH₃ | |
| H | CH₂OC(O)CH₂CH₃ | H | CH | CH₃ | OCH₃ | |
| H | CH₂OC(O)CH₂CH₃ | H | CH | OCH₃ | OCH₃ | |
| H | CH₂OC(O)CH₂CH₃ | H | CH | Cl | OCH₃ | |
| H | CH₂OC(O)CH₂CH₃ | H | N | CH₃ | CH₃ | |
| H | CH₂OC(O)CH₂CH₃ | H | N | CH₃ | OCH₃ | |
| H | CH₂OC(O)CH₂CH₃ | H | N | OCH₃ | OCH₃ | |
| H | CH₂OC(O)CH₂CH₃ | H | N | OCH₂CH₃ | NHCH₃ | |
| H | CH₂OC(O)CH₂CH₃ | CH₃ | N | CH₃ | OCH₃ | |
| H | CH₂SCH₃ | H | CH | CH₃ | CH₃ | 177–179° |
| H | CH₂SCH₃ | H | CH | CH₃ | OCH₃ | 130–133° |
| H | CH₂SCH₃ | H | CH | OCH₃ | OCH₃ | 145–147° |
| H | CH₂SCH₃ | H | CH | Cl | OCH₃ | 135–137° |
| H | CH₂SCH₃ | H | N | CH₃ | CH₃ | |
| H | CH₂SCH₃ | H | N | CH₃ | OCH₃ | |
| H | CH₂SCH₃ | H | N | OCH₃ | OCH₃ | |
| H | CH₂SCH₃ | H | N | OCH₂CH₃ | NHCH₃ | |
| H | CH₂SCH₃ | CH₃ | N | CH₃ | OCH₃ | |
| Cl | CH₂OCH₂CH₃ | H | CH | CH₃ | CH₃ | |
| Cl | CH₂OCH₂CH₃ | H | CH | CH₃ | OCH₃ | |
| Cl | CH₂OCH₂CH₃ | H | CH | OCH₃ | OCH₃ | |
| Cl | CH₂OCH₂CH₃ | H | CH | Cl | OCH₃ | |

TABLE 1-continued

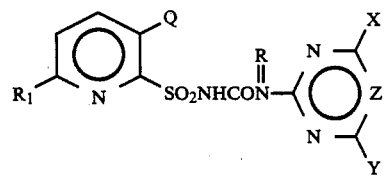

| R₁ | Q | R | Z | X | Y | m.p. (°C.) |
|---|---|---|---|---|---|---|
| Cl | CH₂OCH₂CH₃ | H | N | CH₃ | CH₃ | |
| Cl | CH₂OCH₂CH₃ | H | N | CH₃ | OCH₃ | |
| Cl | CH₂OCH₂CH₃ | H | N | OCH₃ | OCH₃ | |
| Cl | CH₂OCH₂CH₃ | H | N | OCH₂CH₃ | NHCH₃ | |
| Cl | CH₂OCH₂CH₃ | CH₃ | N | CH₃ | OCH₃ | |
| SCH₃ | CH₂SCH₃ | H | CH | CH₃ | OCH₃ | |
| SCH₃ | CH₂SCH₃ | H | N | CH₃ | OCH₃ | |
| CO₂CH₃ | CH₂SCH₃ | H | CH | CH₃ | CH₃ | |
| CO₂CH₃ | CH₂SCH₃ | H | CH | CH₃ | OCH₃ | |
| CO₂CH₃ | CH₂SCH₃ | H | CH | OCH₃ | OCH₃ | |
| CO₂CH₃ | CH₂SCH₃ | H | CH | Cl | OCH₃ | |
| CO₂CH₃ | CH₂SCH₃ | H | N | CH₃ | CH₃ | |
| CO₂CH₃ | CH₂SCH₃ | H | N | CH₃ | OCH₃ | |
| CO₂CH₃ | CH₂SCH₃ | H | N | OCH₃ | OCH₃ | |
| CO₂CH₃ | CH₂SCH₃ | H | N | OCH₂CH₃ | NHCH₃ | |
| CO₂CH₃ | CH₂SCH₃ | CH₃ | N | CH₃ | OCH₃ | |
| CO₂N(CH₃)₂ | CH₂SCH₃ | H | CH | CH₃ | OCH₃ | |
| CO₂N(CH₃)₂ | CH₂SCH₃ | H | N | CH₃ | OCH₃ | |
| H | (CH₂)₂SCH₃ | H | CH | CH₃ | CH₃ | |
| H | (CH₂)₂SCH₃ | H | CH | CH₃ | OCH₃ | 119–125 |
| H | (CH₂)₂SCH₃ | H | CH | OCH₃ | OCH₃ | 103–107 |
| H | (CH₂)₂SCH₃ | H | CH | Cl | OCH₃ | |
| H | (CH₂)₂SCH₃ | H | N | CH₃ | CH₃ | |
| H | (CH₂)₂SCH₃ | H | N | CH₃ | OCH₃ | 111d |
| H | (CH₂)₂SCH₃ | H | N | OCH₃ | OCH₃ | 119–122 |
| H | (CH₂)₂SCH₃ | H | N | OCH₂CH₃ | NHCH₃ | |
| H | (CH₂)₂SCH₃ | CH₃ | N | CH₃ | OCH₃ | |
| Cl | (CH₂)₂SCH₃ | H | CH | CH₃ | OCH₃ | |
| Cl | (CH₂)₂SCH₃ | H | N | CH₃ | OCH₃ | |
| SCH₃ | (CH₂)₂SCH₃ | H | CH | CH₃ | OCH₃ | |
| SCH₃ | (CH₂)₂SCH₃ | H | N | CH₃ | OCH₃ | |
| CO₂CH₃ | (CH₂)₂SCH₃ | H | CH | CH₃ | CH₃ | |
| CO₂CH₃ | (CH₂)₂SCH₃ | H | CH | CH₃ | OCH₃ | |
| CO₂CH₃ | (CH₂)₂SCH₃ | H | CH | OCH₃ | OCH₃ | |
| CO₂CH₃ | (CH₂)₂SCH₃ | H | CH | Cl | OCH₃ | |
| CO₂CH₃ | (CH₂)₂SCH₃ | H | N | CH₃ | CH₃ | |
| CO₂CH₃ | (CH₂)₂SCH₃ | H | N | CH₃ | OCH₃ | |
| CO₂CH₃ | (CH₂)₂SCH₃ | H | N | OCH₃ | OCH₃ | |
| CO₂CH₃ | (CH₂)₂SCH₃ | H | N | OCH₂CH₃ | NHCH₃ | |
| CO₂CH₃ | (CH₂)₂SCH₃ | CH₃ | N | CH₃ | OCH₃ | |
| CON(CH₃)₂ | (CH₂)₂SCH₃ | H | CH | CH₃ | OCH₃ | |
| CON(CH₃)₂ | (CH₂)₂SCH₃ | H | N | CH₃ | OCH₃ | |
| H | CH₂SH | H | CH | CH₃ | CH₃ | |
| H | CH₂SH | H | CH | CH₃ | OCH₃ | |
| H | CH₂SH | H | CH | OCH₃ | OCH₃ | |
| H | CH₂SH | H | CH | Cl | OCH₃ | |
| H | CH₂SH | H | N | CH₃ | CH₃ | |
| H | CH₂SH | H | N | CH₃ | OCH₃ | |
| H | CH₂SH | H | N | OCH₃ | OCH₃ | |
| H | CH₂SH | H | N | OCH₂CH₃ | NHCH₃ | |
| H | CH₂SH | CH₃ | N | CH₃ | OCH₃ | |
| H | CH₂SCH₂CH₂CH₃ | H | CH | CH₃ | OCH₃ | 116–120 |
| H | CH₂SCH₂CH₂CH₃ | H | CH | OCH₃ | OCH₃ | 111–114 |
| H | CH₂SCH₂CH₂CH₃ | H | CH | Cl | OCH₃ | 108–112 |
| H | CH₂SCH₂CH₂CH₃ | H | N | CH₃ | CH₃ | 152–156 |
| H | CH₂SCH₂CH₂CH₃ | H | N | CH₃ | OCH₃ | 122–125d |
| H | CH₂SCH₂CH=CH₂ | H | CH | CH₃ | CH₃ | |
| H | CH₂SCH₂CH=CH₂ | H | CH | CH₃ | OCH₃ | |
| H | CH₂SCH₂CH=CH₂ | H | CH | OCH₃ | OCH₃ | |
| H | CH₂SCH₂CH=CH₂ | H | CH | Cl | OCH₃ | |
| H | CH₂SCH₂CH=CH₂ | H | N | CH₃ | CH₃ | |
| H | CH₂SCH₂CH=CH₂ | H | N | CH₃ | OCH₃ | |
| H | CH₂SCH₂CH=CH₂ | H | N | OCH₃ | OCH₃ | |
| H | CH₂SCH₂CH=CH₂ | H | N | OCH₂CH₃ | NHCH₃ | |
| H | CH₂SCH₂CH=CH₂ | CH₃ | N | CH₃ | OCH₃ | |
| H | CH₂SCH₂C≡CH | H | CH | CH₃ | CH₃ | |
| H | CH₂SCH₂C≡CH | H | CH | CH₃ | OCH₃ | |
| H | CH₂SCH₂C≡CH | H | CH | OCH₃ | OCH₃ | |
| H | CH₂SCH₂C≡CH | H | CH | Cl | OCH₃ | |
| H | CH₂SCH₂C≡CH | H | N | CH₃ | CH₃ | |
| H | CH₂SCH₂C≡CH | H | N | CH₃ | OCH₃ | |

TABLE 1-continued

Structure: pyridine with $R_1$ at 6-position, Q at 3-position, $SO_2NHCON(R)=$ linked to pyrimidine/triazine ring with X, Y, Z substituents.

| $R_1$ | Q | R | Z | X | Y | m.p. (°C.) |
|---|---|---|---|---|---|---|
| H | CH₂SCH₂C≡CH | H | N | OCH₃ | OCH₃ | |
| H | CH₂SCH₂C≡CH | H | N | OCH₂CH₃ | NHCH₃ | |
| H | CH₂SCH₂C≡CH | CH₃ | N | CH₃ | OCH₃ | |
| H | CH₂SCH₂CH₃ | H | CH | CH₃ | CH₃ | 135–140 |
| H | CH₂SCH₂CH₃ | H | CH | CH₃ | OCH₃ | 117–120 |
| H | CH₂SCH₂CH₃ | H | CH | OCH₃ | OCH₃ | 121–125 |
| H | CH₂SCH₂CH₃ | H | CH | Cl | OCH₃ | 105–110 |
| H | CH₂SCH₂CH₃ | H | N | CH₃ | CH₃ | |
| H | CH₂SCH₂CH₃ | H | N | CH₃ | OCH₃ | 225–235d |
| H | CH₂SCH₂CH₃ | H | N | OCH₃ | OCH₃ | |
| H | CH₂SCH₂CH₃ | H | N | OCH₂CH₃ | NHCH₃ | |
| H | CH₂SCH₂CH₃ | CH₃ | N | CH₃ | OCH₃ | |
| H | CH(CH₃)SCH₃ | H | CH | CH₃ | CH₃ | 170–173 |
| H | CH(CH₃)SCH₃ | H | CH | CH₃ | OCH₃ | 146–148 |
| H | CH(CH₃)SCH₃ | H | CH | OCH₃ | OCH₃ | 145–150 |
| H | CH(CH₃)SCH₃ | H | CH | Cl | OCH₃ | 155–158 |
| H | CH(CH₃)SCH₃ | H | N | CH₃ | OCH₃ | 139–142 |
| H | CH(CH₃)SCH₃ | H | N | OCH₃ | OCH₃ | 135–138 |
| H | CH₂SCH₂Cl | H | CH | CH₃ | OCH₃ | |
| H | CH₂S(CH₂)₂Cl | H | CH | CH₃ | OCH₃ | |
| H | CH₂SCO₂CH₃ | H | CH | CH₃ | OCH₃ | |
| H | CH₂SCO₂CH₃ | H | N | CH₃ | OCH₃ | |
| H | CH₂SCO₂CH₂CH₃ | H | CH | CH₃ | OCH₃ | |
| H | CH₂SCO₂CH₂CH₃ | H | N | CH₃ | OCH₃ | |
| H | CH₂S(O)CH₃ | H | CH | CH₃ | CH₃ | |
| H | CH₂S(O)CH₃ | H | CH | CH₃ | OCH₃ | |
| H | CH₂S(O)CH₃ | H | CH | OCH₃ | OCH₃ | |
| H | CH₂S(O)CH₃ | H | CH | Cl | OCH₃ | |
| H | CH₂S(O)CH₃ | H | N | CH₃ | CH₃ | |
| H | CH₂S(O)CH₃ | H | N | CH₃ | OCH₃ | |
| H | CH₂S(O)CH₃ | H | N | OCH₃ | OCH₃ | |
| H | CH₂S(O)CH₃ | H | N | OCH₂CH₃ | NHCH₃ | |
| H | CH₂S(O)CH₃ | CH₃ | N | CH₃ | OCH₃ | |
| H | CH₂CH₂S(O)CH₃ | H | CH | CH₃ | CH₃ | |
| H | CH₂CH₂S(O)CH₃ | H | CH | CH₃ | OCH₃ | |
| H | CH₂CH₂S(O)CH₃ | H | CH | OCH₃ | OCH₃ | |
| H | CH₂CH₂S(O)CH₃ | H | CH | Cl | OCH₃ | |
| H | CH₂CH₂S(O)CH₃ | H | N | CH₃ | CH₃ | |
| H | CH₂CH₂S(O)CH₃ | H | N | CH₃ | OCH₃ | |
| H | CH₂CH₂S(O)CH₃ | H | N | OCH₃ | OCH₃ | |
| H | CH₂CH₂S(O)CH₃ | H | N | OCH₂CH₃ | NHCH₃ | |
| H | CH₂CH₂S(O)CH₃ | CH₃ | N | CH₃ | OCH₃ | |
| Cl | CH₂S(O)CH₃ | H | CH | CH₃ | OCH₃ | |
| Cl | CH₂S(O)CH₃ | H | N | CH₃ | OCH₃ | |
| SCH₃ | CH₂S(O)CH₃ | H | CH | CH₃ | OCH₃ | |
| SCH₃ | CH₂S(O)CH₃ | H | N | CH₃ | OCH₃ | |
| CO₂CH₃ | CH₂S(O)CH₃ | H | CH | CH₃ | CH₃ | |
| CO₂CH₃ | CH₂S(O)CH₃ | H | CH | CH₃ | OCH₃ | |
| CO₂CH₃ | CH₂S(O)CH₃ | H | CH | OCH₃ | OCH₃ | |
| CO₂CH₃ | CH₂S(O)CH₃ | H | CH | Cl | OCH₃ | |
| CO₂CH₃ | CH₂S(O)CH₃ | H | N | CH₃ | CH₃ | |
| CO₂CH₃ | CH₂S(O)CH₃ | H | N | CH₃ | OCH₃ | |
| CO₂CH₃ | CH₂S(O)CH₃ | H | N | OCH₃ | OCH₃ | |
| CO₂CH₃ | CH₂S(O)CH₃ | H | N | OCH₂CH₃ | NHCH₃ | |
| CO₂CH₃ | CH₂S(O)CH₃ | CH₃ | N | CH₃ | OCH₃ | |
| CON(CH₃)₂ | CH₂S(O)CH₃ | H | CH | CH₃ | OCH₃ | |
| CON(CH₃)₂ | CH₂S(O)CH₃ | H | N | CH₃ | OCH₃ | |
| H | CH₂S(O)CH₂CH₃ | H | CH | CH₃ | CH₃ | |
| H | CH₂S(O)CH₂CH₃ | H | CH | CH₃ | OCH₃ | |
| H | CH₂S(O)CH₂CH₃ | H | CH | OCH₃ | OCH₃ | |
| H | CH₂S(O)CH₂CH₃ | H | CH | Cl | OCH₃ | |
| H | CH₂S(O)CH₂CH₃ | H | N | CH₃ | CH₃ | |
| H | CH₂S(O)CH₂CH₃ | H | N | CH₃ | OCH₃ | |
| H | CH₂S(O)CH₂CH₃ | H | N | OCH₃ | OCH₃ | |
| H | CH₂S(O)CH₂CH₃ | H | N | OCH₂CH₃ | NHCH₃ | |
| H | CH₂S(O)CH₂CH₃ | CH₃ | N | CH₃ | OCH₃ | |
| H | CH₂S(O)CH₂CH=CH₂ | H | CH | CH₃ | CH₃ | |
| H | CH₂S(O)CH₂CH=CH₂ | H | CH | CH₃ | OCH₃ | |
| H | CH₂S(O)CH₂CH=CH₂ | H | CH | OCH₃ | OCH₃ | |
| H | CH₂S(O)CH₂CH=CH₂ | H | CH | Cl | OCH₃ | |
| H | CH₂S(O)CH₂CH=CH₂ | H | N | CH₃ | CH₃ | |

TABLE 1-continued

Structure: pyridine with R₁ at 6-position, Q at 3-position, SO₂NHCON(R)= linked to pyrimidine/triazine ring with X, Z, Y substituents.

| R₁ | Q | R | Z | X | Y | m.p. (°C.) |
|---|---|---|---|---|---|---|
| H | CH₂S(O)CH₂CH=CH₂ | H | N | CH₃ | OCH₃ | |
| H | CH₂S(O)CH₂CH=CH₂ | H | N | OCH₃ | OCH₃ | |
| H | CH₂S(O)CH₂CH=CH₂ | H | N | OCH₂CH₃ | NHCH₃ | |
| H | CH₂S(O)CH₂CH=CH₂ | CH₃ | N | CH₃ | OCH₃ | |
| H | CH₂S(O)CH₂C≡CH | H | CH | CH₃ | CH₃ | |
| H | CH₂S(O)CH₂C≡CH | H | CH | CH₃ | OCH₃ | |
| H | CH₂S(O)CH₂C≡CH | H | CH | OCH₃ | OCH₃ | |
| H | CH₂S(O)CH₂C≡CH | H | CH | Cl | OCH₃ | |
| H | CH₂S(O)CH₂C≡CH | H | N | CH₃ | CH₃ | |
| H | CH₂S(O)CH₂C≡CH | H | N | CH₃ | OCH₃ | |
| H | CH₂S(O)CH₂C≡CH | H | N | OCH₃ | OCH₃ | |
| H | CH₂S(O)CH₂C≡CH | H | N | OCH₂CH₃ | NHCH₃ | |
| H | CH₂S(O)CH₂C≡CH | CH₃ | N | CH₃ | OCH₃ | |
| H | CH₂S(O)CH₂Cl | H | CH | CH₃ | OCH₃ | |
| H | CH₂S(O)CH₂Cl | H | N | OCH₃ | OCH₃ | |
| H | CH₂S(O)(CH₂)₂Cl | H | CH | CH₃ | OCH₃ | |
| H | CH₂S(O)(CH₂)₂Cl | H | N | CH₃ | OCH₃ | |
| H | CH₂SO₂CH₃ | H | CH | CH₃ | CH₃ | 171–174° |
| H | CH₂SO₂CH₃ | H | CH | CH₃ | OCH₃ | 121–125° |
| H | CH₂SO₂CH₃ | H | CH | OCH₃ | OCH₃ | 180–182° |
| H | CH₂SO₂CH₃ | H | CH | Cl | OCH₃ | 175–179° |
| H | CH₂SO₂CH₃ | H | N | CH₃ | CH₃ | |
| H | CH₂SO₂CH₃ | H | N | CH₃ | OCH₃ | |
| H | CH₂SO₂CH₃ | H | N | OCH₃ | OCH₃ | |
| H | CH₂SO₂CH₃ | H | N | OCH₂CH₃ | NHCH₃ | |
| H | CH₂SO₂CH₃ | CH₃ | N | CH₃ | OCH₃ | |
| H | CH(CH₃)SO₂CH₃ | H | CH | OCH₃ | OCH₃ | 153–157 |
| H | (CH₂)₂SO₂CH₃ | H | CH | CH₃ | CH₃ | |
| H | (CH₂)₂SO₂CH₃ | H | CH | CH₃ | OCH₃ | |
| H | (CH₂)₂SO₂CH₃ | H | CH | OCH₃ | OCH₃ | |
| H | (CH₂)₂SO₂CH₃ | H | CH | Cl | OCH₃ | |
| H | (CH₂)₂SO₂CH₃ | H | N | CH₃ | CH₃ | |
| H | (CH₂)₂SO₂CH₃ | H | N | CH₃ | OCH₃ | |
| H | (CH₂)₂SO₂CH₃ | H | N | OCH₃ | OCH₃ | |
| H | (CH₂)₂SO₂CH₃ | H | N | OCH₂CH₃ | NHCH₃ | |
| H | (CH₂)₂SO₂CH₃ | CH₃ | N | CH₃ | OCH₃ | |
| Cl | CH₂SO₂CH₃ | H | CH | CH₃ | OCH₃ | |
| Cl | CH₂SO₂CH₃ | H | N | CH₃ | OCH₃ | |
| SCH₃ | CH₂SO₂CH₃ | H | CH | CH₃ | OCH₃ | |
| SCH₃ | CH₂SO₂CH₃ | H | N | CH₃ | OCH₃ | |
| CO₂CH₃ | CH₂SO₂CH₃ | H | CH | CH₃ | CH₃ | |
| CO₂CH₃ | CH₂SO₂CH₃ | H | CH | CH₃ | OCH₃ | |
| CO₂CH₃ | CH₂SO₂CH₃ | H | CH | OCH₃ | OCH₃ | |
| CO₂CH₃ | CH₂SO₂CH₃ | H | CH | Cl | OCH₃ | |
| CO₂CH₃ | CH₂SO₂CH₃ | H | N | CH₃ | CH₃ | |
| CO₂CH₃ | CH₂SO₂CH₃ | H | N | CH₃ | OCH₃ | |
| CO₂CH₃ | CH₂SO₂CH₃ | H | N | OCH₃ | OCH₃ | |
| CO₂CH₃ | CH₂SO₂CH₃ | H | N | OCH₂CH₃ | NHCH₃ | |
| CO₂CH₃ | CH₂SO₂CH₃ | CH₃ | N | CH₃ | OCH₃ | |
| CON(CH₃)₂ | CH₂SO₂CH₃ | H | CH | CH₃ | OCH₃ | |
| CON(CH₃)₂ | CH₂SO₂CH₃ | H | N | CH₃ | OCH₃ | |
| H | CH₂SO₂CH₂CH₃ | H | CH | CH₃ | CH₃ | |
| H | CH₂SO₂CH₂CH₃ | H | CH | CH₃ | OCH₃ | |
| H | CH₂SO₂CH₂CH₃ | H | CH | OCH₃ | OCH₃ | |
| H | CH₂SO₂CH₂CH₃ | H | CH | Cl | OCH₃ | |
| H | CH₂SO₂CH₂CH₃ | H | N | CH₃ | CH₃ | |
| H | CH₂SO₂CH₂CH₃ | H | N | CH₃ | OCH₃ | |
| H | CH₂SO₂CH₂CH₃ | H | N | OCH₃ | OCH₃ | |
| H | CH₂SO₂CH₂CH₃ | H | N | OCH₂CH₃ | NHCH₃ | |
| H | CH₂SO₂CH₂CH₃ | CH₃ | N | CH₃ | OCH₃ | |
| H | CH₂SO₂CH₂CH₂CH₃ | H | CH | CH₃ | OCH₃ | 174–177 |
| H | CH₂SO₂CH₂CH₂CH₃ | H | CH | OCH₃ | OCH₃ | 190–193 |
| H | CH₂SO₂CH₂CH₂CH₃ | H | N | CH₃ | OCH₃ | 150–153 |
| H | CH₂SO₂CH₂CH₂CH₃ | H | N | OCH₃ | OCH₃ | 146–148d |
| H | CH₂SO₂CH₂CH=CH₂ | H | CH | CH₃ | CH₃ | |
| H | CH₂SO₂CH₂CH=CH₂ | H | CH | CH₃ | OCH₃ | |
| H | CH₂SO₂CH₂CH=CH₂ | H | CH | OCH₃ | OCH₃ | |
| H | CH₂SO₂CH₂CH=CH₂ | H | CH | Cl | OCH₃ | |
| H | CH₂SO₂CH₂CH=CH₂ | H | N | CH₃ | CH₃ | |
| H | CH₂SO₂CH₂CH=CH₂ | H | N | CH₃ | OCH₃ | |
| H | CH₂SO₂CH₂CH=CH₂ | H | N | OCH₃ | OCH₃ | |

TABLE 1-continued

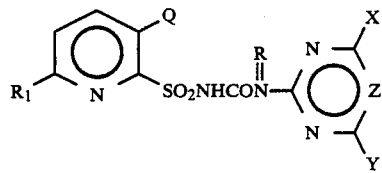

| R₁ | Q | R | Z | X | Y | m.p. (°C.) |
|---|---|---|---|---|---|---|
| H | CH₂SO₂CH₂CH=CH₂ | H | N | OCH₂CH₃ | NHCH₃ | |
| H | CH₂SO₂CH₂CH=CH₂ | CH₃ | N | CH₃ | OCH₃ | |
| H | CH₂SO₂CH₂C≡CH | H | CH | CH₃ | CH₃ | |
| H | CH₂SO₂CH₂C≡CH | H | CH | CH₃ | OCH₃ | |
| H | CH₂SO₂CH₂C≡CH | H | CH | OCH₃ | OCH₃ | |
| H | CH₂SO₂CH₂C≡CH | H | CH | Cl | OCH₃ | |
| H | CH₂SO₂CH₂C≡CH | H | N | CH₃ | CH₃ | |
| H | CH₂SO₂CH₂C≡CH | H | N | CH₃ | OCH₃ | |
| H | CH₂SO₂CH₂C≡CH | H | N | OCH₃ | OCH₃ | |
| H | CH₂SO₂CH₂C≡CH | H | N | OCH₂CH₃ | NHCH₃ | |
| H | CH₂SO₂CH₂C≡CH | CH₃ | N | CH₃ | OCH₃ | |
| H | CH₂SO₂CH₂Cl | H | CH | CH₃ | OCH₃ | |
| H | CH₂SO₂CH₂Cl | H | N | CH₃ | OCH₃ | |
| H | CH₂SO₂(CH₂)₂Cl | H | CH | CH₃ | OCH₃ | |
| H | CH₂SO₂(CH₂)₂Cl | H | N | CH₃ | OCH₃ | |
| H | CH₂CO₂CH₃ | H | CH | CH₃ | CH₃ | |
| H | CH₂CO₂CH₃ | H | CH | CH₃ | OCH₃ | 154–156.6 |
| H | CH₂CO₂CH₃ | H | CH | OCH₃ | OCH₃ | 167–169 |
| H | CH₂CO₂CH₃ | H | CH | Cl | OCH₃ | 159–161.5 |
| H | CH₂CO₂CH₃ | H | N | CH₃ | CH₃ | |
| H | CH₂CO₂CH₃ | H | N | CH₃ | OCH₃ | 143–147 |
| H | CH₂CO₂CH₃ | H | N | OCH₃ | OCH₃ | 134–139 |
| H | CH₂CO₂CH₃ | H | N | OCH₂CH₃ | NHCH₃ | |
| H | CH₂CO₂CH₃ | CH₃ | N | CH₃ | OCH₃ | |
| H | (CH₂)₂CO₂CH₃ | H | CH | CH₃ | CH₃ | |
| H | (CH₂)₂CO₂CH₃ | H | CH | CH₃ | OCH₃ | |
| H | (CH₂)₂CO₂CH₃ | H | CH | OCH₃ | OCH₃ | |
| H | (CH₂)₂CO₂CH₃ | H | CH | Cl | OCH₃ | |
| H | (CH₂)₂CO₂CH₃ | H | N | CH₃ | CH₃ | |
| H | (CH₂)₂CO₂CH₃ | H | N | CH₃ | OCH₃ | |
| H | (CH₂)₂CO₂CH₃ | H | N | OCH₃ | OCH₃ | |
| H | (CH₂)₂CO₂CH₃ | H | N | OCH₂CH₃ | NHCH₃ | |
| H | (CH₂)₂CO₂CH₃ | CH₃ | N | CH₃ | OCH₃ | |
| Cl | CH₂CO₂CH₃ | H | CH | CH₃ | OCH₃ | |
| Cl | CH₂CO₂CH₃ | H | N | CH₃ | OCH₃ | |
| SCH₃ | CH₂CO₂CH₃ | H | CH | CH₃ | OCH₃ | |
| SCH₃ | CH₂CO₂CH₃ | H | N | CH₃ | OCH₃ | |
| CO₂CH₃ | CH₂CO₂CH₃ | H | CH | CH₃ | CH₃ | |
| CO₂CH₃ | CH₂CO₂CH₃ | H | CH | CH₃ | OCH₃ | |
| CO₂CH₃ | CH₂CO₂CH₃ | H | CH | OCH₃ | OCH₃ | |
| CO₂CH₃ | CH₂CO₂CH₃ | H | CH | Cl | OCH₃ | |
| CO₂CH₃ | CH₂CO₂CH₃ | H | N | CH₃ | CH₃ | |
| CO₂CH₃ | CH₂CO₂CH₃ | H | N | CH₃ | OCH₃ | |
| CO₂CH₃ | CH₂CO₂CH₃ | H | N | OCH₃ | OCH₃ | |
| CO₂CH₃ | CH₂CO₂CH₃ | H | N | OCH₂CH₃ | NHCH₃ | |
| H | CO₂CH₃CH₂CO₂CH₃ | CH₃ | N | CH₃ | OCH₃ | |
| H | CON(CH₃)₂CH₂CO₂CH₃ | H | CH | CH₃ | OCH₃ | |
| H | CON(CH₃)₂CH₂CO₂CH₃ | H | N | CH₃ | OCH₃ | |
| H | CH₂CO₂CH₂CH₃ | H | CH | CH₃ | CH₃ | |
| H | CH₂CO₂CH₂CH₃ | H | CH | CH₃ | OCH₃ | |
| H | CH₂CO₂CH₂CH₃ | H | CH | OCH₃ | OCH₃ | |
| H | CH₂CO₂CH₂CH₃ | H | CH | Cl | OCH₃ | |
| H | CH₂CO₂CH₂CH₃ | H | N | CH₃ | CH₃ | |
| H | CH₂CO₂CH₂CH₃ | H | N | CH₃ | OCH₃ | |
| H | CH₂CO₂CH₂CH₃ | H | N | OCH₃ | OCH₃ | |
| H | CH₂CO₂CH₂CH₃ | H | N | OCH₂CH₃ | NHCH₃ | |
| H | CH₂CO₂CH₂CH₃ | CH₃ | N | CH₃ | OCH₃ | |
| H | CH₂CO₂CH₂CH=CH₂ | H | CH | CH₃ | CH₃ | |
| H | CH₂CO₂CH₂CH=CH₂ | H | CH | CH₃ | OCH₃ | |
| H | CH₂CO₂CH₂CH=CH₂ | H | CH | OCH₃ | OCH₃ | |
| H | CH₂CO₂CH₂CH=CH₂ | H | CH | Cl | OCH₃ | |
| H | CH₂CO₂CH₂CH=CH₂ | H | N | CH₃ | CH₃ | |
| H | CH₂CO₂CH₂CH=CH₂ | H | N | CH₃ | OCH₃ | |
| H | CH₂CO₂CH₂CH=CH₂ | H | N | OCH₃ | OCH₃ | |
| H | CH₂CO₂CH₂CH=CH₂ | H | N | OCH₂CH₃ | NHCH₃ | |
| H | CH₂CO₂CH₂CH=CH₂ | CH₃ | N | CH₃ | OCH₃ | |
| H | CH₂CO₂CH₂C≡CH | H | CH | CH₃ | CH₃ | |
| H | CH₂CO₂CH₂C≡CH | H | CH | CH₃ | OCH₃ | |
| H | CH₂CO₂CH₂C≡CH | H | CH | OCH₃ | OCH₃ | |
| H | CH₂CO₂CH₂C≡CH | H | CH | Cl | OCH₃ | |
| H | CH₂CO₂CH₂C≡CH | H | N | CH₃ | CH₃ | |

TABLE 1-continued

| R₁ | Q | R | Z | X | Y | m.p. (°C.) |
|---|---|---|---|---|---|---|
| H | CH₂CO₂CH₂C≡CH | H | N | CH₃ | OCH₃ | |
| H | CH₂CO₂CH₂C≡CH | H | N | OCH₃ | OCH₃ | |
| H | CH₂CO₂CH₂C≡CH | H | N | OCH₂CH₃ | NHCH₃ | |
| H | CH₂CO₂CH₂C≡CH | CH₃ | N | CH₃ | OCH₃ | |
| H | CH₂CO₂(CH₂)₂OCH₃ | H | CH | CH₃ | CH₃ | |
| H | CH₂CO₂(CH₂)₂OCH₃ | H | CH | CH₃ | OCH₃ | |
| H | CH₂CO₂(CH₂)₂OCH₃ | H | CH | OCH₃ | OCH₃ | |
| H | CH₂CO₂(CH₂)₂OCH₃ | H | CH | Cl | OCH₃ | |
| H | CH₂CO₂(CH₂)₂OCH₃ | H | N | CH₃ | CH₃ | |
| H | CH₂CO₂(CH₂)₂OCH₃ | H | N | CH₃ | OCH₃ | |
| H | CH₂CO₂(CH₂)₂OCH₃ | H | N | OCH₃ | OCH₃ | |
| H | CH₂CO₂(CH₂)₂OCH₃ | H | N | OCH₂CH₃ | NHCH₃ | |
| H | CH₂CO₂(CH₂)₂OCH₃ | CH₃ | N | CH₃ | OCH₃ | |
| H | CH₂CO₂(CH₂)₂Cl | H | CH | CH₃ | OCH₃ | |
| H | CH₂CO₂(CH₂)₂Cl | H | N | CH₃ | OCH₃ | |
| H | CH₂C(O)NHCH₃ | H | CH | CH₃ | OCH₃ | |
| H | CH₂C(O)NHCH₃ | H | N | CH₃ | OCH₃ | |
| H | (CH₂)₂C(O)NHCH₃ | H | CH | CH₃ | OCH₃ | |
| H | (CH₂)₂C(O)NHCH₃ | H | N | CH₃ | OCH₃ | |
| H | CH₂C(O)N(CH₃)₂ | H | CH | CH₃ | CH₃ | |
| H | CH₂C(O)N(CH₃)₂ | H | CH | CH₃ | OCH₃ | |
| H | CH₂C(O)N(CH₃)₂ | H | CH | OCH₃ | OCH₃ | 172–173 |
| H | CH₂C(O)N(CH₃)₂ | H | CH | Cl | OCH₃ | |
| H | CH₂C(O)N(CH₃)₂ | H | N | CH₃ | CH₃ | |
| H | CH₂C(O)N(CH₃)₂ | H | N | CH₃ | OCH₃ | |
| H | CH₂C(O)N(CH₃)₂ | H | N | OCH₃ | OCH₃ | 99–100 |
| H | CH₂C(O)N(CH₃)₂ | H | N | OCH₂CH₃ | NHCH₃ | |
| H | CH₂C(O)N(CH₃)₂ | CH₃ | N | CH₃ | OCH₃ | |
| H | CH₂C(O)N(CH₃)₂ | H | CH | CH₃ | CH₃ | |
| H | CH₂C(O)N(CH₃)₂ | H | CH | CH₃ | OCH₃ | |
| H | CH₂C(O)N(CH₃)₂ | H | CH | OCH₃ | OCH₃ | |
| H | CH₂C(O)N(CH₃)₂ | H | CH | Cl | OCH₃ | |
| H | CH₂C(O)N(CH₃)₂ | H | N | CH₃ | CH₃ | |
| H | CH₂C(O)N(CH₃)₂ | H | N | CH₃ | OCH₃ | |
| H | CH₂C(O)N(CH₃)₂ | H | N | OCH₃ | OCH₃ | |
| H | CH₂C(O)N(CH₃)₂ | H | N | OCH₂CH₃ | NHCH₃ | |
| H | CH₂C(O)N(CH₃)₂ | CH₃ | N | CH₃ | OCH₃ | |
| Cl | CH₂C(O)N(CH₃)₂ | H | CH | CH₃ | OCH₃ | |
| Cl | CH₂C(O)N(CH₃)₂ | H | N | CH₃ | OCH₃ | |
| SCH₃ | CH₂C(O)N(CH₃)₂ | H | CH | CH₃ | OCH₃ | |
| SCH₃ | CH₂C(O)N(CH₃)₂ | H | N | CH₃ | OCH₃ | |
| CO₂CH₃ | CH₂C(O)N(CH₃)₂ | H | CH | CH₃ | OCH₃ | |
| CO₂CH₃ | CH₂C(O)N(CH₃)₂ | H | N | CH₃ | OCH₃ | |
| CON(CH₃)₂ | CH₂C(O)N(CH₃)₂ | H | CH | CH₃ | OCH₃ | |
| CON(CH₃)₂ | CH₂C(O)N(CH₃)₂ | H | N | CH₃ | OCH₃ | |
| H | CH₂CN | H | CH | CH₃ | CH₃ | |
| H | CH₂CN | H | CH | CH₃ | OCH₃ | |
| H | CH₂CN | H | CH | OCH₃ | OCH₃ | |
| H | CH₂CN | H | CH | Cl | OCH₃ | |
| H | CH₂CN | H | N | CH₃ | CH₃ | |
| H | CH₂CN | H | N | CH₃ | OCH₃ | |
| H | CH₂CN | H | N | OCH₃ | OCH₃ | |
| H | CH₂CN | H | N | OCH₂CH₃ | NHCH₃ | |
| H | CH₂CN | CH₃ | N | CH₃ | OCH₃ | |
| H | (CH₂)₂CN | H | CH | CH₃ | CH₃ | |
| H | (CH₂)₂CN | H | CH | CH₃ | OCH₃ | |
| H | (CH₂)₂CN | H | CH | OCH₃ | OCH₃ | |
| H | (CH₂)₂CN | H | CH | Cl | OCH₃ | |
| H | (CH₂)₂CN | H | N | CH₃ | CH₃ | |
| H | (CH₂)₂CN | H | N | CH₃ | OCH₃ | |
| H | (CH₂)₂CN | H | N | OCH₃ | OCH₃ | |
| H | (CH₂)₂CN | H | N | OCH₂CH₃ | NHCH₃ | |
| H | (CH₂)₂CN | CH₃ | N | CH₃ | OCH₃ | |
| Cl | CH₂CN | H | CH | CH₃ | OCH₃ | |
| Cl | CH₂CN | H | N | CH₃ | OCH₃ | |
| SCH₃ | CH₂CN | H | CH | CH₃ | OCH₃ | |
| SCH₃ | CH₂CN | H | N | CH₃ | OCH₃ | |
| CO₂CH₃ | (CH₂)₂CN | H | CH | CH₃ | OCH₃ | |
| | CO CH (CH₂)₃CN₂ ₂ | H | N | CH₃ | OCH₃ | |
| | C(O)N(CH₃)₂CH₂CN | H | CH | CH₃ | OCH₃ | |
| | C(O)N(CH₃)₂CH₂CN | H | N | CH₃ | OCH₃ | |

TABLE 1-continued

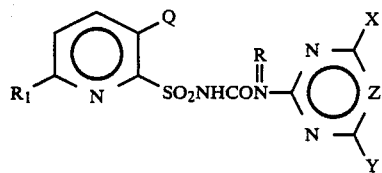

| R₁ | Q | R | Z | X | Y | m.p. (°C.) |
|---|---|---|---|---|---|---|
| H | CH₂CH=NOCH₃ | H | CH | CH₃ | CH₃ | |
| H | CH₂CH=NOCH₃ | H | CH | CH₃ | OCH₃ | |
| H | CH₂CH=NOCH₃ | H | CH | OCH₃ | OCH₃ | |
| H | CH₂CH=NOCH₃ | H | CH | Cl | OCH₃ | |
| H | CH₂CH=NOCH₃ | H | N | CH₃ | CH₃ | |
| H | CH₂CH=NOCH₃ | H | N | CH₃ | OCH₃ | |
| H | CH₂CH=NOCH₃ | H | N | OCH₃ | OCH₃ | |
| H | CH₂CH=NOCH₃ | H | N | OCH₂CH₃ | NHCH₃ | |
| H | CH₂CH=NOCH₃ | CH₃ | N | CH₃ | OCH₃ | |
| H | (CH₂)₂CH=NOCH₃ | H | CH | CH₃ | CH₃ | |
| H | (CH₂)₂CH=NOCH₃ | H | CH | CH₃ | OCH₃ | |
| H | (CH₂)₂CH=NOCH₃ | H | CH | OCH₃ | OCH₃ | |
| H | (CH₂)₂CH=NOCH₃ | H | CH | Cl | OCH₃ | |
| H | (CH₂)₂CH=NOCH₃ | H | N | CH₃ | CH₃ | |
| H | (CH₂)₂CH=NOCH₃ | H | N | CH₃ | OCH₃ | |
| H | (CH₂)₂CH=NOCH₃ | H | N | OCH₃ | OCH₃ | |
| H | (CH₂)₂CH=NOCH₃ | H | N | OCH₂CH₃ | NHCH₃ | |
| H | (CH₂)₂CH=NOCH₃ | CH₃ | N | CH₃ | OCH₃ | |
| H | CH₂C(CH₃)=NOCH₃ | H | CH | CH₃ | CH₃ | |
| H | CH₂C(CH₃)=NOCH₃ | H | CH | CH₃ | OCH₃ | |
| H | CH₂C(CH₃)=NOCH₃ | H | CH | OCH₃ | OCH₃ | |
| H | CH₂C(CH₃)=NOCH₃ | H | CH | Cl | OCH₃ | |
| H | CH₂C(CH₃)=NOCH₃ | H | N | CH₃ | CH₃ | |
| H | CH₂C(CH₃)=NOCH₃ | H | N | CH₃ | OCH₃ | |
| H | CH₂C(CH₃)=NOCH₃ | H | N | OCH₃ | OCH₃ | |
| H | CH₂C(CH₃)=NOCH₃ | H | N | OCH₂CH₃ | NHCH₃ | |
| H | CH₂C(CH₃)=NOCH₃ | CH₃ | N | CH₃ | OCH₃ | |
| H | (CH₂)₂C(CH₃)=NOCH₃ | H | CH | CH₃ | OCH₃ | |
| H | (CH₂)₂C(CH₃)=NOCH₃ | H | N | CH₃ | OCH₃ | |
| H | CH₂CH=NOCH₂CH₃ | H | CH | CH₃ | OCH₃ | |
| H | CH₂CH=NOCH₂CH₃ | H | N | CH₃ | OCH₃ | |
| H | CH₂C(CH₃)=NOCH₂CH₃ | H | CH | CH₃ | OCH₃ | |
| H | CH₂C(CH₃)=NOCH₂CH₃ | H | N | CH₃ | OCH₃ | |
| H | CH₂-⟨O-CH₂-CH₂-O⟩ | H | CH | CH₃ | CH₃ | |
| H | CH₂-⟨O-CH₂-CH₂-O⟩ | H | CH | CH₃ | OCH₃ | |
| H | CH₂-⟨O-CH₂-CH₂-O⟩ | H | CH | OCH₃ | OCH₃ | |
| H | CH₂-⟨O-CH₂-CH₂-O⟩ | H | CH | Cl | OCH₃ | |
| H | CH₂-⟨O-CH₂-CH₂-O⟩ | H | N | CH₃ | CH₃ | |
| H | CH₂-⟨O-CH₂-CH₂-O⟩ | H | N | CH₃ | OCH₃ | |

TABLE 1-continued

| R₁ | Q | R | Z | X | Y | m.p. (°C.) |
|---|---|---|---|---|---|---|
| H | CH₂-(1,3-dioxolane) | H | N | OCH₃ | OCH₃ | |
| H | CH₂-(1,3-dioxolane) | H | N | OCH₂CH₃ | NHCH₃ | |
| H | CH₂-(1,3-dioxolane) | CH₃ | N | CH₃ | OCH₃ | |
| H | CH₂-(1,3-dithiolane) | H | CH | CH₃ | OCH₃ | |
| H | CH₂-(1,3-dithiolane) | H | N | CH₃ | OCH₃ | |
| H | (CH₂)₂-(4-methyl-1,3-dioxolane) | H | CH | CH₃ | OCH₃ | |
| H | (CH₂)₂-(4-methyl-1,3-dioxolane) | H | N | CH₃ | OCH₃ | |
| H | CH₂-(1,3-dioxane) | H | CH | CH₃ | OCH₃ | |
| H | CH₂-(1,3-dioxane) | H | N | CH₃ | OCH₃ | |
| H | CH₂-(1,3-dithiane) | H | CH | CH₃ | CH₃ | |
| H | CH₂-(1,3-dithiane) | H | CH | CH₃ | OCH₃ | |

TABLE 1-continued

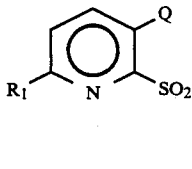

| R$_1$ | Q | R | Z | X | Y | m.p. (°C.) |
|---|---|---|---|---|---|---|
| H | 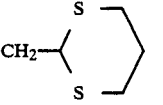 | H | CH | OCH$_3$ | OCH$_3$ | |
| H | 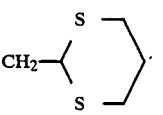 | H | CH | Cl | OCH$_3$ | |
| H | 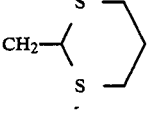 | H | N | CH$_3$ | CH$_3$ | |
| H | 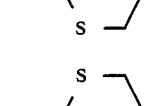 | H | N | CH$_3$ | OCH$_3$ | |
| H | 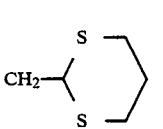 | H | N | OCH$_3$ | OCH$_3$ | |
| H | 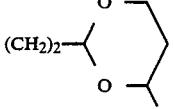 | H | N | OCH$_2$CH$_3$ | NHCH$_3$ | |
| H | 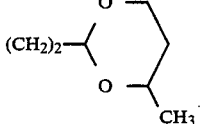 | CH$_3$ | N | CH$_3$ | OCH$_3$ | |
| H | 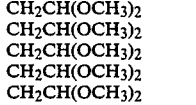 | H | CH | CH$_3$ | OCH$_3$ | |
| H | 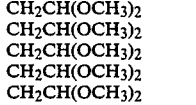 | H | N | CH$_3$ | OCH$_3$ | |
| H | CH$_2$CH(OCH$_3$)$_2$ | H | CH | CH$_3$ | CH$_3$ | |
| H | CH$_2$CH(OCH$_3$)$_2$ | H | CH | CH$_3$ | OCH$_3$ | |
| H | CH$_2$CH(OCH$_3$)$_2$ | H | CH | OCH$_3$ | OCH$_3$ | |
| H | CH$_2$CH(OCH$_3$)$_2$ | H | CH | Cl | OCH$_3$ | |
| H | CH$_2$CH(OCH$_3$)$_2$ | H | N | CH$_3$ | CH$_3$ | |
| H | CH$_2$CH(OCH$_3$)$_2$ | H | N | CH$_3$ | OCH$_3$ | |
| H | CH$_2$CH(OCH$_3$)$_2$ | H | N | OCH$_3$ | OCH$_3$ | |
| H | CH$_2$CH(OCH$_3$)$_2$ | H | N | OCH$_2$CH$_3$ | NHCH$_3$ | |
| H | CH$_2$CH(OCH$_3$)$_2$ | CH$_3$ | N | CH$_3$ | OCH$_3$ | |
| H | (CH$_2$)$_2$CH(OCH$_3$)$_2$ | H | CH | CH$_3$ | CH$_3$ | |
| H | (CH$_2$)$_2$CH(OCH$_3$)$_2$ | H | CH | CH$_3$ | OCH$_3$ | |
| H | (CH$_2$)$_2$CH(OCH$_3$)$_2$ | H | CH | OCH$_3$ | OCH$_3$ | |

TABLE 1-continued

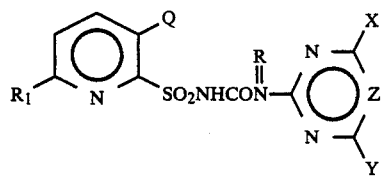

| R₁ | Q | R | Z | X | Y | m.p. (°C.) |
|---|---|---|---|---|---|---|
| H | (CH₂)₂CH(OCH₃)₂ | H | CH | Cl | OCH₃ | |
| H | (CH₂)₂CH(OCH₃)₂ | H | N | CH₃ | CH₃ | |
| H | (CH₂)₂CH(OCH₃)₂ | H | N | CH₃ | OCH₃ | |
| H | (CH₂)₂CH(OCH₃)₂ | H | N | OCH₃ | OCH₃ | |
| H | (CH₂)₂CH(OCH₃)₂ | H | N | OCH₂CH₃ | NHCH₃ | |
| H | (CH₂)₂CH(OCH₃)₂ | CH₃ | N | CH₃ | OCH₃ | |
| Cl | CH₂CH(OCH₃)₂ | H | CH | CH₃ | OCH₃ | |
| Cl | CH₂CH(OCH₃)₂ | H | N | CH₃ | OCH₃ | |
| SCH₃ | CH₂CH(OCH₃)₂ | H | CH | CH₃ | OCH₃ | |
| SCH₃ | CH₂CH(OCH₃)₂ | H | N | CH₃ | OCH₃ | |
| CO₂CH₃ | CH₂CH(OCH₃)₂ | H | CH | CH₃ | OCH₃ | |
| CO₂CH₃ | CH₂CH(OCH₃)₂ | H | N | CH₃ | OCH₃ | |
| C(O)N(CH₃)₂ | CH₂CH(OCH₃)₂ | H | CH | CH₃ | OCH₃ | |
| C(O)N(CH₃)₂ | CH₂CH(OCH₃)₂ | H | N | CH₃ | OCH₃ | |
| H | CH₂CH(SCH₃)₂ | H | CH | CH₃ | OCH₃ | |
| H | CH₂CH(SCH₃)₂ | H | N | CH₃ | OCH₃ | |
| H | CH₂C(CH₃)(OCH₃)₂ | H | CH | CH₃ | OCH₃ | |
| H | CH₂C(CH₃)(OCH₃)₂ | H | N | CH₃ | OCH₃ | |
| H | CH₂C(CH₃)(SCH₃)₂ | H | CH | CH₃ | OCH₃ | |
| H | CH₂C(CH₃)(SCH₃)₂ | H | N | CH₃ | OCH₃ | |
| H | CH₂CH(OCH₂CH₃)₂ | H | CH | CH₃ | OCH₃ | |
| H | CH₂CH(OCH₂CH₃)₂ | H | N | CH₃ | OCH₃ | |
| H | CH₂CH(OCH₂CH₃)₂ | H | CH | CH₃ | OCH₃ | |
| H | CH₂CH(OCH₂CH₃)₂ | H | N | CH₃ | OCH₃ | |
| H | (CH₂)₂CH(OCH₂CH₃)₂ | H | CH | CH₃ | OCH₃ | |
| H | (CH₂)₂CH(OCH₂CH₃)₂ | H | N | CH₃ | OCH₃ | |
| H | CH₂P(O)(OCH₂CH₃)₂ | H | CH | CH₃ | OCH₃ | 116–118 |
| H | CH₂P(O)(OCH₂CH₃)₂ | H | CH | OCH₃ | OCH₃ | 139–140 |
| H | CH₂P(O)(OCH₂CH₃)₂ | H | N | OCH₃ | OCH₃ | 115–116 |

TABLE 2

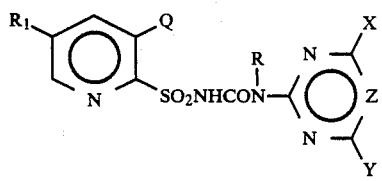

| R₁ | Q | R | Z | X | Y | m.p. (°C.) |
|---|---|---|---|---|---|---|
| CH₃ | CH₂OCH₃ | H | CH | CH₃ | CH₃ | |
| CH₃ | CH₂OCH₃ | H | CH | CH₃ | OCH₃ | |
| CH₃ | CH₂OCH₃ | H | CH | OCH₃ | OCH₃ | |
| CH₃ | CH₂OCH₃ | H | CH | Cl | OCH₃ | |
| CH₃ | CH₂OCH₃ | H | N | CH₃ | CH₃ | |
| CH₃ | CH₂OCH₃ | H | N | CH₃ | OCH₃ | |
| CH₃ | CH₂OCH₃ | H | N | OCH₃ | OCH₃ | |
| CH₃ | CH₂OCH₃ | H | N | OCH₂CH₃ | NHCH₃ | |
| CH₃ | CH₂OCH₃ | CH₃ | N | CH₃ | OCH₃ | |
| F | CH₂OCH₃ | H | CH | CH₃ | CH₃ | |
| F | CH₂OCH₃ | H | CH | CH₃ | OCH₃ | |
| F | CH₂OCH₃ | H | CH | OCH₃ | OCH₃ | |
| F | CH₂OCH₃ | H | CH | Cl | OCH₃ | |
| F | CH₂OCH₃ | H | N | CH₃ | CH₃ | |
| F | CH₂OCH₃ | H | N | CH₃ | OCH₃ | |
| F | CH₂OCH₃ | H | N | OCH₃ | OCH₃ | |
| F | CH₂OCH₃ | H | N | OCH₂CH₃ | NHCH₃ | |
| F | CH₂OCH₃ | CH₃ | N | CH₃ | OCH₃ | |
| Cl | CH₂OCH₃ | H | CH | CH₃ | CH₃ | |
| Cl | CH₂OCH₃ | H | CH | CH₃ | OCH₃ | 206–209 |
| Cl | CH₂OCH₃ | H | CH | OCH₃ | OCH₃ | 187–190 |
| Cl | CH₂OCH₃ | H | CH | Cl | OCH₃ | |
| Cl | CH₂OCH₃ | H | N | CH₃ | CH₃ | |
| Cl | CH₂OCH₃ | H | N | CH₃ | OCH₃ | |
| Cl | CH₂OCH₃ | H | N | OCH₃ | OCH₃ | 175–178 |
| Cl | CH₂OCH₃ | H | N | OCH₂CH₃ | NHCH₃ | |
| Cl | CH₂OCH₃ | CH₃ | N | CH₃ | OCH₃ | |

TABLE 2-continued

| $R_1$ | Q | R | Z | X | Y | m.p. (°C.) |
|---|---|---|---|---|---|---|
| $CH_3$ | $(CH_2)_2OCH_3$ | H | CH | $CH_3$ | $OCH_3$ | |
| $CH_3$ | $(CH_2)_2OCH_3$ | H | N | $OCH_2CH_3$ | $NHCH_3$ | |
| F | $(CH_2)_2OCH_3$ | H | CH | $CH_3$ | $OCH_3$ | |
| F | $(CH_2)_2OCH_3$ | H | N | $CH_3$ | $OCH_3$ | |
| Cl | $(CH_2)_2OCH_3$ | H | CH | $CH_3$ | $OCH_3$ | |
| Cl | $(CH_2)_2OCH_3$ | H | N | $CH_3$ | $OCH_3$ | |
| Cl | $CH_2SCH_3$ | H | CH | $CH_3$ | $OCH_3$ | |
| Cl | $CH_2SCH_3$ | H | N | $CH_3$ | $OCH_3$ | |
| Cl | $(CH_2)_2SCH_3$ | H | CH | $CH_3$ | $OCH_3$ | |
| Cl | $(CH_2)_2SCH_3$ | H | N | $CH_3$ | $OCH_3$ | |
| Cl | $CH_2S(O)CH_3$ | H | CH | $CH_3$ | $OCH_3$ | |
| Cl | $CH_2S(O)CH_3$ | H | N | $CH_3$ | $OCH_3$ | |
| Cl | $CH_2SO_2CH_3$ | H | CH | $CH_3$ | $OCH_3$ | |
| Cl | $CH_2SO_2CH_3$ | H | N | $CH_3$ | $OCH_3$ | |
| Cl | $CH_2CO_2CH_3$ | H | CH | $CH_3$ | $OCH_3$ | |
| Cl | $CH_2CO_2CH_3$ | H | N | $CH_3$ | $OCH_3$ | |
| Cl | $CH_2C(O)N(CH_3)_2$ | H | CH | $CH_3$ | $OCH_3$ | |
| Cl | $CH_2C(O)N(CH_3)_2$ | H | N | $CH_3$ | $OCH_3$ | |
| Cl | $CH_2CN$ | H | CH | $CH_3$ | $OCH_3$ | |
| Cl | $CH_2CN$ | H | N | $CH_3$ | $OCH_3$ | |
| Cl | $CH_2CH=NOCH_3$ | H | CH | $CH_3$ | $OCH_3$ | |
| Cl | $CH_2CH=NOCH_3$ | H | N | $CH_3$ | $OCH_3$ | |
| Cl | $CH_2C(CH_3)=NOCH_3$ | H | CH | $CH_3$ | $OCH_3$ | |
| Cl | $CH_2C(CH_3)=NOCH_3$ | H | N | $CH_3$ | $OCH_3$ | |
| Cl | $CH_2$-(1,3-dioxolan-2-yl) | H | CH | $CH_3$ | $OCH_3$ | |
| Cl | $CH_2$-(1,3-dioxolan-2-yl) | H | N | $CH_3$ | $OCH_3$ | |
| Cl | $CH_2$-(1,3-dithiolan-2-yl) | H | CH | $CH_3$ | $OCH_3$ | |
| Cl | $CH_2$-(1,3-dithiolan-2-yl) | H | N | $CH_3$ | $OCH_3$ | |
| Cl | $CH_2CH(OCH_3)_2$ | H | CH | $CH_3$ | $OCH_3$ | |
| Cl | $CH_2CH(OCH_3)_2$ | H | N | $CH_3$ | $OCH_3$ | |

TABLE 3

| $R_1$ | Q | R | Z | X | Y |
|---|---|---|---|---|---|
| $OCH_3$ | $CH_2OCH_3$ | H | CH | $CH_3$ | $CH_3$ |
| $OCH_3$ | $CH_2OCH_3$ | H | CH | $CH_3$ | $OCH_3$ |
| $OCH_3$ | $CH_2OCH_3$ | H | CH | $OCH_3$ | $OCH_3$ |

TABLE 3-continued

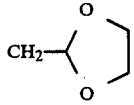

| R₁ | Q | R | Z | X | Y |
|---|---|---|---|---|---|
| OCH₃ | CH₂OCH₃ | H | CH | Cl | OCH₃ |
| OCH₃ | CH₂OCH₃ | H | N | CH₃ | CH₃ |
| OCH₃ | CH₂OCH₃ | H | N | CH₃ | OCH₃ |
| OCH₃ | CH₂OCH₃ | H | N | OCH₃ | OCH₃ |
| OCH₃ | CH₂OCH₃ | H | N | OCH₂CH₃ | NHCH₃ |
| OCH₃ | CH₂OCH₃ | CH₃ | N | CH₃ | OCH₃ |
| S(O)CH₃ | CH₂OCH₃ | H | CH | CH₃ | CH₃ |
| S(O)CH₃ | CH₂OCH₃ | H | CH | CH₃ | OCH₃ |
| S(O)CH₃ | CH₂OCH₃ | H | CH | OCH₃ | OCH₃ |
| S(O)CH₃ | CH₂OCH₃ | H | CH | Cl | OCH₃ |
| S(O)CH₃ | CH₂OCH₃ | H | N | CH₃ | CH₃ |
| S(O)CH₃ | CH₂OCH₃ | H | N | CH₃ | OCH₃ |
| S(O)CH₃ | CH₂OCH₃ | H | N | OCH₃ | OCH₃ |
| S(O)CH₃ | CH₂OCH₃ | H | N | OCH₂CH₃ | NHCH₃ |
| S(O)CH₃ | CH₂OCH₃ | CH₃ | N | CH₃ | OCH₃ |
| N(CH₃)₂ | CH₂OCH₃ | H | CH | CH₃ | CH₃ |
| N(CH₃)₂ | CH₂OCH₃ | H | CH | CH₃ | OCH₃ |
| N(CH₃)₂ | CH₂OCH₃ | H | CH | OCH₃ | OCH₃ |
| N(CH₃)₂ | CH₂OCH₃ | H | CH | Cl | OCH₃ |
| N(CH₃)₂ | CH₂OCH₃ | H | N | CH₃ | CH₃ |
| N(CH₃)₂ | CH₂OCH₃ | H | N | CH₃ | OCH₃ |
| N(CH₃)₂ | CH₂OCH₃ | H | N | OCH₃ | OCH₃ |
| N(CH₃)₂ | CH₂OCH₃ | H | N | OCH₂CH₃ | NHCH₃ |
| N(CH₃)₂ | CH₂OCH₃ | CH₃ | N | CH₃ | OCH₃ |
| CH₃ | (CH₂)₂OCH₃ | H | CH | CH₃ | OCH₃ |
| CH₃ | (CH₂)₂OCH₃ | H | N | CH₃ | OCH₃ |
| S(O)CH₃ | (CH₂)₂OCH₃ | H | CH | CH₃ | OCH₃ |
| S(O)CH₃ | (CH₂)₂OCH₃ | H | N | CH₃ | OCH₃ |
| N(CH₃)₂ | (CH₂)₂OCH₃ | H | CH | CH₃ | OCH₃ |
| N(CH₃)₂ | (CH₂)₂OCH₃ | H | N | CH₃ | OCH₃ |
| OCH₃ | CH₂SCH₃ | H | CH | CH₃ | OCH₃ |
| OCH₃ | CH₂SCH₃ | H | N | CH₃ | OCH₃ |
| OCH₃ | (CH₂)₂SCH₃ | H | CH | CH₃ | OCH₃ |
| OCH₃ | (CH₂)₂SCH₃ | H | N | CH₃ | OCH₃ |
| OCH₃ | CH₂S(O)CH₃ | H | CH | CH₃ | OCH₃ |
| OCH₃ | CH₂S(O)CH₃ | H | N | CH₃ | OCH₃ |
| OCH₃ | CH₂SO₂CH₃ | H | CH | CH₃ | OCH₃ |
| OCH₃ | CH₂SO₂CH₃ | H | N | CH₃ | OCH₃ |
| OCH₃ | CH₂CO₂CH₃ | H | CH | CH₃ | OCH₃ |
| OCH₃ | CH₂CO₂CH₃ | H | N | CH₃ | OCH₃ |
| OCH₃ | CH₂C(O)N(CH₃)₂ | H | CH | CH₃ | OCH₃ |
| OCH₃ | CH₂C(O)N(CH₃)₂ | H | N | CH₃ | OCH₃ |
| OCH₃ | CH₂CN | H | CH | CH₃ | OCH₃ |
| OCH₃ | CH₂CN | H | N | CH₃ | OCH₃ |
| OCH₃ | CH₂CH=NOCH₃ | H | CH | CH₃ | OCH₃ |
| OCH₃ | CH₂CH=NOCH₃ | H | N | CH₃ | OCH₃ |
| OCH₃ | CH₂C(CH₃)=NOCH₃ | H | CH | CH₃ | OCH₃ |
| OCH₃ | CH₂C(CH₃)=NOCH₃ | H | N | CH₃ | OCH₃ |
| OCH₃ | 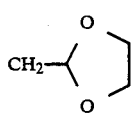 | H | CH | CH₃ | OCH₃ |
| OCH₃ | 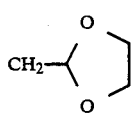 | H | N | CH₃ | OCH₃ |
| OCH₃ | 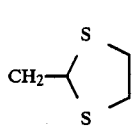 | H | CH | CH₃ | OCH₃ |

TABLE 3-continued

[Structure: pyridine with R1 at 4-position, Q at 3-position, SO2NHCON(R)- linked to pyrimidine/triazine ring with X, Y, Z substituents]

| R1 | Q | R | Z | X | Y |
|---|---|---|---|---|---|
| OCH3 | CH2-CH(S-CH2-CH2-S) (1,3-dithiolane) | H | N | CH3 | OCH3 |
| OCH3 | CH2CH(OCH3)2 | H | CH | CH3 | OCH3 |
| OCH3 | CH2CH(OCH3)2 | H | N | CH3 | OCH3 |
| OCH3 | CH2CH(SCH3)2 | H | CH | CH3 | OCH3 |
| OCH3 | CH2CH(SCH3)2 | H | N | CH3 | OCH3 |
| OCH3 | CH2C(CH3)(OCH3)2 | H | CH | CH3 | OCH3 |
| OCH3 | CH2C(CH3)(OCH3)2 | H | N | CH3 | OCH3 |
| OCH3 | (CH2)2CH(OCH3)2 | H | CH | CH3 | OCH3 |
| OCH3 | (CH2)2CH(OCH3)2 | H | N | CH3 | OCH3 |

TABLE 4

[Structure: pyridine with R1 at 4-position, Q at 2-position, SO2NHCON(R)- linked to pyrimidine/triazine ring with X, Y, Z substituents]

| R1 | Q | R | Z | X | Y |
|---|---|---|---|---|---|
| H | CH2OCH3 | H | CH | CH3 | CH3 |
| H | CH2OCH3 | H | CH | CH3 | OCH3 |
| H | CH2OCH3 | H | CH | OCH3 | OCH3 |
| H | CH2OCH3 | H | CH | Cl | OCH3 |
| H | CH2OCH3 | H | N | CH3 | CH3 |
| H | CH2OCH3 | H | N | CH3 | OCH3 |
| H | CH2OCH3 | H | N | OCH3 | OCH3 |
| H | CH2OCH3 | H | N | OCH2CH3 | NHCH3 |
| H | (CH2)2OCH3 | H | CH | CH3 | CH3 |
| H | (CH2)2OCH3 | H | CH | CH3 | OCH3 |
| H | (CH2)2OCH3 | H | CH | OCH3 | OCH3 |
| H | (CH2)2OCH3 | H | CH | Cl | OCH3 |
| H | (CH2)2OCH3 | H | N | CH3 | CH3 |
| H | (CH2)2OCH3 | H | N | CH3 | OCH3 |
| H | (CH2)2OCH3 | H | N | OCH3 | OCH3 |
| H | (CH2)2OCH3 | H | N | OCH2CH3 | NHCH3 |
| H | CH2SCH3 | H | CH | CH3 | CH3 |
| H | CH2SCH3 | H | CH | CH3 | OCH3 |
| H | CH2SCH3 | H | CH | OCH3 | OCH3 |
| H | CH2SCH3 | H | CH | Cl | OCH3 |
| H | CH2SCH3 | H | N | CH3 | CH3 |
| H | CH2SCH3 | H | N | CH3 | OCH3 |
| H | CH2SCH3 | H | N | OCH3 | OCH3 |
| H | CH2SCH3 | H | N | OCH2CH3 | NHCH3 |
| H | (CH2)2SCH3 | H | CH | CH3 | CH3 |
| H | (CH2)2SCH3 | H | CH | CH3 | OCH3 |
| H | (CH2)2SCH3 | H | CH | OCH3 | OCH3 |
| H | (CH2)2SCH3 | H | CH | Cl | OCH3 |
| H | (CH2)2SCH3 | H | N | CH3 | CH3 |
| H | (CH2)2SCH3 | H | N | CH3 | OCH3 |
| H | (CH2)2SCH3 | H | N | OCH3 | OCH3 |
| H | (CH2)2SCH3 | H | N | OCH2CH3 | NHCH3 |
| H | CH2S(O)CH3 | H | CH | CH3 | OCH3 |
| H | CH2S(O)CH3 | H | N | CH3 | OCH3 |
| H | (CH2)2S(O)CH3 | H | CH | CH3 | OCH3 |
| H | (CH2)2S(O)CH3 | H | N | CH3 | OCH3 |
| H | CH2SO2CH3 | H | CH | CH3 | OCH3 |
| H | CH2SO2CH3 | H | N | CH3 | OCH3 |
| H | (CH2)2SO2CH3 | H | CH | CH3 | OCH3 |
| H | (CH2)2SO2CH3 | H | N | CH3 | OCH3 |
| H | CH2CO2CH3 | H | CH | CH3 | OCH3 |

TABLE 4-continued

Structure: pyridine with R₁ at 4-position, SO₂NHCON(R)- at 3-position, Q at 2-position (with N in ring), linked to pyrimidine/triazine ring bearing X, Y, Z (N, X, Z, Y substituents).

| R₁ | Q | R | Z | X | Y |
|---|---|---|---|---|---|
| H | CH₂CO₂CH₃ | H | N | CH₃ | OCH₃ |
| H | (CH₂)₂CO₂CH₃ | H | CH | CH₃ | OCH₃ |
| H | (CH₂)₂CO₂CH₃ | H | N | CH₃ | OCH₃ |
| H | CH₂C(O)N(CH₃)₂ | H | CH | CH₃ | OCH₃ |
| H | CH₂C(O)N(CH₃)₂ | H | N | CH₃ | OCH₃ |
| H | (CH₂)₂C(O)N(CH₃)₂ | H | CH | CH₃ | OCH₃ |
| H | (CH₂)₂C(O)N(CH₃)₂ | H | N | CH₃ | OCH₃ |
| H | CH₂CN | H | CH | CH₃ | OCH₃ |
| H | CH₂CN | H | N | CH₃ | OCH₃ |
| H | (CH₂)₂CN | H | CH | CH₃ | OCH₃ |
| H | (CH₂)₂CN | H | N | CH₃ | OCH₃ |
| H | CH₂CH=NOCH₃ | H | CH | CH₃ | OCH₃ |
| H | CH₂CH=NOCH₃ | H | N | CH₃ | OCH₃ |
| H | (CH₂)₂CH=NOCH₃ | H | CH | CH₃ | OCH₃ |
| H | (CH₂)₂CH=NOCH₃ | H | N | CH₃ | OCH₃ |
| H | CH₂C(CH₃)=NOCH₃ | H | CH | CH₃ | OCH₃ |
| H | CH₂C(CH₃)=NOCH₃ | H | N | CH₃ | OCH₃ |
| H | (CH₂)₂C(CH₃)=NOCH₃ | H | CH | CH₃ | OCH₃ |
| H | (CH₂)₂C(CH₃)=NOCH₃ | H | N | CH₃ | OCH₃ |
| H | CH₂-CH(OCH₂CH₂O) (1,3-dioxolan-2-yl-methyl) | H | CH | CH₃ | OCH₃ |
| H | CH₂-CH(OCH₂CH₂O) (1,3-dioxolan-2-yl-methyl) | H | N | CH₃ | OCH₃ |
| H | CH₂-CH(SCH₂CH₂S) (1,3-dithiolan-2-yl-methyl) | H | CH | CH₃ | OCH₃ |
| H | CH₂-CH(SCH₂CH₂S) (1,3-dithiolan-2-yl-methyl) | H | N | CH₃ | OCH₃ |
| H | CH₂CH(OCH₃)₂ | H | CH | CH₃ | OCH₃ |
| H | CH₂CH(OCH₃)₂ | H | N | CH₃ | OCH₃ |
| H | (CH₂)₂CH(OCH₃)₂ | H | CH | CH₃ | OCH₃ |
| H | (CH₂)₂CH(OCH₃)₂ | H | N | CH₃ | OCH₃ |
| H | CH₂CH(SCH₃)₂ | H | CH | CH₃ | OCH₃ |
| H | CH₂CH(SCH₃)₂ | H | N | CH₃ | OCH₃ |
| H | (CH₂)₂CH(SCH₃)₂ | H | CH | CH₃ | OCH₃ |
| H | (CH₂)₂CH(SCH₃)₂ | H | N | CH₃ | OCH₃ |
| H | CH₂C(CH₃)(OCH₃)₂ | H | CH | CH₃ | OCH₃ |
| H | CH₂C(CH₃)(OCH₃)₂ | H | N | CH₃ | OCH₃ |
| H | (CH₂)₂C(CH₃)(OCH₃)₂ | H | CH | CH₃ | OCH₃ |
| H | (CH₂)₂C(CH₃)(OCH₃)₂ | H | N | CH₃ | OCH₃ |
| H | CH₂C(CH₃)(SCH₃)₂ | H | CH | CH₃ | OCH₃ |
| H | CH₂C(CH₃)(SCH₃)₂ | H | N | CH₃ | OCH₃ |
| H | (CH₂)₂C(CH₃)(SCH₃)₂ | H | CH | CH₃ | OCH₃ |
| H | (CH₂)₂C(CH₃)(SCH₃)₂ | H | N | CH₃ | OCH₃ |
| CO₂CH₃ | CH₂OCH₃ | H | CH | CH₃ | OCH₃ |
| CO₂CH₃ | CH₂OCH₃ | H | N | CH₃ | OCH₃ |
| CO₂CH₃ | (CH₂)₂OCH₃ | H | CH | CH₃ | OCH₃ |
| CO₂CH₃ | (CH₂)₂OCH₃ | H | N | CH₃ | OCH₃ |
| F | CH₂OCH₃ | H | CH | CH₃ | OCH₃ |
| F | CH₂OCH₃ | H | N | CH₃ | OCH₃ |
| OCH₃ | CH₂OCH₃ | H | CH | CH₃ | OCH₃ |
| OCH₃ | CH₂OCH₃ | H | N | CH₃ | OCH₃ |
| CH₃ | CH₂OCH₃ | H | CH | CH₃ | OCH₃ |
| CH₃ | CH₂OCH₃ | H | N | CH₃ | OCH₃ |
| N(CH₃)₂ | CH₂OCH₃ | H | CH | CH₃ | OCH₃ |

TABLE 4-continued

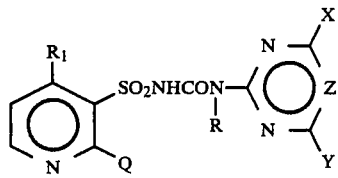

| R₁ | Q | R | Z | X | Y |
|---|---|---|---|---|---|
| N(CH₃)₂ | CH₂OCH₃ | H | N | CH₃ | OCH₃ |

TABLE 5

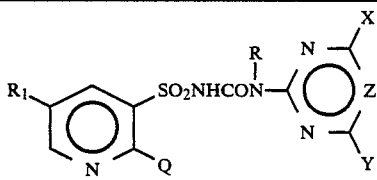

| R₁ | Q | R | Z | X | Y |
|---|---|---|---|---|---|
| OCH₃ | CH₂OCH₃ | H | CH | CH₃ | CH₃ |
| OCH₃ | CO₂OCH₃ | H | CH | CH₃ | OCH₃ |
| OCH₃ | CH₂OCH₃ | H | CH | OCH₃ | OCH₃ |
| OCH₃ | CH₂OCH₃ | H | CH | Cl | OCH₃ |
| OCH₃ | CH₂OCH₃ | H | N | CH₃ | CH₃ |
| OCH₃ | CH₂OCH₃ | H | N | CH₃ | OCH₃ |
| OCH₃ | CH₂OCH₃ | H | N | OCH₃ | OCH₃ |
| OCH₃ | CH₂OCH₃ | H | N | OCH₂CH₃ | NHCH₃ |
| OCH₃ | CH₂OCH₃ | CH₃ | N | CH₃ | OCH₃ |
| S(O)CH₃ | CH₂OCH₃ | H | CH | CH₃ | CH₃ |
| S(O)CH₃ | CH₂OCH₃ | H | CH | CH₃ | OCH₃ |
| S(O)CH₃ | CH₂OCH₃ | H | CH | OCH₃ | OCH₃ |
| S(O)CH₃ | CH₂OCH₃ | H | CH | Cl | OCH₃ |
| S(O)CH₃ | CH₂OCH₃ | H | N | CH₃ | CH₃ |
| S(O)CH₃ | CH₂OCH₃ | H | N | CH₃ | OCH₃ |
| S(O)CH₃ | CH₂OCH₃ | H | N | OCH₃ | OCH₃ |
| S(O)CH₃ | CH₂OCH₃ | H | N | OCH₂CH₃ | NHCH₃ |
| S(O)CH₃ | CH₂OCH₃ | CH₃ | N | CH₃ | OCH₃ |
| N(CH₃)₂ | CH₂OCH₃ | H | CH | CH₃ | CH₃ |
| N(CH₃)₂ | CH₂OCH₃ | H | CH | CH₃ | OCH₃ |
| N(CH₃)₂ | CH₂OCH₃ | H | CH | OCH₃ | OCH₃ |
| N(CH₃)₂ | CH₂OCH₃ | H | CH | Cl | OCH₃ |
| N(CH₃)₂ | CH₂OCH₃ | H | N | CH₃ | CH₃ |
| N(CH₃)₂ | CH₂OCH₃ | H | N | CH₃ | OCH₃ |
| N(CH₃)₂ | CH₂OCH₃ | H | N | OCH₃ | OCH₃ |
| N(CH₃)₂ | CH₂OCH₃ | H | N | OCH₂CH₃ | NHCH₃ |
| N(CH₃)₂ | CH₂OCH₃ | CH₃ | N | CH₃ | OCH₃ |
| CH₃ | (CH₂)₂OCH₃ | H | CH | CH₃ | OCH₃ |
| CH₃ | (CH₂)₂OCH₃ | H | N | CH₃ | OCH₃ |
| S(O)CH₃ | (CH₂)₂OCH₃ | H | CH | CH₃ | OCH₃ |
| S(O)CH₃ | (CH₂)₂OCH₃ | H | N | CH₃ | OCH₃ |
| N(CH₃)₂ | (CH₂)₂OCH₃ | H | CH | CH₃ | OCH₃ |
| N(CH₃)₂ | (CH₂)₂OCH₃ | H | N | CH₃ | OCH₃ |
| OCH₃ | CH₂SCH₃ | H | CH | CH₃ | OCH₃ |
| OCH₃ | CH₂SCH₃ | H | N | CH₃ | OCH₃ |
| OCH₃ | (CH₂)₂SCH₃ | H | CH | CH₃ | OCH₃ |
| OCH₃ | (CH₂)₂SCH₃ | H | N | CH₃ | OCH₃ |
| OCH₃ | CH₂S(O)CH₃ | H | CH | CH₃ | OCH₃ |
| OCH₃ | CH₂S(O)CH₃ | H | N | CH₃ | OCH₃ |
| OCH₃ | CH₂SO₂CH₃ | H | CH | CH₃ | OCH₃ |
| OCH₃ | CH₂SO₂CH₃ | H | N | CH₃ | OCH₃ |
| OCH₃ | CH₂CO₂CH₃ | H | CH | CH₃ | OCH₃ |
| OCH₃ | CH₂CO₂CH₃ | H | N | CH₃ | OCH₃ |
| OCH₃ | CH₂C(O)N(CH₃)₂ | H | CH | CH₃ | OCH₃ |
| OCH₃ | CH₂C(O)N(CH₃)₂ | H | N | CH₃ | OCH₃ |
| OCH₃ | CH₂CN | H | CH | CH₃ | OCH₃ |
| OCH₃ | CH₂CN | H | N | CH₃ | OCH₃ |
| OCH₃ | CH₂CH=NOCH₃ | H | CH | CH₃ | OCH₃ |
| OCH₃ | CH₂CH=NOCH₃ | H | N | CH₃ | OCH₃ |
| OCH₃ | CH₂C(CH₃)=NOCH₃ | H | CH | CH₃ | OCH₃ |
| OCH₃ | CH₂C(CH₃)=NOCH₃ | H | N | CH₃ | OCH₃ |

TABLE 5-continued

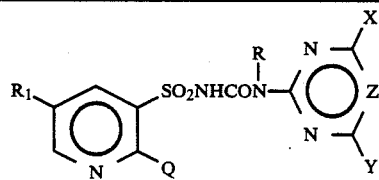

| R₁ | Q | R | Z | X | Y |
|---|---|---|---|---|---|
| OCH₃ |  (CH₂ with dioxolane O-CH-O) | H | CH | CH₃ | OCH₃ |
| OCH₃ | (CH₂ with dioxolane) | H | N | CH₃ | OCH₃ |
| OCH₃ | (CH₂ with dithiolane S-CH-S) | H | CH | CH₃ | OCH₃ |
| OCH₃ | (CH₂ with dithiolane) | H | N | CH₃ | OCH₃ |
| OCH₃ | CH₂CH(OCH₃)₂ | H | CH | CH₃ | OCH₃ |
| OCH₃ | CH₂CH(OCH₃)₂ | H | N | CH₃ | OCH₃ |
| OCH₃ | CH₂CH(SCH₃)₂ | H | CH | CH₃ | OCH₃ |
| OCH₃ | CH₂CH(SCH₃)₂ | H | N | CH₃ | OCH₃ |
| OCH₃ | CH₂C(CH₃)(OCH₃)₂ | H | CH | CH₃ | OCH₃ |
| OCH₃ | CH₂C(CH₃)(OCH₃)₂ | H | N | CH₃ | OCH₃ |
| OCH₃ | (CH₂)₂CH(OCH₃)₂ | H | CH | CH₃ | OCH₃ |
| OCH₃ | (CH₂)₂CH(OCH₃)₂ | H | N | CH₃ | OCH₃ |

TABLE 6

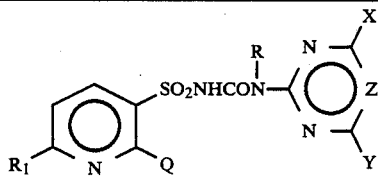

| R₁ | Q | R | Z | X | Y |
|---|---|---|---|---|---|
| CH₃ | CH₂OCH₃ | H | CH | CH₃ | CH₃ |
| CH₃ | CH₂OCH₃ | H | CH | CH₃ | OCH₃ |
| CH₃ | CH₂OCH₃ | H | CH | OCH₃ | OCH₃ |
| CH₃ | CH₂OCH₃ | H | CH | Cl | OCH₃ |
| CH₃ | CH₂OCH₃ | H | N | CH₃ | CH₃ |
| CH₃ | CH₂OCH₃ | H | N | CH₃ | OCH₃ |
| CH₃ | CH₂OCH₃ | H | N | OCH₃ | OCH₃ |
| CH₃ | CH₂OCH₃ | H | N | OCH₂CH₃ | NHCH₃ |
| CH₃ | CH₂OCH₃ | CH₃ | N | CH₃ | OCH₃ |
| F | CH₂OCH₃ | H | CH | CH₃ | CH₃ |
| F | CH₂OCH₃ | H | CH | CH₃ | OCH₃ |
| F | CH₂OCH₃ | H | CH | OCH₃ | OCH₃ |
| F | CH₂OCH₃ | H | CH | Cl | OCH₃ |
| F | CH₂OCH₃ | H | N | CH₃ | CH₃ |
| F | CH₂OCH₃ | H | N | CH₃ | OCH₃ |
| F | CH₂OCH₃ | H | N | OCH₃ | OCH₃ |
| F | CH₂OCH₃ | H | N | OCH₂CH₃ | NHCH₃ |
| F | CH₂OCH₃ | CH₃ | N | CH₃ | OCH₃ |
| Cl | CH₂OCH₃ | H | CH | CH₃ | CH₃ |
| Cl | CH₂OCH₃ | H | CH | CH₃ | OCH₃ |
| Cl | CH₂OCH₃ | H | CH | OCH₃ | OCH₃ |
| Cl | CH₂OCH₃ | H | CH | Cl | OCH₃ |
| Cl | CH₂OCH₃ | H | N | CH₃ | CH₃ |
| Cl | CH₂OCH₃ | H | N | CH₃ | OCH₃ |

TABLE 6-continued

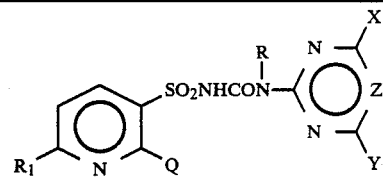

| R₁ | Q | R | Z | X | Y |
|---|---|---|---|---|---|
| Cl | CH₂OCH₃ | H | N | OCH₃ | OCH₃ |
| Cl | CH₂OCH₃ | H | N | OCH₂CH₃ | NHCH₃ |
| Cl | CH₂OCH₃ | CH₃ | N | CH₃ | OCH₃ |
| CH₃ | (CH₂)₂OCH₃ | H | CH | CH₃ | OCH₃ |
| CH₃ | (CH₂)₂OCH₃ | H | N | CH₃ | OCH₃ |
| F | (CH₂)₂OCH₃ | H | CH | CH₃ | OCH₃ |
| F | (CH₂)₂OCH₃ | H | N | CH₃ | OCH₃ |
| Cl | (CH₂)₂OCH₃ | H | CH | CH₃ | OCH₃ |
| Cl | (CH₂)₂OCH₃ | H | N | CH₃ | OCH₃ |
| Cl | CH₂SCH₃ | H | CH | CH₃ | OCH₃ |
| Cl | CH₂SCH₃ | H | N | CH₃ | OCH₃ |
| Cl | (CH₂)₂SCH₃ | H | CH | CH₃ | OCH₃ |
| Cl | (CH₂)₂SCH₃ | H | N | CH₃ | OCH₃ |
| Cl | CH₂S(O)CH₃ | H | CH | CH₃ | OCH₃ |
| Cl | CH₂S(O)CH₃ | H | N | CH₃ | OCH₃ |
| Cl | CH₂SO₂CH₃ | H | CH | CH₃ | OCH₃ |
| Cl | CH₂SO₂CH₃ | H | N | CH₃ | OCH₃ |
| Cl | CH₂CO₂CH₃ | H | CH | CH₃ | OCH₃ |
| Cl | CH₂CO₂CH₃ | H | N | CH₃ | OCH₃ |
| Cl | CH₂C(O)N(CH₃)₂ | H | CH | CH₃ | OCH₃ |
| Cl | CH₂C(O)N(CH₃)₂ | H | N | CH₃ | OCH₃ |
| Cl | CH₂CN | H | CH | CH₃ | OCH₃ |
| Cl | CH₂CN | H | N | CH₃ | OCH₃ |
| Cl | CH₂CH=NOCH₃ | H | CH | CH₃ | OCH₃ |

TABLE 6-continued

Structure: pyridine with R1 at 6-position, Q at 2-position, SO2NHCON(R)- linked to pyrimidine/triazine ring with X, Y, Z substituents.

| R₁ | Q | R | Z | X | Y |
|---|---|---|---|---|---|
| Cl | CH₂CH=NOCH₃ | H | N | CH₃ | OCH₃ |
| Cl | CH₂C(CH₃)=NOCH₃ | H | CH | CH₃ | OCH₃ |
| Cl | CH₂C(CH₃)=NOCH₃ | H | N | CH₃ | OCH₃ |
| Cl | CH₂-(1,3-dioxolan-2-yl) | H | CH | CH₃ | OCH₃ |
| Cl | CH₂-(1,3-dioxolan-2-yl) | H | N | CH₃ | OCH₃ |
| Cl | CH₂-(1,3-dithiolan-2-yl) | H | CH | CH₃ | OCH₃ |
| Cl | CH₂-(1,3-dithiolan-2-yl) | H | N | CH₃ | OCH₃ |
| Cl | CH₂CH(OCH₃)₂ | H | CH | CH₃ | OCH₃ |
| Cl | CH₂CH(OCH₃)₂ | H | N | CH₃ | OCH₃ |
| Cl | CH₂CH(SCH₃)₂ | H | CH | CH₃ | OCH₃ |
| Cl | CH₂CH(SCH₃)₂ | H | N | CH₃ | OCH₃ |
| Cl | CH₂C(CH₃)(OCH₃)₂ | H | CH | CH₃ | OCH₃ |
| Cl | CH₂C(CH₃)(OCH₃)₂ | H | N | CH₃ | OCH₃ |
| Cl | (CH₂)₂CH(OCH₃)₂ | H | CH | CH₃ | OCH₃ |
| Cl | (CH₂)₂CH(OCH₃)₂ | H | N | CH₃ | OCH₃ |

TABLE 7

Structure: pyridine with R₁ at 2-position, Q at 4-position, SO2NHCON(R)- linked to pyrimidine/triazine ring with X, Y, Z substituents.

| R₁ | Q | R | Z | X | Y |
|---|---|---|---|---|---|
| H | CH₂OCH₃ | H | CH | CH₃ | CH₃ |
| H | CH₂OCH₃ | H | CH | CH₃ | OCH₃ |
| H | CH₂OCH₃ | H | CH | OCH₃ | OCH₃ |
| H | CH₂OCH₃ | H | CH | Cl | OCH₃ |
| H | CH₂OCH₃ | H | N | CH₃ | CH₃ |
| H | CH₂OCH₃ | H | N | CH₃ | OCH₃ |
| H | CH₂OCH₃ | H | N | OCH₃ | OCH₃ |
| H | CH₂OCH₃ | H | N | OCH₂CH₃ | NHCH₃ |
| H | (CH₂)₂OCH₃ | H | CH | CH₃ | CH₃ |
| H | (CH₂)₂OCH₃ | H | CH | CH₃ | OCH₃ |
| H | (CH₂)₂OCH₃ | H | CH | OCH₃ | OCH₃ |
| H | (CH₂)₂OCH₃ | H | CH | Cl | OCH₃ |
| H | (CH₂)₂OCH₃ | H | N | CH₃ | CH₃ |
| H | (CH₂)₂OCH₃ | H | N | CH₃ | OCH₃ |
| H | (CH₂)₂OCH₃ | H | N | OCH₃ | OCH₃ |
| H | (CH₂)₂OCH₃ | H | N | OCH₂CH₃ | NHCH₃ |
| H | CH₂SCH₃ | H | CH | CH₃ | CH₃ |
| H | CH₂SCH₃ | H | CH | CH₃ | OCH₃ |
| H | CH₂SCH₃ | H | CH | OCH₃ | OCH₃ |
| H | CH₂SCH₃ | H | CH | Cl | OCH₃ |
| H | CH₂SCH₃ | H | N | CH₃ | CH₃ |
| H | CH₂SCH₃ | H | N | CH₃ | OCH₃ |
| H | CH₂SCH₃ | H | N | OCH₃ | OCH₃ |
| H | CH₂SCH₃ | H | N | OCH₂CH₃ | NHCH₃ |
| H | CH₂SCH₃ | CH₃ | N | CH₃ | OCH₃ |
| H | (CH₂)₂SCH₃ | H | CH | CH₃ | CH₃ |
| H | (CH₂)₂SCH₃ | H | CH | CH₃ | OCH₃ |
| H | (CH₂)₂SCH₃ | H | CH | OCH₃ | OCH₃ |
| H | (CH₂)₂SCH₃ | H | CH | Cl | OCH₃ |
| H | (CH₂)₂SCH₃ | H | N | CH₃ | CH₃ |
| H | (CH₂)₂SCH₃ | H | N | CH₃ | OCH₃ |
| H | (CH₂)₂SCH₃ | H | N | OCH₃ | OCH₃ |
| H | (CH₂)₂SCH₃ | H | N | OCH₂CH₃ | NHCH₃ |
| H | (CH₂)₂SCH₃ | CH₃ | N | CH₃ | OCH₃ |
| H | CH₂SCH₂CH=CH₂ | H | CH | CH₃ | OCH₃ |
| H | CH₂SCH₂CH=CH₂ | H | N | CH₃ | OCH₃ |

TABLE 7-continued

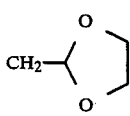

| R₁ | Q | R | Z | X | Y |
|---|---|---|---|---|---|
| H | (CH₂)₂SCH₂CH=CH₂ | H | CH | CH₃ | OCH₃ |
| H | (CH₂)₂SCH₂CH=CH₂ | H | N | CH₃ | OCH₃ |
| H | CH₂S(O)CH₃ | H | CH | CH₃ | OCH₃ |
| H | CH₂S(O)CH₃ | H | N | CH₃ | OCH₃ |
| H | (CH₂)₂S(O)CH₃ | H | CH | CH₃ | OCH₃ |
| H | (CH₂)₂S(O)CH₃ | H | N | CH₃ | OCH₃ |
| H | CH₂SO₂CH₃ | H | CH | CH₃ | OCH₃ |
| H | CH₂SO₂CH₃ | H | N | CH₃ | OCH₃ |
| H | (CH₂)₂SO₂CH₃ | H | CH | CH₃ | OCH₃ |
| H | (CH₂)₂SO₂CH₃ | H | N | CH₃ | OCH₃ |
| H | CH₂CO₂CH₃ | H | CH | CH₃ | OCH₃ |
| H | CH₂CO₂CH₃ | H | N | CH₃ | OCH₃ |
| H | (CH₂)₂CO₂CH₃ | H | CH | CH₃ | OCH₃ |
| H | (CH₂)₂CO₂CH₃ | H | N | CH₃ | OCH₃ |
| H | CH₂C(O)N(CH₃)₂ | H | CH | CH₃ | OCH₃ |
| H | CH₂C(O)N(CH₃)₂ | H | N | CH₃ | OCH₃ |
| H | (CH₂)₂C(O)N(CH₃)₂ | H | CH | CH₃ | OCH₃ |
| H | (CH₂)₂C(O)N(CH₃)₂ | H | N | CH₃ | OCH₃ |
| H | CH₂CN | H | CH | CH₃ | OCH₃ |
| H | CH₂CN | H | N | CH₃ | OCH₃ |
| H | (CH₂)₂CN | H | CH | CH₃ | OCH₃ |
| H | (CH₂)₂CN | H | N | CH₃ | OCH₃ |
| H | CH₂CH=NOCH₃ | H | CH | CH₃ | OCH₃ |
| H | CH₂CH=NOCH₃ | H | N | CH₃ | OCH₃ |
| H | (CH₂)₂CH=NOCH₃ | H | CH | CH₃ | OCH₃ |
| H | (CH₂)₂CH=NOCH₃ | H | N | CH₃ | OCH₃ |
| H | CH₂C(CH₃)=NOCH₃ | H | CH | CH₃ | OCH₃ |
| H | CH₂C(CH₃)=NOCH₃ | H | N | CH₃ | OCH₃ |
| H | (CH₂)₂C(CH₃)=NOCH₃ | H | CH | CH₃ | OCH₃ |
| H | (CH₂)₂C(CH₃)=NOCH₃ | H | N | CH₃ | OCH₃ |
| H | 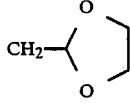 | H | CH | CH₃ | OCH₃ |
| H | 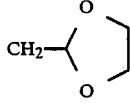 | H | N | CH₃ | OCH₃ |
| H | 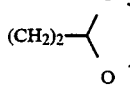 | H | CH | CH₃ | OCH₃ |
| H | 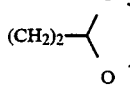 | H | N | CH₃ | OCH₃ |
| H | 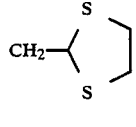 | H | CH | CH₃ | OCH₃ |
| H | 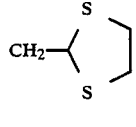 | H | N | CH₃ | OCH₃ |

TABLE 7-continued

Structure: pyridine ring with Q at 4-position, R₁ at 2-position, N in ring, and -SO₂NHCON(R)- linked to pyrimidine/triazine ring with X, Y, Z substituents.

| R₁ | Q | R | Z | X | Y |
|---|---|---|---|---|---|
| H | (CH₂)₂-CH(S-CH₂CH₂-S) (1,3-dithiolane) | H | CH | CH₃ | OCH₃ |
| H | (CH₂)₂-CH(S-CH₂CH₂-S) (1,3-dithiolane) | H | N | CH₃ | OCH₃ |
| H | CH₂CH(OCH₃)₂ | H | CH | CH₃ | OCH₃ |
| H | CH₂CH(OCH₃)₂ | H | N | CH₃ | OCH₃ |
| H | (CH₂)₂CH(OCH₃)₂ | H | CH | CH₃ | OCH₃ |
| H | (CH₂)₂CH(OCH₃)₂ | H | N | CH₃ | OCH₃ |
| H | CH₂CH(SCH₃)₂ | H | CH | CH₃ | OCH₃ |
| H | CH₂CH(SCH₃)₂ | H | N | CH₃ | OCH₃ |
| H | CH₂C(CH₃)(OCH₃)₂ | H | CH | CH₃ | OCH₃ |
| H | CH₂C(CH₃)(OCH₃)₂ | H | N | CH₃ | OCH₃ |
| H | (CH₂)₂C(CH₃)(OCH₃)₂ | H | CH | CH₃ | OCH₃ |
| H | (CH₂)₂C(CH₃)(OCH₃)₂ | H | N | CH₃ | OCH₃ |
| CO₂CH₃ | CH₂OCH₃ | H | CH | CH₃ | OCH₃ |
| CO₂CH₃ | CH₂OCH₃ | H | N | CH₃ | OCH₃ |
| CO₂CH₃ | (CH₂)₂OCH₃ | H | CH | CH₃ | OCH₃ |
| CO₂CH₃ | (CH₂)₂OCH₃ | H | N | CH₃ | OCH₃ |
| CO₂CH₃ | CH₂SCH₃ | H | CH | CH₃ | OCH₃ |
| CO₂CH₃ | CH₂SCH₃ | H | N | CH₃ | OCH₃ |
| CO₂CH₃ | (CH₂)₂SCH₃ | H | CH | CH₃ | OCH₃ |
| CO₂CH₃ | (CH₂)₂SCH₃ | H | N | CH₃ | OCH₃ |
| CH₃ | CH₂OCH₃ | H | CH | CH₃ | OCH₃ |
| CH₃ | CH₂OCH₃ | H | N | CH₃ | OCH₃ |
| OCH₃ | CH₂OCH₃ | H | CH | CH₃ | OCH₃ |
| OCH₃ | CH₂OCH₃ | H | N | CH₃ | OCH₃ |

TABLE 8

Structure: pyridine ring with R₁ at 5-position, Q at 4-position, -SO₂NHCON(R)- at 3-position, linked to pyrimidine/triazine ring with X, Y, Z substituents.

| R₁ | Q | R | Z | X | Y |
|---|---|---|---|---|---|
| OCH₃ | CH₂OCH₃ | H | CH | CH₃ | CH₃ |
| OCH₃ | CH₂OCH₃ | H | CH | CH₃ | OCH₃ |
| OCH₃ | CH₂OCH₃ | H | CH | OCH₃ | OCH₃ |
| OCH₃ | CH₂OCH₃ | H | CH | Cl | OCH₃ |
| OCH₃ | CH₂OCH₃ | H | N | CH₃ | CH₃ |
| OCH₃ | CH₂OCH₃ | H | N | CH₃ | OCH₃ |
| OCH₃ | CH₂OCH₃ | H | N | OCH₃ | OCH₃ |
| OCH₃ | CH₂OCH₃ | H | N | OCH₂CH₃ | NHCH₃ |
| OCH₃ | CH₂OCH₃ | CH₃ | N | CH₃ | OCH₃ |
| S(O)CH₃ | CH₂OCH₃ | H | CH | CH₃ | CH₃ |
| S(O)CH₃ | CH₂OCH₃ | H | CH | CH₃ | OCH₃ |
| S(O)CH₃ | CH₂OCH₃ | H | CH | OCH₃ | OCH₃ |
| S(O)CH₃ | CH₂OCH₃ | H | CH | Cl | OCH₃ |
| S(O)CH₃ | CH₂OCH₃ | H | N | CH₃ | CH₃ |
| S(O)CH₃ | CH₂OCH₃ | H | N | CH₃ | OCH₃ |
| S(O)CH₃ | CH₂OCH₃ | H | N | OCH₃ | OCH₃ |
| S(O)CH₃ | CH₂OCH₃ | H | N | OCH₂CH₃ | NHCH₃ |
| S(O)CH₃ | CH₂OCH₃ | CH₃ | N | CH₃ | OCH₃ |
| N(CH₃)₂ | CH₂OCH₃ | H | CH | CH₃ | CH₃ |
| N(CH₃)₂ | CH₂OCH₃ | H | CH | CH₃ | OCH₃ |
| N(CH₃)₂ | CH₂OCH₃ | H | CH | OCH₃ | OCH₃ |
| N(CH₃)₂ | CH₂OCH₃ | H | CH | Cl | OCH₃ |

TABLE 8-continued

| R₁ | Q | R | Z | X | Y |
|---|---|---|---|---|---|
| N(CH₃)₂ | CH₂OCH₃ | H | N | CH₃ | CH₃ |
| N(CH₃)₂ | CH₂OCH₃ | H | N | CH₃ | OCH₃ |
| N(CH₃)₂ | CH₂OCH₃ | H | N | OCH₃ | OCH₃ |
| N(CH₃)₂ | CH₂OCH₃ | H | N | OCH₂CH₃ | NHCH₃ |
| N(CH₃)₂ | CH₂OCH₃ | CH₃ | N | CH₃ | OCH₃ |
| OCH₃ | (CH₂)₂OCH₃ | H | CH | CH₃ | OCH₃ |
| OCH₃ | (CH₂)₂OCH₃ | H | N | CH₃ | OCH₃ |
| S(O)CH₃ | (CH₂)₂OCH₃ | H | CH | CH₃ | OCH₃ |
| S(O)CH₃ | (CH₂)₂OCH₃ | H | N | CH₃ | OCH₃ |
| N(CH₃)₂ | (CH₂)₂OCH₃ | H | CH | CH₃ | OCH₃ |
| N(CH₃)₂ | (CH₂)₂OCH₃ | H | N | CH₃ | OCH₃ |
| OCH₃ | CH₂SCH₃ | H | CH | CH₃ | OCH₃ |
| OCH₃ | CH₂SCH₃ | H | N | CH₃ | OCH₃ |
| OCH₃ | (CH₂)₂SCH₃ | H | CH | CH₃ | OCH₃ |
| OCH₃ | (CH₂)₂SCH₃ | H | N | CH₃ | OCH₃ |
| OCH₃ | CH₂S(O)CH₃ | H | CH | CH₃ | OCH₃ |
| OCH₃ | CH₂S(O)CH₃ | H | N | CH₃ | OCH₃ |
| OCH₃ | CH₂SO₂CH₃ | H | CH | CH₃ | OCH₃ |
| OCH₃ | CH₂SO₂CH₃ | H | N | CH₃ | OCH₃ |
| OCH₃ | CH₂CO₂CH₃ | H | CH | CH₃ | OCH₃ |
| OCH₃ | CH₂CO₂CH₃ | H | N | CH₃ | OCH₃ |
| OCH₃ | CH₂C(O)N(CH₃)₂ | H | CH | CH₃ | OCH₃ |
| OCH₃ | CH₂C(O)N(CH₃)₂ | H | N | CH₃ | OCH₃ |
| OCH₃ | CH₂CN | H | CH | CH₃ | OCH₃ |
| OCH₃ | CH₂CN | H | N | CH₃ | OCH₃ |
| OCH₃ | CH₂CH=NOCH₃ | H | CH | CH₃ | OCH₃ |
| OCH₃ | CH₂CH=NOCH₃ | H | N | CH₃ | OCH₃ |
| OCH₃ | CH₂C(CH₃)=NOCH₃ | H | CH | CH₃ | OCH₃ |
| OCH₃ | CH₂C(CH₃)=NOCH₃ | H | N | CH₃ | OCH₃ |
| OCH₃ | CH₂-(1,3-dioxolan-2-yl) | H | CH | CH₃ | OCH₃ |
| OCH₃ | CH₂-(1,3-dioxolan-2-yl) | H | N | CH₃ | OCH₃ |
| OCH₃ | CH₂-(1,3-dithiolan-2-yl) | H | CH | CH₃ | OCH₃ |
| OCH₃ | CH₂-(1,3-dithiolan-2-yl) | H | N | CH₃ | OCH₃ |
| OCH₃ | CH₂CH(OCH₃)₂ | H | CH | CH₃ | OCH₃ |
| OCH₃ | CH₂CH(OCH₃)₂ | H | N | CH₃ | OCH₃ |
| OCH₃ | CH₂CH(SCH₃)₂ | H | CH | CH₃ | OCH₃ |
| OCH₃ | CH₂CH(SCH₃)₂ | H | N | CH₃ | OCH₃ |
| OCH₃ | CH₂C(CH₃)(OCH₃)₂ | H | CH | CH₃ | OCH₃ |
| OCH₃ | CH₂C(CH₃)(OCH₃)₂ | H | N | CH₃ | OCH₃ |
| OCH₃ | (CH₂)₂CH(OCH₃)₂ | H | CH | CH₃ | OCH₃ |
| OCH₃ | (CH₂)₂CH(OCH₃)₂ | H | N | CH₃ | OCH₃ |

TABLE 9

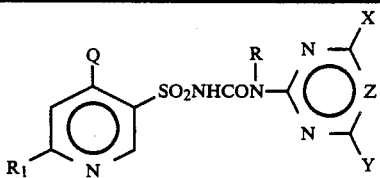

| R₁ | Q | R | Z | X | Y |
|---|---|---|---|---|---|
| CH₃ | CH₂OCH₃ | H | CH | CH₃ | CH₃ |
| CH₃ | CH₂OCH₃ | H | CH | CH₃ | OCH₃ |
| CH₃ | CH₂OCH₃ | H | CH | OCH₃ | OCH₃ |
| CH₃ | CH₂OCH₃ | H | CH | Cl | OCH₃ |
| CH₃ | CH₂OCH₃ | H | N | CH₃ | CH₃ |
| CH₃ | CH₂OCH₃ | H | N | CH₃ | OCH₃ |
| CH₃ | CH₂OCH₃ | H | N | OCH₃ | OCH₃ |
| CH₃ | CH₂OCH₃ | H | N | OCH₂CH₃ | NHCH₃ |
| CH₃ | CH₂OCH₃ | CH₃ | N | CH₃ | OCH₃ |
| F | CH₂OCH₃ | H | CH | CH₃ | CH₃ |
| F | CH₂OCH₃ | H | CH | CH₃ | OCH₃ |
| F | CH₂OCH₃ | H | CH | OCH₃ | OCH₃ |
| F | CH₂OCH₃ | H | CH | Cl | OCH₃ |
| F | CH₂OCH₃ | H | N | CH₃ | CH₃ |
| F | CH₂OCH₃ | H | N | CH₃ | OCH₃ |
| F | CH₂OCH₃ | H | N | OCH₃ | OCH₃ |
| F | CH₂OCH₃ | H | N | OCH₂CH₃ | NHCH₃ |
| F | CH₂OCH₃ | CH₃ | N | CH₃ | OCH₃ |
| Cl | CH₂OCH₃ | H | CH | CH₃ | CH₃ |
| Cl | CH₂OCH₃ | H | CH | CH₃ | OCH₃ |
| Cl | CH₂OCH₃ | H | CH | OCH₃ | OCH₃ |
| Cl | CH₂OCH₃ | H | CH | Cl | OCH₃ |
| Cl | CH₂OCH₃ | H | N | CH₃ | CH₃ |
| Cl | CH₂OCH₃ | H | N | CH₃ | OCH₃ |
| Cl | CH₂OCH₃ | H | N | OCH₃ | OCH₃ |
| Cl | CH₂OCH₃ | H | N | OCH₂CH₃ | NHCH₃ |
| Cl | CH₂OCH₃ | CH₃ | N | CH₃ | OCH₃ |
| CH₃ | (CH₂)₂OCH₃ | H | CH | CH₃ | OCH₃ |
| CH₃ | (CH₂)₂OCH₃ | H | N | CH₃ | OCH₃ |
| F | (CH₂)₂OCH₃ | H | CH | CH₃ | OCH₃ |
| F | (CH₂)₂OCH₃ | H | N | CH₃ | OCH₃ |
| Cl | (CH₂)₂OCH₃ | H | CH | CH₃ | OCH₃ |
| Cl | (CH₂)₂OCH₃ | H | N | CH₃ | OCH₃ |
| Cl | CH₂SCH₃ | H | CH | CH₃ | OCH₃ |
| Cl | CH₂SCH₃ | H | N | CH₃ | OCH₃ |
| Cl | (CH₂)₂SCH₃ | H | CH | CH₃ | OCH₃ |
| Cl | (CH₂)₂SCH₃ | H | N | CH₃ | OCH₃ |
| Cl | CH₂S(O)CH₃ | H | CH | CH₃ | OCH₃ |
| Cl | CH₂S(O)CH₃ | H | N | CH₃ | OCH₃ |
| Cl | CH₂SO₂CH₃ | H | CH | CH₃ | OCH₃ |
| Cl | CH₂SO₂CH₃ | H | N | CH₃ | OCH₃ |
| Cl | CH₂CO₂CH₃ | H | CH | CH₃ | OCH₃ |
| Cl | CH₂CO₂CH₃ | H | N | CH₃ | OCH₃ |

TABLE 9-continued

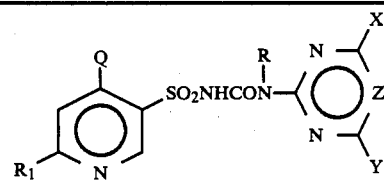

| R₁ | Q | R | Z | X | Y |
|---|---|---|---|---|---|
| Cl | CH₂C(O)N(CH₃)₂ | H | CH | CH₃ | OCH₃ |
| Cl | CH₂C(O)N(CH₃)₂ | H | N | CH₃ | OCH₃ |
| Cl | CH₂CN | H | CH | CH₃ | OCH₃ |
| Cl | CH₂CN | H | N | CH₃ | OCH₃ |
| Cl | CH₂CH=NOCH₃ | H | CH | CH₃ | OCH₃ |
| Cl | CH₂CH=NOCH₃ | H | N | CH₃ | OCH₃ |
| Cl | CH₂C(CH₃)=NOCH₃ | H | CH | CH₃ | OCH₃ |
| Cl | CH₂C(CH₃)=NOCH₃ | H | N | CH₃ | OCH₃ |
| Cl | CH₂-(1,3-dioxolan-2-yl) | H | CH | CH₃ | OCH₃ |
| Cl | CH₂-(1,3-dioxolan-2-yl) | H | N | CH₃ | OCH₃ |
| Cl | CH₂-(1,3-dithiolan-2-yl) | H | CH | CH₃ | OCH₃ |
| Cl | CH₂-(1,3-dithiolan-2-yl) | H | N | CH₃ | OCH₃ |
| Cl | CH₂CH(OCH₃)₂ | H | CH | CH₃ | OCH₃ |
| Cl | CH₂CH(OCH₃)₂ | H | N | CH₃ | OCH₃ |
| Cl | CH₂CH(SCH₃)₂ | H | CH | CH₃ | OCH₃ |
| Cl | CH₂CH(SCH₃)₂ | H | N | CH₃ | OCH₃ |
| Cl | CH₂C(CH₃)(OCH₃)₂ | H | CH | CH₃ | OCH₃ |
| Cl | CH₂C(CH₃)(OCH₃)₂ | H | N | CH₃ | OCH₃ |
| Cl | (CH₂)₂CH(OCH₃)₂ | H | CH | CH₃ | OCH₃ |
| Cl | (CH₂)₂CH(OCH₃)₂ | H | N | CH₃ | OCH₃ |

TABLE 10

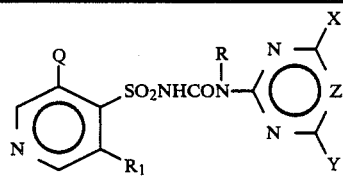

| R₁ | Q | R | Z | X | Y |
|---|---|---|---|---|---|
| H | CH₂OCH₃ | H | CH | CH₃ | CH₃ |
| H | CH₂OCH₃ | H | CH | CH₃ | OCH₃ |
| H | CH₂OCH₃ | H | CH | OCH₃ | OCH₃ |
| H | CH₂OCH₃ | H | CH | Cl | OCH₃ |
| H | CH₂OCH₃ | H | N | CH₃ | CH₃ |
| H | CH₂OCH₃ | H | N | CH₃ | OCH₃ |
| H | CH₂OCH₃ | H | N | OCH₃ | OCH₃ |
| H | CH₂OCH₃ | H | N | OCH₂CH₃ | NHCH₃ |
| H | (CH₂)₂OCH₃ | H | CH | CH₃ | CH₃ |
| H | (CH₂)₂OCH₃ | H | CH | CH₃ | OCH₃ |
| H | (CH₂)₂OCH₃ | H | CH | OCH₃ | OCH₃ |
| H | (CH₂)₂OCH₃ | H | CH | Cl | OCH₃ |
| H | (CH₂)₂OCH₃ | H | N | CH₃ | CH₃ |
| H | (CH₂)₂OCH₃ | H | N | CH₃ | OCH₃ |
| H | (CH₂)₂OCH₃ | H | N | OCH₃ | OCH₃ |

TABLE 10-continued

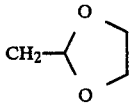

| R₁ | Q | R | Z | X | Y |
|---|---|---|---|---|---|
| H | (CH₂)₂OCH₃ | H | N | OCH₂CH₃ | NHCH₃ |
| H | CH₂OCH₃ | H | CH | CH₃ | OCH₃ |
| H | CH₂OCH₃ | H | N | CH₃ | OCH₃ |
| H | (CH₂)₂SCH₃ | H | CH | CH₃ | OCH₃ |
| H | (CH₂)₂SCH₃ | H | N | CH₃ | OCH₃ |
| H | CH₂SCH₂CH=CH₂ | H | CH | CH₃ | OCH₃ |
| H | CH₂SCH₂CH=CH₂ | H | N | CH₃ | OCH₃ |
| H | (CH₂)₂SCH₂CH=CH₂ | H | CH | CH₃ | OCH₃ |
| H | (CH₂)₂SCH₂CH=CH₂ | H | N | CH₃ | OCH₃ |
| H | CH₂S(O)CH₃ | H | CH | CH₃ | OCH₃ |
| H | CH₂S(O)CH₃ | H | N | CH₃ | OCH₃ |
| H | (CH₂)₂S(O)CH₃ | H | CH | CH₃ | OCH₃ |
| H | (CH₂)₂S(O)CH₃ | H | N | CH₃ | OCH₃ |
| H | CH₂SO₂CH₃ | H | CH | CH₃ | OCH₃ |
| H | CH₂SO₂CH₃ | H | N | CH₃ | OCH₃ |
| H | (CH₂)₂SO₂CH₃ | H | CH | CH₃ | OCH₃ |
| H | (CH₂)₂SO₂CH₃ | H | N | CH₃ | OCH₃ |
| H | CH₂CO₂CH₃ | H | CH | CH₃ | OCH₃ |
| H | CH₂CO₂CH₃ | H | N | CH₃ | OCH₃ |
| H | (CH₂)₂CO₂CH₃ | H | CH | CH₃ | OCH₃ |
| H | (CH₂)₂CO₂CH₃ | H | N | CH₃ | OCH₃ |
| H | CH₂C(O)N(CH₃)₂ | H | CH | CH₃ | OCH₃ |
| H | CH₂C(O)N(CH₃)₂ | H | N | CH₃ | OCH₃ |
| H | (CH₂)₂C(O)N(CH₃)₂ | H | CH | CH₃ | OCH₃ |
| H | (CH₂)₂C(O)N(CH₃)₂ | H | N | CH₃ | OCH₃ |
| H | CH₂CN | H | CH | CH₃ | OCH₃ |
| H | CH₂CN | H | N | CH₃ | OCH₃ |
| H | (CH₂)₂CN | H | CH | CH₃ | OCH₃ |
| H | (CH₂)₂CN | H | N | CH₃ | OCH₃ |
| H | CH₂CH=NOCH₃ | H | CH | CH₃ | OCH₃ |
| H | CH₂CH=NOCH₃ | H | N | CH₃ | OCH₃ |
| H | (CH₂)₂CH=NOCH₃ | H | CH | CH₃ | OCH₃ |
| H | (CH₂)₂CH=NOCH₃ | H | N | CH₃ | OCH₃ |
| H | CH₂C(CH₃)=NOCH₃ | H | CH | CH₃ | OCH₃ |
| H | CH₂C(CH₃)=NOCH₃ | H | N | CH₃ | OCH₃ |
| H | (CH₂)₂C(CH₃)=NOCH₃ | H | CH | CH₃ | OCH₃ |
| H | (CH₂)₂C(CH₃)=NOCH₃ | H | N | CH₃ | OCH₃ |
| H | 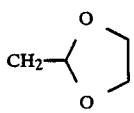 | H | CH | CH₃ | OCH₃ |
| H | 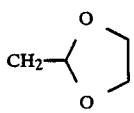 | H | N | CH₃ | OCH₃ |
| H | 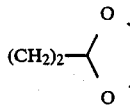 | H | CH | CH₃ | OCH₃ |
| H | 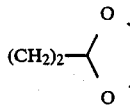 | H | N | CH₃ | OCH₃ |
| H | 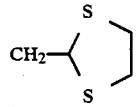 | H | CH | CH₃ | OCH₃ |

TABLE 10-continued

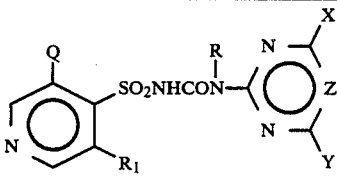

| R₁ | Q | R | Z | X | Y |
|---|---|---|---|---|---|
| H | CH₂–(dithiolane) | H | N | CH₃ | OCH₃ |
| H | (CH₂)₂–(dithiolane) | H | CH | CH₃ | OCH₃ |
| H | (CH₂)₂–(dithiolane) | H | N | CH₃ | OCH₃ |
| H | CH₂CH(OCH₃)₂ | H | CH | CH₃ | OCH₃ |
| H | CH₂CH(OCH₃)₂ | H | N | CH₃ | OCH₃ |
| H | (CH₂)₂CH(OCH₃)₂ | H | CH | CH₃ | OCH₃ |
| H | (CH₂)₂CH(OCH₃)₂ | H | N | CH₃ | OCH₃ |
| H | CH₂CH(SCH₃)₂ | H | CH | CH₃ | OCH₃ |
| H | CH₂CH(SCH₃)₂ | H | N | CH₃ | OCH₃ |
| H | CH₂C(CH₃)(OCH₃)₂ | H | CH | CH₃ | OCH₃ |
| H | CH₂C(CH₃)(OCH₃)₂ | H | N | CH₃ | OCH₃ |
| H | (CH₂)₂C(CH₃)(OCH₃)₂ | H | CH | CH₃ | OCH₃ |
| H | (CH₂)₂C(CH₃)(OCH₃)₂ | H | N | CH₃ | OCH₃ |
| CO₂CH₃ | CH₂OCH₃ | H | CH | CH₃ | OCH₃ |
| CO₂CH₃ | CH₂OCH₃ | H | N | CH₃ | OCH₃ |
| CO₂CH₃ | (CH₂)₂OCH₃ | H | CH | CH₃ | OCH₃ |
| CO₂CH₃ | (CH₂)₂OCH₃ | H | N | CH₃ | OCH₃ |
| CO₂CH₃ | CH₂SCH₃ | H | CH | CH₃ | OCH₃ |
| CO₂CH₃ | CH₂SCH₃ | H | N | CH₃ | OCH₃ |
| CO₂CH₃ | (CH₂)₂SCH₃ | H | CH | CH₃ | OCH₃ |
| CO₂CH₃ | (CH₂)₂SCH₃ | H | N | CH₃ | OCH₃ |
| Cl | CH₂OCH₃ | H | CH | CH₃ | OCH₃ |
| Cl | CH₂OCH₃ | H | N | CH₃ | OCH₃ |
| SCH₃ | CH₂OCH₃ | H | CH | CH₃ | OCH₃ |
| SCH₃ | CH₂OCH₃ | H | N | CH₃ | OCH₃ |

TABLE 11

| R₁ | Q | R | Z | X | Y |
|---|---|---|---|---|---|
| OCH₃ | CH₂OCH₃ | H | CH | CH₃ | CH₃ |
| OCH₃ | CH₂OCH₃ | H | CH | CH₃ | OCH₃ |
| OCH₃ | CH₂OCH₃ | H | CH | OCH₃ | OCH₃ |
| OCH₃ | CH₂OCH₃ | H | CH | Cl | OCH₃ |
| OCH₃ | CH₂OCH₃ | H | N | CH₃ | CH₃ |
| OCH₃ | CH₂OCH₃ | H | N | CH₃ | OCH₃ |
| OCH₃ | CH₂OCH₃ | H | N | OCH₃ | OCH₃ |
| OCH₃ | CH₂OCH₃ | H | N | OCH₂CH₃ | NHCH₃ |
| OCH₃ | CH₂OCH₃ | CH₃ | N | CH₃ | OCH₃ |
| S(O)CH₃ | CH₂OCH₃ | H | CH | CH₃ | CH₃ |
| S(O)CH₃ | CH₂OCH₃ | H | CH | CH₃ | OCH₃ |
| S(O)CH₃ | CH₂OCH₃ | H | CH | OCH₃ | OCH₃ |
| S(O)CH₃ | CH₂OCH₃ | H | CH | Cl | OCH₃ |
| S(O)CH₃ | CH₂OCH₃ | H | N | CH₃ | CH₃ |

TABLE 11-continued

| R₁ | Q | R | Z | X | Y |
|---|---|---|---|---|---|
| S(O)CH₃ | CH₂OCH₃ | H | N | CH₃ | OCH₃ |
| S(O)CH₃ | CH₂OCH₃ | H | N | OCH₃ | OCH₃ |
| S(O)CH₃ | CH₂OCH₃ | H | N | OCH₂CH₃ | NHCH₃ |
| S(O)CH₃ | CH₂OCH₃ | CH₃ | N | CH₃ | OCH₃ |
| N(CH₃)₂ | CH₂OCH₃ | H | CH | CH₃ | CH₃ |
| N(CH₃)₂ | CH₂OCH₃ | H | CH | CH₃ | OCH₃ |
| N(CH₃)₂ | CH₂OCH₃ | H | CH | OCH₃ | OCH₃ |
| N(CH₃)₂ | CH₂OCH₃ | H | CH | Cl | OCH₃ |
| N(CH₃)₂ | CH₂OCH₃ | H | N | CH₃ | CH₃ |
| N(CH₃)₂ | CH₂OCH₃ | H | N | CH₃ | OCH₃ |
| N(CH₃)₂ | CH₂OCH₃ | H | N | OCH₃ | OCH₃ |
| N(CH₃)₂ | CH₂OCH₃ | H | N | OCH₂CH₃ | NHCH₃ |
| N(CH₃)₂ | CH₂OCH₃ | CH₃ | N | CH₃ | OCH₃ |
| CH₃ | (CH₂)₂OCH₃ | H | CH | CH₃ | OCH₃ |
| CH₃ | (CH₂)₂OCH₃ | H | N | CH₃ | OCH₃ |
| S(O)CH₃ | (CH₂)₂OCH₃ | H | CH | CH₃ | OCH₃ |
| S(O)CH₃ | (CH₂)₂OCH₃ | H | N | CH₃ | OCH₃ |
| N(CH₃)₂ | (CH₂)₂OCH₃ | H | CH | CH₃ | OCH₃ |
| N(CH₃)₂ | (CH₂)₂OCH₃ | H | N | CH₃ | OCH₃ |
| OCH₃ | CH₂SCH₃ | H | CH | CH₃ | OCH₃ |
| OCH₃ | CH₂SCH₃ | H | N | CH₃ | OCH₃ |
| OCH₃ | (CH₂)₂SCH₃ | H | CH | CH₃ | OCH₃ |
| OCH₃ | (CH₂)₂SCH₃ | H | N | CH₃ | OCH₃ |
| OCH₃ | CH₂S(O)CH₃ | H | CH | CH₃ | OCH₃ |
| OCH₃ | CH₂S(O)CH₃ | H | N | CH₃ | OCH₃ |
| OCH₃ | CH₂SO₂CH₃ | H | CH | CH₃ | OCH₃ |
| OCH₃ | CH₂SO₂CH₃ | H | N | CH₃ | OCH₃ |
| OCH₃ | CH₂CO₂CH₃ | H | CH | CH₃ | OCH₃ |
| OCH₃ | CH₂CO₂CH₃ | H | N | CH₃ | OCH₃ |
| OCH₃ | CH₂C(O)N(CH₃)₂ | H | CH | CH₃ | OCH₃ |
| OCH₃ | CH₂C(O)N(CH₃)₂ | H | N | CH₃ | OCH₃ |
| OCH₃ | CH₂CN | H | CH | CH₃ | OCH₃ |
| OCH₃ | CH₂CN | H | N | CH₃ | OCH₃ |
| OCH₃ | CH₂CH=NOCH₃ | H | CH | CH₃ | OCH₃ |
| OCH₃ | CH₂CH=NOCH₃ | H | N | CH₃ | OCH₃ |
| OCH₃ | CH₂C(CH₃)=NOCH₃ | H | CH | CH₃ | OCH₃ |
| OCH₃ | CH₂C(CH₃)=NOCH₃ | H | N | CH₃ | OCH₃ |
| OCH₃ | CH₂-CH(O-CH₂CH₂-O) (1,3-dioxolane) | H | CH | CH₃ | OCH₃ |
| OCH₃ | CH₂-CH(O-CH₂CH₂-O) (1,3-dioxolane) | H | N | CH₃ | OCH₃ |
| OCH₃ | CH₂-CH(S-CH₂CH₂-S) (1,3-dithiolane) | H | CH | CH₃ | OCH₃ |
| OCH₃ | CH₂-CH(S-CH₂CH₂-S) (1,3-dithiolane) | H | N | CH₃ | OCH₃ |
| OCH₃ | CH₂CH(OCH₃)₂ | H | CH | CH₃ | OCH₃ |
| OCH₃ | CH₂CH(OCH₃)₂ | H | N | CH₃ | OCH₃ |
| OCH₃ | CH₂CH(SCH₃)₂ | H | CH | CH₃ | OCH₃ |
| OCH₃ | CH₂CH(SCH₃)₂ | H | N | CH₃ | OCH₃ |
| OCH₃ | CH₂C(CH₃)(OCH₃)₂ | H | CH | CH₃ | OCH₃ |
| OCH₃ | CH₂C(CH₃)(OCH₃)₂ | H | N | CH₃ | OCH₃ |
| OCH₃ | (CH₂)₂CH(OCH₃)₂ | H | CH | CH₃ | OCH₃ |

TABLE 11-continued

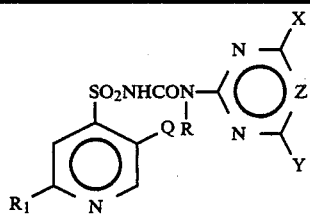

| R₁ | Q | R | Z | X | Y |
|---|---|---|---|---|---|
| OCH₃ | (CH₂)₂CH(OCH₃)₂ | H | N | CH₃ | OCH₃ |

TABLE 12

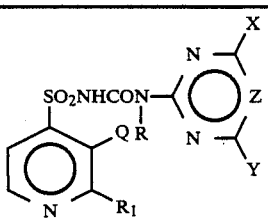

| R₁ | Q | R | Z | X | Y |
|---|---|---|---|---|---|
| OCH₃ | CH₂OCH₃ | H | CH | CH₃ | CH₃ |
| OCH₃ | CH₂OCH₃ | H | CH | CH₃ | OCH₃ |
| OCH₃ | CH₂OCH₃ | H | CH | OCH₃ | OCH₃ |
| OCH₃ | CH₂OCH₃ | H | CH | Cl | OCH₃ |
| OCH₃ | CH₂OCH₃ | H | N | CH₃ | CH₃ |
| OCH₃ | CH₂OCH₃ | H | N | CH₃ | OCH₃ |
| OCH₃ | CH₂OCH₃ | H | N | OCH₃ | OCH₃ |
| OCH₃ | CH₂OCH₃ | H | N | OCH₂CH₃ | NHCH₃ |
| OCH₃ | CH₂OCH₃ | CH₃ | N | CH₃ | OCH₃ |
| S(O)CH₃ | CH₂OCH₃ | H | CH | CH₃ | CH₃ |
| S(O)CH₃ | CH₂OCH₃ | H | CH | CH₃ | OCH₃ |
| S(O)CH₃ | CH₂OCH₃ | H | CH | OCH₃ | OCH₃ |
| S(O)CH₃ | CH₂OCH₃ | H | CH | Cl | OCH₃ |
| S(O)CH₃ | CH₂OCH₃ | H | N | CH₃ | CH₃ |
| S(O)CH₃ | CH₂OCH₃ | H | N | CH₃ | OCH₃ |
| S(O)CH₃ | CH₂OCH₃ | H | N | OCH₃ | OCH₃ |
| S(O)CH₃ | CH₂OCH₃ | H | N | OCH₂CH₃ | NHCH₃ |
| S(O)CH₃ | CH₂OCH₃ | CH₃ | N | CH₃ | OCH₃ |
| N(CH₃)₂ | CH₂OCH₃ | H | CH | CH₃ | CH₃ |
| N(CH₃)₂ | CH₂OCH₃ | H | CH | CH₃ | OCH₃ |
| N(CH₃)₂ | CH₂OCH₃ | H | CH | OCH₃ | OCH₃ |
| N(CH₃)₂ | CH₂OCH₃ | H | CH | Cl | OCH₃ |
| N(CH₃)₂ | CH₂OCH₃ | H | N | CH₃ | CH₃ |
| N(CH₃)₂ | CH₂OCH₃ | H | N | CH₃ | OCH₃ |
| N(CH₃)₂ | CH₂OCH₃ | H | N | OCH₃ | OCH₃ |
| N(CH₃)₂ | CH₂OCH₃ | H | N | OCH₂CH₃ | NHCH₃ |
| N(CH₃)₂ | CH₂OCH₃ | CH₃ | N | CH₃ | OCH₃ |
| CH₃ | (CH₂)₂OCH₃ | H | CH | CH₃ | OCH₃ |
| CH₃ | (CH₂)₂OCH₃ | H | N | CH₃ | OCH₃ |
| S(O)CH₃ | (CH₂)₂OCH₃ | H | CH | CH₃ | OCH₃ |
| S(O)CH₃ | (CH₂)₂OCH₃ | H | N | CH₃ | OCH₃ |
| N(CH₃)₂ | (CH₂)₂OCH₃ | H | CH | CH₃ | OCH₃ |
| N(CH₃)₂ | (CH₂)₂OCH₃ | H | N | CH₃ | OCH₃ |
| OCH₃ | CH₂SCH₃ | H | CH | CH₃ | OCH₃ |
| OCH₃ | CH₂SCH₃ | H | N | CH₃ | OCH₃ |
| OCH₃ | (CH₂)₂SCH₃ | H | CH | CH₃ | OCH₃ |
| OCH₃ | (CH₂)₂SCH₃ | H | N | CH₃ | OCH₃ |
| OCH₃ | CH₂S(O)CH₃ | H | CH | CH₃ | OCH₃ |
| OCH₃ | CH₂S(O)CH₃ | H | N | CH₃ | OCH₃ |
| OCH₃ | CH₂SO₂CH₃ | H | CH | CH₃ | OCH₃ |
| OCH₃ | CH₂SO₂CH₃ | H | N | CH₃ | OCH₃ |
| OCH₃ | CH₂CO₂CH₃ | H | CH | CH₃ | OCH₃ |
| OCH₃ | CH₂CO₂CH₃ | H | N | CH₃ | OCH₃ |
| OCH₃ | CH₂C(O)N(CH₃)₂ | H | CH | CH₃ | OCH₃ |
| OCH₃ | CH₂C(O)N(CH₃)₂ | H | N | CH₃ | OCH₃ |
| OCH₃ | CH₂CN | H | CH | CH₃ | OCH₃ |
| OCH₃ | CH₂CN | H | N | CH₃ | OCH₃ |
| OCH₃ | CH₂CH=NOCH₃ | H | CH | CH₃ | OCH₃ |
| OCH₃ | CH₂CH=NOCH₃ | H | N | CH₃ | OCH₃ |
| OCH₃ | CH₂C(CH₃)=NOCH₃ | H | CH | CH₃ | OCH₃ |
| OCH₃ | CH₂C(CH₃)=NOCH₃ | H | N | CH₃ | OCH₃ |

TABLE 12-continued

Structure: pyridine with R₁ at 2-position, SO₂NHCON(R)- at 4-position, Q-O at 3-position, connected to pyrimidine/triazine ring with X, Y, Z substituents.

| R₁ | Q | R | Z | X | Y |
|---|---|---|---|---|---|
| OCH₃ | CH₂ with 1,3-dioxolane | H | CH | CH₃ | OCH₃ |
| OCH₃ | CH₂ with 1,3-dioxolane | H | N | CH₃ | OCH₃ |
| OCH₃ | CH₂ with 1,3-dithiolane | H | CH | CH₃ | OCH₃ |
| OCH₃ | CH₂ with 1,3-dithiolane | H | N | CH₃ | OCH₃ |
| OCH₃ | CH₂CH(OCH₃)₂ | H | CH | CH₃ | OCH₃ |
| OCH₃ | CH₂CH(OCH₃)₂ | H | N | CH₃ | OCH₃ |
| OCH₃ | CH₂CH(SCH₃)₂ | H | CH | CH₃ | OCH₃ |
| OCH₃ | CH₂CH(SCH₃)₂ | H | N | CH₃ | OCH₃ |
| OCH₃ | CH₂C(CH₃)(OCH₃)₂ | H | CH | CH₃ | OCH₃ |
| OCH₃ | CH₂C(CH₃)(OCH₃)₂ | H | N | CH₃ | OCH₃ |
| OCH₃ | (CH₂)₂CH(OCH₃)₂ | H | CH | CH₃ | OCH₃ |
| OCH₃ | (CH₂)₂CH(OCH₃)₂ | H | N | CH₃ | OCH₃ |

TABLE 13

Structure: pyridine with R₁, Q at 3-position, SO₂NHCONH-A at 2-position.

| R₁ | Q | A |
|---|---|---|
| H | CH₂OCH₃ | 4-methoxy-furo[2,3-d] pyrimidine derivative |
| H | CH₂OCH₃ | 4-methyl-furo[2,3-d] pyrimidine derivative |
| H | CH₂OCH₃ | 4-methyl-2-methyl-(methylfurano)pyrimidine |
| H | CH₂OCH₃ | 4-methoxy-(methylfurano)pyrimidine |
| H | CH₂OCH₃ | 4-methyl-(methylfurano)pyrimidine |
| H | CH₂OCH₃ | 4-methyl-(methoxyfurano)pyrimidine |
| H | CH₂OCH₃ | N—N—CH₃ / OCH₃ triazole derivative |

TABLE 13-continued
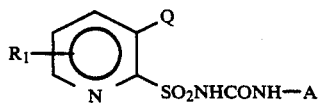
| R₁ | Q | A |
|---|---|---|
| H | CH₂OCH₃ | 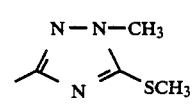 |
| H | CH₂OCH₃ | 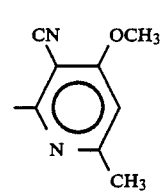 |
| H | CH₂OCH₃ | 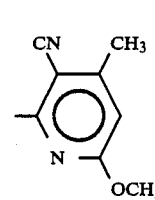 |
| H | CH₂OCH₃ | 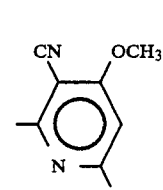 |
TABLE 14
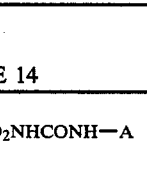
| R₁ | Q | A |
|---|---|---|
| H | CH₂OCH₃ | 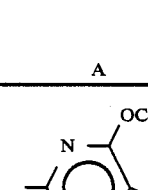 |
| H | CH₂OCH₃ | 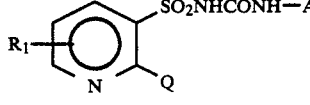 |
TABLE 14-continued
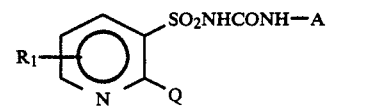
| R₁ | Q | A |
|---|---|---|
| H | CH₂OCH₃ | 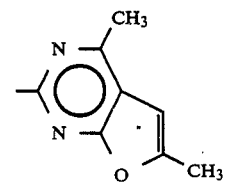 |
| H | CH₂OCH₃ | 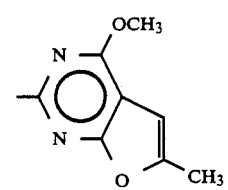 |
| H | CH₂OCH₃ | 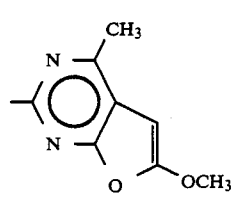 |
| H | CH₂OCH₃ | 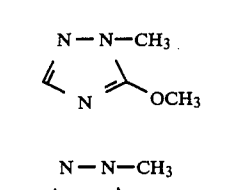 |
| H | CH₂OCH₃ | 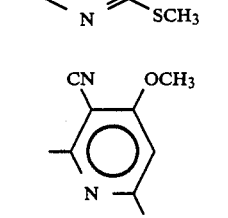 |
| H | CH₂OCH₃ | 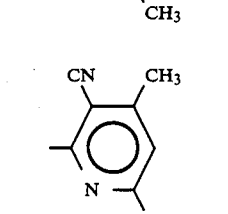 |
| H | CH₂OCH₃ | 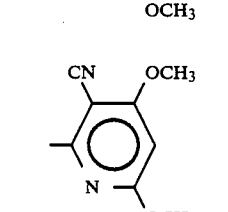 |
| H | CH₂OCH₃ | 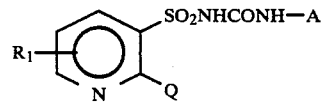 |

TABLE 15

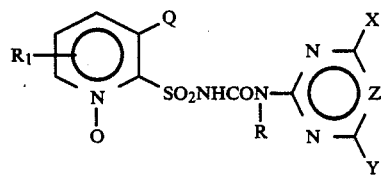

| R₁ | Q | R | Z | X | Y | m.p. (°C.) |
|---|---|---|---|---|---|---|
| H | CH₂OCH₃ | H | CH | CH₃ | CH₃ | |
| H | CH₂OCH₃ | H | CH | CH₃ | OCH₃ | |
| H | CH₂OCH₃ | H | CH | OCH₃ | OCH₃ | |
| H | CH₂OCH₃ | H | CH | Cl | OCH₃ | |
| H | CH₂OCH₃ | H | N | CH₃ | CH₃ | |
| H | CH₂OCH₃ | H | N | CH₃ | OCH₃ | |
| H | CH₂OCH₃ | H | N | OCH₃ | OCH₃ | |
| H | CH₂OCH₃ | H | N | OCH₂CH₃ | NHCH₃ | |
| H | (CH₂)₂OCH₃ | H | CH | CH₃ | CH₃ | |
| H | (CH₂)₂OCH₃ | H | CH | CH₃ | OCH₃ | |
| H | (CH₂)₂OCH₃ | H | CH | OCH₃ | OCH₃ | |
| H | (CH₂)₂OCH₃ | H | CH | Cl | OCH₃ | |
| H | (CH₂)₂OCH₃ | H | N | CH₃ | CH₃ | |
| H | (CH₂)₂OCH₃ | H | N | CH₃ | OCH₃ | |
| H | (CH₂)₂OCH₃ | H | N | OCH₃ | OCH₃ | |
| H | (CH₂)₂OCH₃ | H | N | OCH₂CH₃ | NHCH₃ | |
| H | CH₂SCH₃ | H | CH | CH₃ | CH₃ | |
| H | CH₂SCH₃ | H | CH | CH₃ | OCH₃ | |
| H | CH₂SCH₃ | H | CH | OCH₃ | OCH₃ | |
| H | CH₂SCH₃ | H | CH | Cl | OCH₃ | |
| H | CH₂SCH₃ | H | N | CH₃ | CH₃ | |
| H | CH₂SCH₃ | H | N | CH₃ | OCH₃ | |
| H | CH₂SCH₃ | H | N | OCH₃ | OCH₃ | |
| H | CH₂SCH₃ | H | N | OCH₂CH₃ | NHCH₃ | |
| H | (CH₂)₂SCH₃ | H | CH | CH₃ | CH₃ | |
| H | (CH₂)₂SCH₃ | H | CH | CH₃ | OCH₃ | |
| H | (CH₂)₂SCH₃ | H | CH | OCH₃ | OCH₃ | |
| H | (CH₂)₂SCH₃ | H | CH | Cl | OCH₃ | |
| H | (CH₂)₂SCH₃ | H | N | CH₃ | CH₃ | |
| H | (CH₂)₂SCH₃ | H | N | CH₃ | OCH₃ | |
| H | (CH₂)₂SCH₃ | H | N | OCH₃ | OCH₃ | |
| H | (CH₂)₂SCH₃ | H | N | OCH₂CH₃ | NHCH₃ | |
| H | CH₂S(O)CH₃ | H | CH | CH₃ | OCH₃ | |
| H | CH₂S(O)CH₃ | H | N | CH₃ | OCH₃ | |
| H | (CH₂)₂S(O)CH₃ | H | CH | CH₃ | OCH₃ | |
| H | (CH₂)₂S(O)CH₃ | H | N | CH₃ | OCH₃ | |
| H | CH₂SO₂CH₃ | H | CH | CH₃ | OCH₃ | |
| H | CH₂SO₂CH₃ | H | N | CH₃ | OCH₃ | |
| H | (CH₂)₂SO₂CH₃ | H | CH | CH₃ | OCH₃ | |
| H | (CH₂)₂SO₂CH₃ | H | N | CH₃ | OCH₃ | |
| H | CH₂CO₂CH₃ | H | CH | CH₃ | OCH₃ | |
| H | CH₂CO₂CH₃ | H | N | CH₃ | OCH₃ | |
| H | (CH₂)₂CO₂CH₃ | H | CH | CH₃ | OCH₃ | |
| H | (CH₂)₂CO₂CH₃ | H | N | CH₃ | OCH₃ | |
| H | CH₂C(O)N(CH₃)₂ | H | CH | CH₃ | OCH₃ | |
| H | CH₂C(O)N(CH₃)₂ | H | N | CH₃ | OCH₃ | |
| H | (CH₂)₂C(O)N(CH₃)₂ | H | CH | CH₃ | OCH₃ | |
| H | (CH₂)₂C(O)N(CH₃)₂ | H | N | CH₃ | OCH₃ | |
| H | CH₂CN | H | CH | CH₃ | OCH₃ | |
| H | CH₂CN | H | N | CH₃ | OCH₃ | |
| H | (CH₂)₂CN | H | CH | CH₃ | OCH₃ | |
| H | (CH₂)₂CN | H | N | CH₃ | OCH₃ | |
| H | CH₂CH=NOCH₃ | H | CH | CH₃ | OCH₃ | |
| H | CH₂CH=NOCH₃ | H | N | CH₃ | OCH₃ | |
| H | (CH₂)₂CH=NOCH₃ | H | CH | CH₃ | OCH₃ | |
| H | (CH₂)₂CH=NOCH₃ | H | N | CH₃ | OCH₃ | |
| H | CH₂C(CH₃)=NOCH₃ | H | CH | CH₃ | OCH₃ | |
| H | CH₂C(CH₃)=NOCH₃ | H | N | CH₃ | OCH₃ | |
| H | CH(OH)CH₂CH₃ | H | CH | CH₃ | CH₃ | 108–111 |
| H | CH(OH)CH₂CH₃ | H | CH | OCH₃ | OCH₃ | 130–134 |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

|  | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual". MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Lickenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 2

| Wettable Powder |  |
|---|---|
| N-[(4,6-dimethoxypyrimidin-2-yl)aminocarbonyl]-3-(methylthiomethyl)-2-pyridinesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 3

| Wettable Powder |  |
|---|---|
| N-[(4,6-dimethoxypyrimidin-2-yl)aminocarbonyl]-3-(methylthiomethyl)-2-pyridinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

| Granule |  |
|---|---|
| Wettable Powder of Example 3 | 5% |
| attapulgite granules (U.S.S. 20-40 mesh: 0.84-0.42 mm) | 95% |

A slurry of wettable powder containing 25% solids is sprayed on the surface of attapulgite granules in a double-cone blender. The granules are dried and packaged.

EXAMPLE 5

| Extruded Pellet |  |
|---|---|
| N-[(4,6-dimethoxypyrimidin-2-yl)aminocarbonyl]-3-(methylthiomethyl)-2-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

| Low Strength Granule | |
|---|---|
| N-[(4,6-dimethoxypyrimidin-2-yl)aminocarbonyl]-3-(methylthiomethyl)-2-pyridinesulfonamide | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE 7

| Granule | |
|---|---|
| N-[(4,6-dimethoxypyrimidin-2-yl)aminocarbonyl]-3-(methylthiomethyl)-2-pyridinesulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 8

| Low Strength Granule | |
|---|---|
| N-[(4,6-dimethoxypyrimidin-2-yl)aminocarbonyl]-3-(methylthiomethyl)-2-pyridinesulfonamide | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

| Aqueous Suspension | |
|---|---|
| N-[(4,6-dimethoxypyrimidin-2-yl)aminocarbonyl]-3-(methylthiomethyl)-2-pyridinesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 10

| Solution | |
|---|---|
| N-[(4,6-dimethoxypyrimidin-2-yl)aminocarbonyl]-3-(methylthiomethyl)-2-pyridinesulfonamide, ammonium salt | 5% |
| water | 95% |

The salt is added directly to the water with stirring to produce the solution, which may then be packaged for use.

EXAMPLE 11

| High Strength Concentrate | |
|---|---|
| N-[(4,6-dimethoxypyrimidin-2-yl)aminocarbonyl]-3-(methylthiomethyl)-2-pyridinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 12

| Wettable Powder | |
|---|---|
| N-[(4,6-dimethoxypyrimidin-2-yl)aminocarbonyl]-3-(methylthiomethyl)-2-pyridinesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 13

| Wettable Powder | |
|---|---|
| N-[(4,6-dimethoxypyrimidin-2-yl)aminocarbonyl]-3-(methylthiomethyl)-2-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 14

| Oil Suspension | |
|---|---|
| N-[(4,6-dimethoxypyrimidin-2-yl)aminocarbonyl]-3-(methylthiomethyl)-2-pyridinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 15

| Dust | |
|---|---|
| N-[(4,6-dimethoxypyrimidin-2-yl)aminocarbonyl]-3-(methylthiomethyl)-2-pyridinesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 16

| Oil Suspension | |
|---|---|
| N-[(4,6-dimethoxypyrimidin-2-yl)aminocarbonyl]-3-(methylthiomethyl)-2-pyridinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

UTILITY

Test results indicate that the compounds of the present invention are highly active preemergent or postemergent herbicides or plant growth regulants. Many of them have utility for broad-spectrum pre- and or postemergence weed control in areas where complete control of all vegetation is desired, such as around fuel storage tanks, industrial storage areas, parking lots, drive-in theaters, around billboards, highway and railroad structures. Some of the compounds have utility for selective weed control in crops such as rice, wheat, barley, corn, soybeans and cotton. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium and imidazolinone types.

The herbicidal properties of the subject compounds were discovered in a number of greenhouse tests. The test procedures and results follow.

Compounds

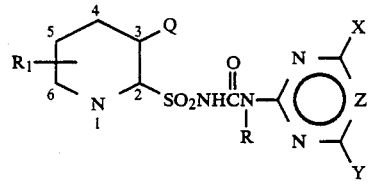

| Compound | Q | $R_1$ | R | X | Y | Z |
|---|---|---|---|---|---|---|
| 1 | $CH_2SCH_3$ | H | H | $CH_3$ | $CH_3$ | CH |
| 2 | $CH_2SCH_3$ | H | H | $CH_3$ | $OCH_3$ | CH |
| 3 | $CH_2SCH_3$ | H | H | $OCH_3$ | $OCH_3$ | CH |
| 4 | $CH_2SCH_3$ | H | H | Cl | $OCH_3$ | CH |
| 5 | $CH_2SO_2CH_3$ | H | H | $OCH_3$ | $OCH_3$ | CH |
| 6 | $CH_2SO_2CH_3$ | H | H | Cl | $OCH_3$ | CH |
| 7 | $CH_2SO_2CH_3$ | H | H | $CH_3$ | $CH_3$ | CH |
| 8 | $CH_2SO_2CH_3$ | H | H | $CH_3$ | $OCH_3$ | CH |
| 9 | $CH_2OCH_3$ | H | H | $OCH_3$ | $OCH_3$ | CH |
| 10 | $CH_2OCH_3$ | H | H | $CH_3$ | $OCH_3$ | N |
| 11 | $CH_2OCH_3$ | H | H | $OCH_3$ | $OCH_3$ | N |
| 12 | $CH_2OCH_3$ | H | H | Cl | $OCH_3$ | CH |
| 13 | $CH_2OCH_3$ | H | H | $OC_2H_5$ | $NHCH_3$ | N |
| 14 | $CH_2OCH_3$ | 6-Cl | H | $OCH_3$ | $OCH_3$ | CH |
| 15 | $CH_2OCH_3$ | 6-Cl | H | $CH_3$ | $OCH_3$ | CH |
| 16 | $CH_2OCH_3$ | 6-Cl | H | Cl | $OCH_3$ | CH |
| 17 | $CH_2OCH_3$ | 6-Cl | H | $CH_3$ | $CH_3$ | CH |
| 18 | $CH_2OCH_3$ | 6-Cl | H | $OCH_3$ | $OCH_3$ | N |
| 19 | $CH_2OCH_3$ | 6-Cl | H | $CH_3$ | $OCH_3$ | N |
| 20 | $CH_2OCH_3$ | 6-Cl | H | $OC_2H_5$ | $NHCH_3$ | N |
| 21 | $CH_2OCH_3$ | 6-Cl | $CH_3$ | $CH_3$ | $OCH_3$ | N |
| 22 | $CH_2OCH_3$ | 6-Cl | $CH_3$ | $OCH_3$ | $OCH_3$ | CH |
| 23 | $CH_2OCH_3$ | 5-Cl | H | $OCH_3$ | $OCH_3$ | CH |
| 24 | $CH_2OCH_3$ | 5-Cl | H | $CH_3$ | $OCH_3$ | CH |
| 25 | $CH_2OCH_3$ | 5-Cl | H | $OCH_3$ | $OCH_3$ | N |
| 26 | $CH_2OCH_2CH_3$ | H | H | $OCH_3$ | $OCH_3$ | CH |

-continued

Compounds

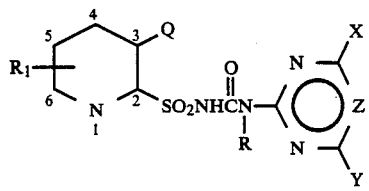

| Compound | Q | R₁ | R | X | Y | Z |
|---|---|---|---|---|---|---|
| 27 | CH₂OCH₂CH₃ | H | H | OCH₃ | OCH₃ | N |
| 28 | CH₂OCH₂CH₃ | H | H | CH₃ | OCH₃ | N |
| 29 | CH₂OCH₂CH₃ | H | H | CH₃ | OCH₃ | CH |
| 30 | CH₂SCH₂CH₃ | H | H | CH₃ | OCH₃ | CH |
| 31 | CH₂SCH₂CH₃ | H | H | OCH₃ | OCH₃ | CH |
| 32 | CH₂SCH₂CH₃ | H | H | CH₃ | OCH₃ | N |
| 33 | CH₂SCH₂CH₃ | H | H | Cl | OCH₃ | CH |
| 34 | CH₂SCH₂CH₃ | H | H | CH₃ | CH₃ | CH |
| 35 | CH₂SCH₂CH₂CH₃ | H | H | CH₃ | OCH₃ | CH |
| 36 | CH₂SCH₂CH₂CH₃ | H | H | OCH₃ | OCH₃ | CH |
| 37 | CH₂SCH₂CH₂CH₃ | H | H | CH₃ | OCH₃ | N |
| 38 | CH₂SCH₂CH₂CH₃ | H | H | Cl | OCH₃ | CH |
| 39 | CH₂SCH₂CH₂CH₃ | H | H | CH₃ | OCH₃ | CH |
| 40 | CH(CH₃)SCH₃ | H | H | OCH₃ | OCH₃ | N |
| 41 | CH(CH₃)SCH₃ | H | H | CH₃ | OCH₃ | N |
| 42 | CH(CH₃)SCH₃ | H | H | OCH₃ | OCH₃ | CH |
| 43 | CH(CH₃)SCH₃ | H | H | Cl | OCH₃ | CH |
| 44 | CH(CH₃)SCH₃ | H | H | CH₃ | CH₃ | CH |
| 45 | CH(CH₃)SCH₃ | H | H | CH₃ | OCH₃ | CH |
| 46 | CH₂SO₂CH₂CH₂CH₃ | H | H | OCH₃ | OCH₃ | N |
| 47 | CH₂SO₂CH₂CH₂CH₃ | H | H | OCH₃ | OCH₃ | CH |
| 48 | CH₂SO₂CH₂CH₂CH₃ | H | H | CH₃ | OCH₃ | CH |
| 49 | CH₂SO₂CH₂CH₂CH₃ | H | H | CH₃ | OCH₃ | N |
| 50 | CH₂SO₂CH₂CH₂CH₃ | H | H | OCH₃ | OCH₃ | CH |
| 51 | CH₂SO₂CH₂CH₂CH₃ | H | H | OCH₃ | OCH₃ | N |
| 52 | CH₂C(O)N(CH₃)₂ | H | H | OCH₃ | OCH₃ | CH |
| 53 | CH(OH)CH(CH₃)₂ | H | H | CH₃ | CH₃ | CH |
| 54 | CH(OH)CH(CH₃)₂ | H | H | CH₃ | OCH₃ | CH |
| 55 | CH(OH)CH(CH₃)₂ | H | H | OCH₃ | OCH₃ | CH |
| 56 | CH(OH)CH(CH₃)₂ | H | H | CH₃ | OCH₃ | N |
| 57 | CH(OH)CH(CH₃)₂ | H | H | OCH₃ | OCH₃ | N |
| 58 | CH(OH)CH(CH₃)₂ | H | H | Cl | OCH₃ | CH |
| 59 | CH₂CO₂CH₃ | H | H | OCH₃ | OCH₃ | CH |
| 60 | CH₂CO₂CH₃ | H | H | CH₃ | OCH₃ | CH |
| 61 | CH₂CO₂CH₃ | H | H | Cl | OCH₃ | CH |

TEST A

Seeds of crabgrass (Digitaria sp.), barnyard-grass (Echinochloa crusgalli), giant foxtail (Setaria Faberi), wild oats (Avena fatua), cheatgrass (Bromus secalinus), velvetleaf (Abutilon theophrasti), morningglory (Ipomoea spp.), cocklebur (Xanthium pennsylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis or necrosis;
B=burn
D=defoliation
E=emergence inhibition;
G=growth retardation;
H=formative effects;
U=unusual pigmentation
X=axillary stimulation; and
S=albinism
6Y=abscised buds or flowers.

TABLE A

| RATE = KG/HA | CMPD 1 | | CMPD 2 | | CMPD 3 | | CMPD 4 | | CMPD 5 | | CMPD 6 | | CMPD 7 | | CMPD 8 | |
|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSOL | | | | | | | | | | | | | | | | |
| COTTON | 3C,5G | 0 | 10C | 4C,9G | 9C | 4C,9H | 3C,7H | 2C | 0 | 0 | 2C,5G | 0 | 2C,6G | 2C,9H | 1H | 0 |
| MORNING GLORY | 3C,5G | 1C | 4C,9G | 3C,9G | 9C | 5C,9G | 3C,5H | 1C | 3H | 0 | 4C,8H | 3C,5G | 10C | 4C,9G | 3C,7H | 3G |
| COCKLEBUR | 2C,8G | 2H | 3C,8H | 3C,8H | 10C | 4C,9G | 7H | 0 | 0 | 0 | 4C,8H | 2H | 9C | 3C,9H | 1H | 1H |
| NUTSEDGE | 0 | 0 | 3C,7G | 2G | 10C | 9G | 0 | 7G | 3G | 0 | 2C,6G | 0 | 3C,9G | 3C,8G | 2C | 0 |
| CRABGRASS | 0 | 0 | 5G | 2G | 5C,9G | 3C,8G | 3C,5G | 0 | 0 | 0 | 6G | 0 | 3C,8G | 3C,6G | 0 | 0 |
| BARNYARD GRASS | 6H | 0 | 3C,7H | 3H | 6C,9G | 9C | 3C,9G | 2G | 0 | 0 | 3C,9H | 2C,3G | 9C | 9C | 3C,8H | 3H |
| WILD OATS | 2G | 0 | 3C,6G | 0 | 9C | 2C,8G | 5G | 2C,3H | 3H | 0 | 9G | 2C,7G | 4C,9G | 2C,9G | 2C | 0 |
| WHEAT | 3G | 0 | 9G | 5G | 5C,9G | 4C,9G | 5G | 5G | 0 | 0 | 9G | 6G | 9C | 5C,9G | 3G | 0 |
| CORN | 0 | 0 | 2C,4G | 0 | 9C | 3C,9H | 0 | 5G | 5G | 0 | 1C,3G | 0 | 3C,9G | 9C | 1C | 0 |
| SOYBEAN | 0 | 0 | 3C,8G | 6G | 10C | 4C,9G | 2C,2H | 0 | 0 | 0 | 4C,8H | 3C,6G | 6C,9G | 4C,9H | 2H | 0 |
| RICE | 3C,9G | 3G | 4C,9G | 7G | 6C,9G | 5C,9G | 5C,9G | 2G | 2C,7G | 0 | 5C,9G | 3C,6G | 9C | 9C | 3C,9G | 2C,2G |
| SORGHUM | 2C,5G | 0 | 3C,6H | 2G | 9C | 4C,9G | 3C,9G | 7G | 2G | 0 | 3C,9G | 5G | 3C,9G | 2C,9G | 4C,9G | 3C,9H |
| CHEATGRASS | 8G | 0 | 2C,8G | 2C,8G | 9C | 5C,9G | 9G | 6G | 8G | 4G | 2C,9G | 7G | 9C | 9C | 6G | 2G |
| SUGAR BEETS | 1C | 0 | 4C,9G | 2H | 9C | 9C | 3C,7H | 2G | 0 | 0 | 4C,9G | 3C,7G | 10C | 10C | 0 | 2H |
| VELVETLEAF | 3C,7G | 2H | 3C,8H | 7G | 10C | 9C | 7G | 2C,3G | 5G | 0 | 3C,8H | 4G | 9C | 4C,9G | 3C,8H | 0 |
| GIANT FOXTAIL | 3C,4G | 0 | 3C,8G | 3C,8G | 10C | 9C | 3C,9G | 2C,2H | 0 | 0 | 4C,9G | 2C,5G | 9C | 4C,9G | 3G | 0 |
| BARLEY | 0 | 0 | 7G | 5G | 9C | 5C,9G | — | 5G | 0 | 0 | 3C,8G | 2C,5G | 6C,9G | 3C,9G | 3C,4G | 0 |
| PRSOL | | | | | | | | | | | | | | | | |
| COTTON | 0 | 0 | 2G | 0 | 7G | 0 | 0 | 0 | 0 | 0 | 0 | 0 | 2C,6G | 5G | 0 | 0 |
| MORNING GLORY | 0 | 0 | 0 | 0 | 8G | 0 | 0 | 0 | 0 | 0 | 2G | 0 | 2C,8G | 2C,7H | 1C | 0 |
| COCKLEBUR | 0 | 0 | 2G | 0 | 3C,4H | 2H | 2H | — | 0 | 0 | 0 | 0 | 3C,8G | 2C,2H | 8H | 4G |
| NUTSEDGE | — | 0 | 0 | 0 | 2C,9G | 0 | 0 | 0 | 0 | 0 | 0 | 0 | 10E | 6C,9G | 0 | 0 |
| CRABGRASS | 0 | 0 | 2G | 0 | 9H | 2G | 2G | 0 | 0 | 0 | 0 | 0 | 3C,7G | 2C,2H | 2C,2G | 0 |
| BARNYARD GRASS | 0 | 0 | 0 | 0 | 9H | 0 | 0 | 0 | 0 | 0 | 0 | 0 | 3C,9H | 2C,8G | 3G | 0 |
| WILD OATS | 0 | 0 | 0 | 0 | 6G | 0 | 0 | 0 | 0 | 0 | 0 | 0 | 9H | 7G | 2G | 0 |
| WHEAT | 0 | 0 | 0 | 0 | 8G | 0 | 0 | 0 | 0 | 0 | 0 | 0 | 3C,8H | 3C,5G | 2C | 0 |
| CORN | 0 | 0 | 2G | 0 | 3C,9H | 0 | 0 | 0 | 0 | 0 | 0 | 0 | 3C,8H | 5H | 3C,3G | 0 |
| SOYBEAN | 0 | 0 | 0 | 0 | 3C,8G | 0 | 2C,7G | 0 | 0 | 0 | 2G | 0 | 5C,9G | 4C,9H | 3C,8H | 3C,5G |
| RICE | 4G | 0 | 0 | 0 | 9H | 0 | 3C,7G | 0 | 2G | 0 | 2G | 0 | 2C,9G | 3C,9H | 2G | 0 |
| SORGHUM | 0 | 0 | 2G | 0 | 3C,9H | 0 | 2G | 0 | 3G | 0 | 0 | 0 | 5C,9G | 8G | 3C,8H | 0 |
| CHEATGRASS | 2G | 0 | 0 | 0 | 9H | 2H | 2H | 0 | 0 | 0 | 0 | 0 | 5C,9G | 4C,8G | 2G | 3H |
| SUGAR BEETS | 0 | 0 | 0 | 0 | 5C,9G | 1H | 1H | 0 | 0 | 0 | 0 | 0 | 3C,8G | 2C | 3H | 0 |
| VELVETLEAF | 0 | 0 | 3G | 0 | 3C,4G | 2G | 2G | 0 | 0 | 0 | 0 | 0 | 9H | 9H | 0 | 0 |
| GIANT FOXTAIL | 0 | 0 | 0 | 0 | 9H | 0 | 0 | 0 | 0 | 0 | 0 | 0 | 2C,8G | 8G | 2C,2G | 0 |
| BARLEY | 0 | 0 | 0 | 0 | 7G | 0 | 0 | 0 | 0 | 0 | 0 | 0 | | | | |

| RATE = KG/HA | CMPD 9 | | CMPD 10 | | CMPD 11 | | CMPD 12 | | CMPD 13 | | CMPD 14 | | CMPD 15 | | CMPD 16 | |
|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSOL | | | | | | | | | | | | | | | | |
| COTTON | 9C | 9C | 4C,9G | 4C,9G | 3C,9G | 3C,8H | 9C | 9C | 3C,7H | 7H | 9C | 3C,8G | 4C,9G | 4C,9G | 2C,7G | 3G |
| MORNING GLORY | 10C | 5C,9H | 9C | 3C,9G | 9C | 3C,8H | 10C | 10C | 3C,7G | 3C,3G | 10C | 5C,9G | 3C,7G | 3C,7G | 4C,8G | 3C,7H |
| COCKLEBUR | 10C | 9C | 9C | 3C,8H | 10C | 3C,8H | 9C | 2C,6G | 10C | 1C,1H | 10C | 3C,9G | 4C,9G | 4C,9G | 10C | 2C,5G |
| NUTSEDGE | — | — | 10C | 2G | 10C | 0 | 10C | 3C,8G | 2G | 0 | 9C | 3C,9G | 3C,9G | 3C,9G | 5G | 0 |
| CRABGRASS | 3C,9G | 6G | 9C | 5G | 3C,8G | 2H | 6C,9G | 3C,8H | 3C,6G | 3C,6H | 3C,6G | 3G | 6G | 3G | 5G | 0 |
| BARNYARD GRASS | 9C | 9C | 9C | 3C,9H | 9C | 3C,7H | 4C,9H | 3C,2G | 5C,9G | 5C,9G | 4C,9G | 8H | 9H | 3C,8H | 3G | 0 |
| WILD OATS | 3C,9G | 9G | 5C,9G | 4C,9G | 4C,9G | 8G | 6G | 3C,7G | 2C,8G | 3C,7G | 3C,8G | 0 | 3C,9H | 0 | 0 | 0 |
| WHEAT | 5C,9G | 9G | 5C,9G | 4C,9G | 5C,9G | 7G | 7G | 2C,5G | 9G | 5C,9G | 6G | 3C,8H | 3C,6G | 3C,8H | 2G | 0 |
| CORN | 3U,9G | 9G | 9C | 9C | 9C | 5C,9G | 9H | 2C,5G | 9C | 9C | 4U,9G | 5C,9G | 3C,9G | 5C,9G | 2G | 2C,8G |
| SOYBEAN | 9C | 9C | 4C,9G | 5C,9G | 9C | 5C,9G | 4C,9G | 3C,7H | 5C,9G | 3C,9H | 9C | | 5C,9G | 5C,9G | 2C,8G | 2H |

TABLE A-continued

| | CMPD 17 | | CMPD 18 | | CMPD 19 | | CMPD 20 | | CMPD 21 | | CMPD 22 | | CMPD 23 | | CMPD 24 | |
|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| RICE | 9C | 5C,9G | 9C | 9C | 6C,9G | 5C,7G | 4C,9G | 7G | 5C,9G | 9C | 5G | 2C,8G | 6G | 3G | 2G |
| SORGHUM | 3C,9H | 9G | 9C | 4C,9G | 5C,9G | 2C,9G | 5C,9G | 4C,9H | 9G | 3C,7G | 2C,2H | 3C,9H | 2C | 2C,2G | 2G |
| CHEATGRASS | 9C | 9C | — | — | — | — | 9G | 3G | — | 9C | 3G | 3C,9G | 3G | 3G | 0 |
| SUGAR BEETS | 9C | 5C,9H | 9C | 9C | 5C,9H | 3C,7H | 9C | 5C,9G | 3H | 9C | 9C | 9C | 5C,9G | 5C,9G | 4C,9G |
| VELVETLEAF | 10C | 10C | 4C,9G | 2C,7G | 5C,9H | 3C,5H | 9C | 7G | 3G | 3C,8G | 3C,8G | 10C | 6G | 2G | 0 |
| GIANT FOXTAIL | 5C,9G | 3C,9G | 5G | 0 | 9C | 0 | 2C,3G | 0 | 2C,3G | 3C,7G | 0 | 4G | 0 | 0 | 0 |
| BARLEY | 3C,8G | 2C,8G | 4C,8G | 9C | 5C,9G | 8G | 5G | 3G | 3C,7G | 3C,7G | 2G | 3C,5G | 0 | 0 | — |
| DOWNY BROME | — | — | 9C | — | — | — | 5C,9G | 2C,5G | 3C,6G | — | — | — | — | — | — |
| PRSOL | | | | | | | | | | | | | | | | |
| COTTON | 9G | 8G | 8G | 0 | 2C,4G | 2G | 8G | 5G | 0 | 5G | 5G | 3C,9G | 5G | 5G | 2G |
| MORNING GLORY | 3C,9H | 8G | 9G | 8G | 7G | 6H | 9G | 8H | 0 | 8G | 8G | 9G | 6G | 3C,4G | 5G |
| COCKLEBUR | — | 2C,5H | 3C,8H | 2G | 2C,2H | 2G | 7G | 5G | 0 | — | — | 9H | 3C,3H | 3C,4G | 2G |
| NUTSEDGE | 10E | 10E | 8G | 5G | 5G | 0 | 9G | 5G | 0 | 10E | 7G | 10E | 0 | 8G | 0 |
| CRABGRASS | 9H | 3C,8G | 3C,8G | 3C,7G | 3C,7G | 2G | 3C,8G | 2C,6G | 2G | 9G | 6G | 5G | 7G | 3C,3G | 0 |
| BARNYARD GRASS | 9H | 9H | 3C,7G | 4C,8G | 9H | 3G | 9H | 2G | 3G | 9H | 2G | 9G | 5G | 3G | 0 |
| WILD OATS | 2C,7G | 7G | 3C,9H | 4C,8G | 8H | 0 | 8G | 2G | 0 | 3C,6G | 6G | 2C,8G | 3G | 2G | 0 |
| WHEAT | 9G | 8G | 9H | 8G | 9H | 5G | 7G | 2G | 0 | 5G | 0 | 2C,8G | 0 | 0 | 0 |
| CORN | 9H | 8G | 3C,9G | 4C,9G | 9G | 2C,5G | 3C,8H | 3C,5G | 0 | 2C,9G | 3C,6G | 3C,9H | 3C,7G | 5G | 0 |
| SOYBEAN | 9H | 2C,5G | 3C,8H | 3C,6H | 3C,7H | 4H | 3C,8H | 3C,7G | 1H | 9H | 3G | 9H | 3C,7H | 2C,3H | 5G |
| RICE | 10H | 10H | 10H | 9H | 10E | 9H | 10E | 8G | 3G | 8G | 2G | 3C,8H | 4G | 7G | 0 |
| SORGHUM | 9H | 9H | 9H | 4C,9G | 3C,9H | 8G | 10H | 3C,9H | 3C,7G | 3C,7G | 4G | 3C,9H | 3C,4G | 3C,5G | 0 |
| CHEATGRASS | 9H | 8H | — | — | — | — | — | — | — | 6G | 4G | 8G | 4G | 3G | — |
| SUGAR BEETS | 9C | 8G | 9G | 9G | 3C,9G | 6G | 9G | 9G | 3H | 9G | 8G | 9G | 8G | 9G | 7G |
| VELVETLEAF | 4C,9G | 8G | 9H | 8G | 3H | 0 | 9H | 3H | 0 | 7G | 5G | 4C,9G | 3C,4G | 0 | 0 |
| GIANT FOXTAIL | 3C,9H | 4G | 2G | 2G | 0 | 0 | 3G | 3G | 3H | 9G | 5G | 4G | 4G | 0 | 0 |
| BARLEY | 8G | 7G | 8G | 3G | 8H | 5G | 3C,7G | 2C,5G | 2G | 7G | 2G | 2C,8G | 3C,5G | 0 | — |
| DOWNY BROME | — | — | 9H | 6G | 8H | 3G | 3C,7H | 7G | 0 | 3C,6G | 0 | 0 | 0 | 0 | — |
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSOL | | | | | | | | | | | | | | | | |
| COTTON | 4C,8H | 5G | 4G | 4C,9G | 2G | 2C,4G | 0 | 7G | 0 | 2G | 0 | 5G | 0 | 2G | 0 |
| MORNING GLORY | 3C,7H | 4G | 3C,7G | 5C,9G | 3C,7G | 3C,5G | 0 | 3C,6G | 0 | 3C,7G | 3G | 0 | 0 | 0 | 0 |
| COCKLEBUR | 4C,9G | 2C,3H | 3C,7G | 3C,8G | 2C,3G | 2C | 0 | 2C,5G | 0 | 0 | 0 | 2G | 0 | 0 | 0 |
| NUTSEDGE | 9G | 0 | 0 | 0 | 0 | 0 | 0 | 0 | 0 | 7G | 0 | 0 | 0 | 0 | 0 |
| CRABGRASS | 0 | 0 | 0 | 0 | 0 | 0 | 0 | 0 | 0 | 0 | 0 | 0 | 0 | 0 | 0 |
| BARNYARD GRASS | 0 | 0 | 0 | 2H | 0 | 2H | 0 | 0 | 0 | 2C,9H | 0 | 0 | 0 | 0 | 0 |
| WILD OATS | 2C | 0 | 0 | 2C,6G | 0 | 0 | 0 | 0 | 0 | 0 | 0 | 0 | 0 | 0 | 0 |
| WHEAT | 2G | 0 | 0 | 4G | 0 | 0 | 0 | 0 | 0 | 0 | 0 | 0 | 0 | 0 | 0 |
| CORN | 5G | 0 | 3G | 4C,9H | 4C,9G | 0 | 3C,8H | 3G | 0 | 3G | 0 | 3C,9G | 0 | 0 | 0 |
| SOYBEAN | 3G | 0 | 2C,6G | 5C,9G | 4G | 4C,9G | 4C,8G | 3C,6G | 2G | 3C,6G | 0 | 0 | 2G | 3C,9G | 2G |
| RICE | 4C,9G | 3C,7G | 5C,9G | 6G | 4G | 0 | 5G | 3G | 0 | 3G | 0 | 0 | 0 | 0 | 0 |
| SORGHUM | 9G | 4G | 7G | 2C | 0 | 0 | 0 | 0 | 0 | 0 | 0 | 3G | 0 | 3G | 0 |
| CHEATGRASS | 4C,9H | 0 | 0 | 5C,9G | 4C,8G | 5C,9G | 1C | 3C,6H | 3C,8G | 0 | 0 | 0 | 0 | 0 | 0 |
| SUGAR BEETS | 2C,4G | 3C,6G | 9C | 4C,8G | 0 | 0 | 0 | 2C,7G | 4G | 2C,8G | 7G | 2C,5G | 2G | 2C,3G | 0 |
| VELVETLEAF | 5C,9G | 0 | 3C,7G | 2G | 4C,8G | 0 | 1C | 0 | 0 | 2G | 0 | 2C,7G | 0 | 0 | 0 |
| GIANT FOXTAIL | 3C,7G | 0 | 2G | 0 | 0 | 0 | 0 | 0 | 0 | 0 | 0 | 0 | 0 | 0 | 0 |
| BARLEY | 0 | 0 | 0 | 0 | 0 | 0 | 2C,2G | 0 | 0 | 0 | 0 | 0 | 0 | 0 | 0 |
| PRSOL | | | | | | | | | | | | | | | | |
| COTTON | 6G | 0 | 6G | 6G | 0 | 4G | 0 | 0 | 0 | 0 | 0 | 0 | 0 | 0 | 0 |
| MORNING GLORY | 6G | 0 | 9G | 9G | 0 | 5G | 0 | 0 | 0 | 0 | 0 | 0 | 0 | 0 | 0 |
| COCKLEBUR | 2G | 0 | 0 | 0 | 8G | 0 | 0 | 0 | 0 | 0 | 0 | 0 | 0 | 0 | 0 |

TABLE A-continued

| | CMPD 25 | | CMPD 26 | | CMPD 27 | | CMPD 28 | | CMPD 29 | | CMPD 30 | | CMPD 31 | | CMPD 32 | |
|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| NUTSEDGE | 3G | 0 | 3G | 0 | 0 | 8G | 0 | 0 | 0 | 0 | 0 | 0 | 0 | 0 | 0 | 0 |
| CRABGRASS | 9G | 0 | — | 0 | 2C,3G | 0 | 3G | 0 | 0 | 0 | 0 | 0 | 0 | 0 | 0 | 0 |
| BARNYARD GRASS | 0 | 0 | 4G | 2G | 7H | 2G | 4G | 0 | 0 | 0 | 0 | 0 | 0 | 0 | 0 | 0 |
| WILD OATS | 5G | 0 | 4G | — | 2G | 0 | 2G | 0 | 0 | 0 | 0 | 0 | 0 | 0 | 0 | 0 |
| WHEAT | 6G | 0 | 7G | 0 | 7G | 0 | 0 | 0 | 0 | 0 | 0 | 0 | 0 | 0 | 0 | 0 |
| CORN | 4G | 0 | 3C,7G | 0 | 3C,8G | 0 | 4G | 0 | 0 | 0 | 0 | 0 | 0 | 0 | 0 | 0 |
| SOYBEAN | 1H | 0 | 3C,7H | 0 | 3C,8G | 0 | 3G | 0 | 0 | 0 | 0 | 0 | 0 | 0 | 0 | 0 |
| RICE | 8G | 0 | 3C,9H | 0 | 8G | 2C,5G | 0 | 0 | 0 | 0 | 0 | 0 | 0 | 0 | 0 | 0 |
| SORGHUM | 2C,5G | 0 | 3G | 0 | 3G | 0 | 0 | 0 | 0 | 0 | 0 | 0 | 0 | 0 | 0 | 0 |
| CHEATGRASS | 4G | 0 | 4G | 0 | 2G | 0 | 5G | 0 | 0 | 0 | 0 | 0 | 0 | 0 | 0 | 0 |
| SUGAR BEETS | 8G | 4G | 9G | 7G | 7G | 3G | 0 | 0 | 2G | 0 | 0 | 0 | 0 | 0 | 0 | 0 |
| VELVETLEAF | 2G | 0 | 3G | 0 | 3C,3G | 0 | 0 | 0 | 0 | 0 | 0 | 0 | 0 | 0 | 0 | 0 |
| GIANT FOXTAIL | 9G | 0 | 7G | 0 | 3G | — | 0 | 0 | 0 | 0 | 0 | 0 | 0 | 0 | 0 | 0 |
| BARLEY | 6G | 0 | 7G | 0 | 7G | 0 | 0 | 0 | 0 | 0 | 0 | 0 | 0 | 0 | 0 | 0 |
| POSOL | | | | | | | | | | | | | | | | |
| COTTON | 0 | 0 | 4C,9G | 3C,9H | 3C,9H | 3C,8H | 4C,9H | 4C,8H | 2C,8G | 0 | 5G | 4G | 5G | 1C | 2G | 0 |
| MORNING GLORY | 0 | 0 | 10C | 9C | 9C | 9C | 10C | 9C | 9C,9G | 0 | 3C,8G | 3C,5H | 3C,9H | 4C,9G | 9C | 0 |
| COCKLEBUR | 0 | 0 | 10C | 9C | 3C,8H | 3C,8H | 10C | 0 | 4C,9H | 0 | 7G | 4G | 3C,9H | 4C,8H | 9H | 0 |
| NUTSEDGE | 0 | — | — | 2G | 0 | 0 | — | 0 | 3C,8G | 0 | — | 0 | 3C,9G | 0 | — | 0 |
| CRABGRASS | 0 | 0 | 9C | 2C,5G | 3C,5H | 3C,5H | 2C,5G | 4C,9G | 4G | 0 | 3C,8G | 3G | 3G | 5C,9G | 2C,3G | 0 |
| BARNYARD GRASS | 0 | 0 | 9C | 5C,9G | 3C,9H | 9C | 10C | 9C | 9C | 0 | 2C,3G | 0 | 9C | 2C,5G | 0 | 0 |
| WILD OATS | 0 | 0 | 9G | 8G | 2C,9G | 2C,8G | 5C,9G | 5C,9G | 2C,3G | 0 | 3G | 0 | 3C,9G | 2G | 3C,9G | 0 |
| WHEAT | 0 | 0 | 9G | 3C,9G | 8G | 8G | 3C,9G | 4C,9G | 2C,7G | 0 | 2G | 0 | 6G | 2G | 0 | 0 |
| CORN | 0 | 0 | 5C,9G | 5C,9G | 9G | 3C,9H | 5C,9G | 9C | 3C,9H | 0 | 2G | 2G | 3C,9G | 2G | 2G | 0 |
| SOYBEAN | 0 | 0 | 5C,9G | 9C | 3H,6G | 1H,2G | 2H,5G | 5C,9G | 3C,9G | 0 | 6G | 3H | 5C,9G | 3C,7H | 3G | 0 |
| RICE | 0 | 0 | 9C | 9C | 3C,9G | 9C | 9C | 9C | 9C | 0 | 3C,7G | 3G | 9C | 3C,8G | 7G | 0 |
| SORGHUM | 0 | 5G | 5C,9G | 4C,9G | 3C,9G | 9H | 4C,9G | 5C,9G | 8G | 0 | 2C,3G | 5G | 5C,9G | 9G | 5G | 2C,5G |
| CHEATGRASS | — | — | 9C | 9C | 9C | 2C,7G | 9C | 3C,9G | — | 0 | 5C,8G | 2C,7G | 5C,9G | 2C,8G | 3C,5G | 2C,4H |
| SUGAR BEETS | 0 | 5G | 9C | 10C | 10C | 10C | 10C | 10C | 10C | 3G | 3G | 6G | 9C | 4C,9G | 0 | 0 |
| VELVETLEAF | 0 | 0 | 10C | 10C | 4C,8H | 3C,8H | 9C | 3C,9H | 9C | 0 | 2G,3G | 2G | 4C,9G | 4C,9G | 0 | 0 |
| GIANT FOXTAIL | 0 | 0 | 5C,9G | 4C,9G | 2G | 0 | 2C,3G | 3C,8G | 2H,7G | 0 | 2G | 0 | 4C,9G | 4C,9G | 0 | 0 |
| BARLEY | 0 | 0 | 9C | 9G | 4C,9G | 7G | 8G | 3C,5G | 3G,6G | 0 | 2G | 0 | 3C,5G | 3C,5G | 0 | 0 |
| PRSOL | | | | | | | | | | | | | | | | |
| COTTON | 0 | 0 | 9G | 2C,8G | 3C,6G | 5G | 7G | 5H | 6G | 0 | 0 | 0 | 1C | 2G | 2C | 0 |
| MORNING GLORY | 0 | 0 | 9G | 9G | 8H | 8G | 9G | 8G | 6G | 0 | 0 | 0 | 5G | 2G | 0 | 0 |
| COCKLEBUR | 0 | — | 8H | 9H | 3C,7H | 1H | 6H | — | 7H | 0 | 0 | 0 | 2H | 1H | 0 | — |
| NUTSEDGE | 0 | 0 | 10E | 10E | 0 | 0 | 5G | 0 | 5G | 0 | 0 | 0 | 3G | 0 | 0 | 0 |
| CRABGRASS | 0 | 0 | 3C,7G | 4G | 2C | 0 | 2C,4G | 3C,7G | 3C,3G | 0 | 0 | 0 | 4G | 0 | 2G | 0 |
| BARNYARD GRASS | 0 | 0 | 9H | 9H | 3C,6G | 3C,3G | 9H | 3C,7G | 9H | 0 | 0 | 0 | 5G | 2G | 2C | 0 |
| WILD OATS | 0 | 0 | 3C,7G | 7G | 3C,6G | 3C,6G | 4C,7G | 3C,7G | 4C,7G | 0 | 0 | 0 | 2C,3G | 0 | 0 | 0 |
| WHEAT | 0 | 0 | 2C,9G | 8G | 2C,9G | 7G | 4C,9G | 3C,8G | 2C,7G | 0 | 0 | 0 | 2G | 0 | 2G | 0 |
| CORN | 0 | 0 | 3C,9G | 3C,8G | 3C,9G | 3C,8G | 3C,9G | 3C,2G | 3C,7G | 0 | 0 | 0 | 3C,5G | 2C,3G | 2G | 0 |
| SOYBEAN | 0 | 0 | 9H | 5C,9H | 3C,7H | 2C,3G | 3C,8H | 9H | 3C,6G | 0 | 0 | 0 | 3C,6H | 2C,2G | 2C | 0 |
| RICE | 0 | 0 | 10H | 9H | 10H | 8H | 10E | 9H | 9H | 0 | 0 | 0 | 2C,5G | 5G | 0 | 0 |
| SORGHUM | 0 | 0 | 10H | 9H | 5C,9H | 8H | 5C,9H | 2C,7H | 3C,9H | 0 | 0 | 0 | 3C,8H | 5G | 2G | 0 |
| CHEATGRASS | 0 | 0 | 9H | 9H | 9H | 8G | 9H | 8G | 4H | 0 | 0 | 0 | 7G | 0 | 0 | 0 |
| SUGAR BEETS | 0 | 0 | 5C,9G | 5C,9G | 5C,9G | 3C,7G | 4C,9G | 2C,2H | 9G | 3G | 0 | 0 | 9C | 3H | 0 | 0 |
| VELVETLEAF | 0 | 0 | 5C,9G | 7H | 3C,6H | 1C | 8H | 8G | 5G | 0 | 0 | 0 | 7H | 2G | 0 | 0 |
| GIANT FOXTAIL | 0 | 0 | 9H | 9H | 2C | 0 | 2C,4G | 0 | 3G | 0 | 0 | 0 | 5G | 0 | 2G | 0 |

TABLE A-continued

| BARLEY | 0 | | 0 | | 3C,8G | | 9G | | 6G | | 3C,9G | | 3C,7G | | 8G | | 2G,5G | | 0 | | 5G | | 0 | | 0 | |
|---|---|---|---|---|---|---|---|---|---|---|---|---|---|---|---|---|---|---|---|---|---|---|---|---|---|---|
| | CMPD 33 | | CMPD 34 | | CMPD 35 | | CMPD 36 | | CMPD 37 | | CMPD 38 | | CMPD 39 | | CMPD 40 | | | | | | | | | | | |
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | | | | | | | | | | |
| POSOL | | | | | | | | | | | | | | | | | | | | | | | | | | |
| COTTON | 3G | 0 | 3C,4H | 0 | 9H | 0 | 4C,9H | 3C,6H | 0 | 0 | 1C | 0 | 0 | 0 | 3C,9H | 4C,9H | | | | | | | | | | |
| MORNING GLORY | 5H | 0 | 7H | 1H | 4C,8G | 2C,6G | 10C | 4C,8H | 0 | 2H | 3C,6G | 0 | 0 | 0 | 9C | 2C,7G | | | | | | | | | | |
| COCKLEBUR | 4G | 1H | 4G | 4H | 7H | 2H | 4C,9G | 3C,6H | 3H | — | 2H | 0 | 0 | 0 | 5C,9G | 3C,9G | | | | | | | | | | |
| NUTSEDGE | 0 | 0 | 3G | 0 | — | 0 | 3C,8G | 3G | 0 | 0 | 0 | 0 | 0 | 0 | 0 | 0 | | | | | | | | | | |
| CRABGRASS | 0 | 0 | 3G | 0 | 0 | 0 | 2C,5G | 3G | 0 | 0 | 0 | 0 | 0 | 0 | 6G | 0 | | | | | | | | | | |
| BARNYARD GRASS | 2C,4G | 0 | 3C,4H | 0 | 4C,8G | 3G | 9C | 5C,9G | 3G | 0 | 3C,6G | 0 | 0 | 0 | 4C,9H | 3C,4H | | | | | | | | | | |
| WILD OATS | 0 | 0 | 0 | 0 | 0 | 0 | 5C,9G | 3C,5G | 3C,5H | 0 | 0 | 0 | 0 | 0 | 4C,9G | 4C,9G | | | | | | | | | | |
| WHEAT | 0 | 0 | 0 | 0 | 0 | 0 | — | 3G | 0 | 0 | 0 | 0 | 0 | 0 | 9G | 3C,7G | | | | | | | | | | |
| CORN | 0 | 0 | 5G | 0 | 2C,5G | 0 | 3C,9H | 3G | 2C,3G | 0 | 2G | 0 | 0 | 0 | 5C,9G | 4C,9G | | | | | | | | | | |
| SOYBEAN | 2G | 0 | 1H | 0 | 3C,8G | 0 | 3C,9G | 3C,7H | 2H | 1C | 3G | 0 | 0 | 0 | 5C,9G | 5C,9G | | | | | | | | | | |
| RICE | 1C | 0 | 3C,6G | 0 | 3C,6G | 3H | 9C | 4C,9G | 6G | 0 | 0 | 0 | 0 | 0 | 9C | 9C | | | | | | | | | | |
| SORGHUM | 3C,9G | 0 | 3C,7G | 0 | 3C,8H | 0 | 5C,9G | 3C,9G | 2C,7G | 0 | 3C,9G | 0 | 0 | 0 | 3C,9G | 4C,9G | | | | | | | | | | |
| CHEATGRASS | 0 | 0 | 4G | 0 | 2C,5G | 2G | 9C | 2C,9G | 0 | 0 | 0 | 0 | 0 | 0 | — | 9C | | | | | | | | | | |
| SUGAR BEETS | 5C,9G | 0 | 9G | 0 | 3C,8H | 2G | 10C | 4C,9G | 3C,8G | 0 | 3C,8G | 0 | 0 | 0 | 10C | 3C,5G | | | | | | | | | | |
| VELVETLEAF | 3G | 0 | 8G | 0 | 8G | 2G | 10C | 3C,8H | 3G | 0 | 0 | 0 | 0 | 0 | 5C,9G | 5C,9G | | | | | | | | | | |
| GIANT FOXTAIL | 0 | 0 | 0 | 0 | 2C,3G | 0 | 3C,8G | 2C,5G | 2G | 0 | 0 | 0 | 0 | 0 | 0 | 0 | | | | | | | | | | |
| BARLEY | 0 | 0 | 0 | 0 | 0 | 0 | 2C,8G | 4G | 0 | 0 | 0 | 0 | 0 | 0 | 4C,9G | 2C,4G | | | | | | | | | | |
| PRSOL | | | | | | | | | | | | | | | | | | | | | | | | | | |
| COTTON | 0 | 0 | 0 | 0 | 0 | 0 | 3G | 0 | 0 | 0 | 2G | 0 | 0 | 0 | 3G | 6G | | | | | | | | | | |
| MORNING GLORY | 0 | 0 | 0 | 0 | 0 | 0 | 7G | 2H | 0 | 0 | 3G | 0 | 0 | 0 | 8G | 2H | | | | | | | | | | |
| COCKLEBUR | 0 | 0 | 0 | 0 | 1C | 0 | 1C | 0 | 0 | 0 | 0 | 0 | 0 | 0 | 3C,8H | 3C,8G | | | | | | | | | | |
| NUTSEDGE | 0 | 0 | 0 | 0 | 0 | 0 | 6G | 0 | 0 | 0 | 0 | 0 | 0 | 0 | 0 | 0 | | | | | | | | | | |
| CRABGRASS | 0 | 0 | 2G | 3G | 0 | 0 | 2C | 0 | 0 | 0 | 0 | 0 | 0 | 0 | 3C,8G | 2C,5G | | | | | | | | | | |
| BARNYARD GRASS | 0 | 0 | 1C | 3G | 0 | 0 | 3C,8G | 4C,9G | 2C | 0 | 0 | 0 | 0 | 0 | 9H | 3C,6G | | | | | | | | | | |
| WILD OATS | 0 | 0 | 0 | 2G | 0 | 0 | 3C,6G | 3C,8H | 0 | 0 | 0 | 0 | 0 | 0 | 3C,8G | 3C,7G | | | | | | | | | | |
| WHEAT | 0 | 0 | 2G | 0 | 0 | 0 | 7G | 3C,5G | 0 | 0 | 0 | 0 | 0 | 0 | 2C,8H | 3C,2H | | | | | | | | | | |
| CORN | 0 | 0 | 0 | 0 | 2G | 0 | 3C,5G | 3C,7H | 2C,2G | 0 | 2G | 0 | 0 | 0 | 3C,8H | 3C,8H | | | | | | | | | | |
| SOYBEAN | 0 | 0 | 2G | 0 | 0 | 0 | 3C,6G | 3G | 0 | 0 | 3G | 0 | 0 | 0 | 3C,8G | 5H | | | | | | | | | | |
| RICE | 0 | 0 | 0 | 0 | 0 | 0 | 3C,6G | 2C,2H | 0 | 0 | 2C,2G | 0 | 0 | 0 | 9H | 9G | | | | | | | | | | |
| SORGHUM | 0 | 0 | 0 | 0 | 0 | 0 | 9H | 7H | 2G | 0 | 0 | 0 | 0 | 0 | 9G | 3C,8G | | | | | | | | | | |
| CHEATGRASS | 0 | 0 | 0 | 0 | 0 | 0 | 8G | 0 | 0 | 0 | 0 | 0 | 0 | 0 | — | — | | | | | | | | | | |
| SUGAR BEETS | 5G | 0 | 8G | 0 | 0 | 0 | 6G | — | 0 | 0 | 0 | 0 | 0 | 0 | 8G | 2H | | | | | | | | | | |
| VELVETLEAF | 0 | 0 | 0 | 0 | 0 | 0 | 3H | 0 | 0 | 0 | 0 | 0 | 0 | 0 | 3C,8H | 2G | | | | | | | | | | |
| GIANT FOXTAIL | 0 | 0 | 0 | 0 | 0 | 0 | 2C,6G | 0 | 0 | 0 | 0 | 0 | 0 | 0 | 1C | 0 | | | | | | | | | | |
| BARLEY | 0 | 0 | 0 | 0 | 0 | 0 | 2C,6G | 0 | 0 | 0 | 0 | 0 | 0 | 0 | 3C,7H | 8G | | | | | | | | | | |
| DOWNY BROME | 0 | 0 | 0 | 0 | 0 | 0 | 0 | 0 | 0 | 0 | 0 | 0 | — | — | 7G | 3C,7G | | | | | | | | | | |

| | CMPD 42 | | CMPD 43 | | CMPD 44 | | CMPD 45 | | CMPD 46 | | CMPD 47 | | CMPD 48 | | CMPD 49 | |
|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSOL | | | | | | | | | | | | | | | | |
| COTTON | 4C,9G | 3C,9G | 9C | 3C,8G | 3C,8H | 3C,8H | 3C,5G | 2G | 0 | 0 | 0 | 0 | 2G | 0 | 0 | 0 |
| MORNING GLORY | 5C,9G | 2C,5G | 3C,8G | 9C | 2C,2H | 2C,2H | 8G | 0 | 0 | 0 | 3C,7H | 2C | 2C,2H | 0 | 0 | 0 |
| COCKLEBUR | 4C,9G | 5C,9G | 5G | 5C,9G | 0 | 0 | 2C,2H | 0 | 0 | 0 | 3C,3G | 0 | 1C | 0 | 0 | 0 |
| NUTSEDGE | 0 | 0 | 0 | 10C | 9C | 9C | 0 | 0 | 0 | 0 | 0 | 0 | 0 | 0 | 0 | 0 |
| CRABGRASS | 0 | — | 0 | 0 | 3C,8G | 3C,7H | 5G | 0 | 0 | 0 | 4G | 0 | 2G | 0 | 0 | 0 |
| BARNYARD GRASS | 5C,9H | 3C,6G | 3C,7H | 5C,9G | 3C,7H | 3C,7H | 3G | 0 | 0 | 0 | 8H | 5G | 2C,5G | 0 | 0 | 0 |
| WILD OATS | 5C,9G | 4C,9G | 0 | 5C,9G | 3C,8G | 3C,8G | 3C,7G | 0 | 0 | 0 | 0 | 0 | 0 | 0 | 0 | 0 |

TABLE A-continued

|  | CMPD 50 | | CMPD 51 | | CMPD 52 | | CMPD 53 | | CMPD 54 | | CMPD 55 | | CMPD 56 | | CMPD 57 | |
|---|---|---|---|---|---|---|---|---|---|---|---|---|---|---|---|---|
| RATE = KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| WHEAT | 3C,8G | 4C,9G | 3G | 0 | 5C,9G | 3C,8G | 3C,5G | 0 | 0 | 0 | 4G | 0 | 0 | 0 | 0 | 0 |
| CORN | 9C | 5C,9G | 3C,9G | 2C,6G | 4C,9G | 3C,5G | 3C,5G | 0 | 0 | 0 | 0 | 0 | 0 | 0 | 0 | 0 |
| SOYBEAN | 5C,9G | 4C,9G | 3C,7G | 6G | 4C,9G | 7G | 3C,8H | 2H | 0 | 0 | 3C,5H | 2C,2H | 0 | 0 | 0 | 0 |
| RICE | 9C | 9C | 5C,9G | 6G | 5C,9G | 2C,8G | 7G | 5G | 0 | 0 | 2C,3G | 0 | 0 | 0 | 0 | 0 |
| SORGHUM | 5C,9G | 9G | 9H | 8G | 4C,9G | 3C,7G | 3C,7G | 2C,3G | 0 | 0 | 9H | 7G | 0 | 0 | 0 | 0 |
| CHEATGRASS |  |  |  |  |  |  |  |  |  |  | 5G | 0 | 0 | 0 | 0 | 0 |
| SUGAR BEETS | 10C | 9C | 9C | 9C | 9C | 3C,8G | 5H | 0 | 0 | 0 | 0 | 0 | 0 | 0 | 0 | 0 |
| VELVETLEAF | 3C,8G | 3C,7H | 3C,7G | 3C,6G | 4C,8H | 3C,7H | 3H | 2G | 0 | 0 | 3H | 0 | 0 | 0 | 0 | 0 |
| GIANT FOXTAIL | 9C | 0 | 2G | 0 | 0 | 0 | 0 | 0 | 0 | 0 | 3G | 1C | 0 | 0 | 0 | 0 |
| BARLEY | 4C,9G | 5G | 7G | 4G | 3C,8G | 2G | 7G | 2G | 0 | 0 | 0 | 2G | 0 | 0 | 0 | 0 |
| DOWNY BROME | 9C | 9C | 4C,9G | 0 | 4C,9G | 3C,7G | 7G | 0 | 0 | 0 | 0 | 0 | — | — | — | — |
| PRSOL |  |  |  |  |  |  |  |  |  |  |  |  |  |  |  |  |
| COTTON | 6G | 3C,5G | 5G | 0 | 2G | 0 | 5C,9G | 9G | 0 | 0 | 2C,9H | 3C,5G | 3C,6H | 0 | 0 | 0 |
| MORNING GLORY | 0 | 2G | 0 | 0 | 1C,1H | 0 | 9C | 4C,9G | 0 | 0 | 5C,9G | 4C,9G | 3C,8H | 0 | 0 | 0 |
| COCKLEBUR | 1C | 2C | 1H | 0 | 0 | 0 | 9C | 0 | 0 | 0 | 5C,9G | 3C,8G | 3C,7H | 0 | 0 | 0 |
| NUTSEDGE | 0 | 4C,9G | 4C,9G | 0 | 0 | 0 | 5C,9G | 0 | 0 | 0 | 3C,5G | 0 | 0 | 0 | 0 | 0 |
| CRABGRASS | 7G | 3C,7G | 2C,5G | 0 | 5G | 0 | 3G | 0 | 0 | 0 | 3G | 0 | 0 | 0 | 0 | 0 |
| BARNYARD GRASS | 3C,5G | 0 | 3C,5G | 0 | 3C,3G | 0 | 4C,9H | 3C,7G | 0 | 0 | 9C | 5C,9H | 8H | 0 | 0 | 0 |
| WILD OATS | 3C,7G | 2C,6G | 3C,6G | 0 | 4C,8G | 2G | 4C,9G | 3C,7G | 0 | 0 | 6G | 0 | 0 | 0 | 0 | 0 |
| WHEAT | 8G | 3C,7G | 5G | 0 | 3C,7G | 3G | 4C,9G | 3C,7G | 0 | 0 | 6G | 0 | 0 | 0 | 0 | 0 |
| CORN | 1C | 3C,6H | 0 | 0 | 3C,7G | 4G | 3C,9H | 9G | 0 | 0 | 3G | 0 | 0 | 0 | 0 | 0 |
| SOYBEAN | 6G | 3C,6H | 3C,5G | 1H | 5H | 2H | 5C,9G | 3C,9G | 2H | 0 | 5C,9G | 3C,8G | 3C,7G | 0 | 0 | 0 |
| RICE | 7G | 9H | 3C,8G | 2G | 9H | 3G | 9C | 0 | 0 | 0 | 5G | 5G | 3G | 0 | 0 | 0 |
| SORGHUM | 9G | 9G | 9H | 3G | 4C,8G | 2G | 4C,9G | 3C,8H | 0 | 0 | 9G | 9G | 9G | 0 | 0 | 0 |
| SUGAR BEETS | 7H | 0 | 5G | 0 | 0 | 3G | 0 | 0 | 2H | 0 | 9G | 6G | 2C,9G | 0 | 0 | 0 |
| CHEATGRASS |  |  |  |  |  |  |  |  |  |  | 3C,8H | 3C,8H | 3C,7H | 0 | 0 | 0 |
| VELVETLEAF | 3G | 3H | 2G | 0 | 3G | 0 | 10C | 7G | 2H | 0 | 4C,9H | 3C,8H | 3C,8H | 0 | 0 | 0 |
| GIANT FOXTAIL | 3C,7G | 0 | 0 | 0 | 0 | 0 | 10C | 4C,8G | 0 | 0 | 5C,9H | 0 | 0 | 0 | 0 | 0 |
| BARLEY | 3G | 3C,7G | 7G | 0 | 7G | 0 | 4C,9G | 3G | 0 | 0 | 5G | 0 | 0 | 0 | 0 | 0 |
| DOWNY BROME | 7G | 8G | 5C,9G | 4G | 8G | 0 | 3C,9G | 5G | 0 | 0 | 5G | 0 | 0 | 0 | — | — |

POSOL

|  | CMPD 50 | | CMPD 51 | | CMPD 52 | | CMPD 53 | | CMPD 54 | | CMPD 55 | | CMPD 56 | | CMPD 57 | |
|---|---|---|---|---|---|---|---|---|---|---|---|---|---|---|---|---|
|  | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 5C,9G | 5C,9G | 4C,9G | 9H | 4C,9G | 4C,8H | 8H | 0 | 9H | 3C,9H | 4C,9G | 2C,9H | 0 | 0 | 0 | 0 |
| MORNING GLORY | 10C | 10C | 9C | 9C | 10C | 3C,7H | 3C,7G | 1H | 5C,9G | 3C,9G | 5C,9G | 4C,9G | 2C,2H | 0 | 1C,1H | 0 |
| COCKLEBUR | 10C | 2C,8G | 10C | 5C,9G | 5C,9G | 2C,3G | 3C,9H | 2G | 5C,9H | 5C,9G | 5C,9G | 5C,9G | 1H | 0 | 3C,6G | 2G |
| NUTSEDGE | 10C | 2C,8G | 0 | 8G | 9C | — | 3C,5G | 0 | 2G | 3C,7G | 10C | 9C | 0 | 0 | 0 | 0 |
| CRABGRASS | 4C,8G | 0 | 2C,6G | 0 | 9C | 3C,8H | 3G | 3C,6H | 2G | 2G | 4C,8G | 4G | 4C,8G | 0 | 6G | 0 |
| BARNYARD GRASS | 9C, | 9C | 9C | 3C,8H | 9C | 3C,8H | 5C,9G | 3G | 3C,8H | 3C,9H | 9C | 5C,9G | 9C | 3C,7H | 4C,9H | 3C,8H |
| WILD OATS | 2C,7G | 2C,3G | 3C,9G | 3C,6G | 5C,9G | 3C,7H | 3C,7G | 3G | 3C,7G | 3C,7G | 4C,9G | 4C,9G | 3C,9G | 3C,5G | 3C,8G | 4G |
| WHEAT | 7G | 7G | 9G | 2G | 5C,9G | 2C,7G | 5G | 0 | 9G | 3C,9G | 4C,9G | 3C,9G | 6G | 3G | 3C,9G | 3C,8G |
| CORN | 9G | 9G | 3C,9H | 3G | 5C,9G | 3C,9G | 0 | 0 | 3C,5H | 3C,9H | 9C | 3C,9G | 9G | 3C,3H | 3C,9H | 2C,2H |
| SOYBEAN | 5C,9G | 3C,8G | 9C | 5C,9G | 5C,9G | 4C,9G | 3H | 0 | 4C,9H | 4C,9G | 5C,9G | 9C | 1H | 0 | 2H | 0 |
| RICE | 6C,9G | 9C | 9C | 4C,9G | 10C | 9C | 3C,9G | 7G | 4C,9H | 4C,9G | 9C | 5C,9G | 9C | 4C,9G | 9C | 8G |
| SORGHUM | 9G | 9G | 9G | 0 | 9C | 3C,6G | 3C,9G | 4G | 4C,9H | 3C,8G | 5C,9G | 3C,7G | 4C,9G | 3C,7G | 4C,9G | 3C,5G |
| CHEATGRASS | 2C,8G | 2C,5G | 6G | 9C | 9C | 7G | 3C,9G | 2H | 3C,7H | 3C,5G | 9C | 9C | 3C,7G | 5G | 9G | 7G |
| SUGAR BEETS | 10C | 10C | 9C | 0 | — | 10C | 7G | 3G | 4C,8H | 3C,9G | 10C | 9C | 5G | 0 | 5G | 0 |
| VELVETLEAF | 10C | 10C | 9C | 3C,8H | 9C | 3C,7H | 3C,7H | 0 | 4C,8H | 4C,9H | 4C,9H | 4C,9H | 3C,5G | 0 | 0 | 0 |
| GIANT FOXTAIL | 4C,9G | 3C,9G | 2G | 2G | 4C,9G | 3C,9G | 0 | 3G | 3C,7G | 3C,5G | 9C | 4C,8H | 3C,5G | 2G | 2G | 3C,7G |
| BARLEY | 7G | 3C,7G | 3C,5G | 4G | 9C | 9C | 2C,8G | 7G | 3C,8G | 3C,9G | 9C | 3C,9G | 3C,8G | 9G | 9G | 3C,7G |
| DOWNY BROME | — | — | — | — | — | — | — | — | — | — | — | — | — | — | — | — |

TABLE A-continued

| PRSOL | | | | | | | | | | | | |
|---|---|---|---|---|---|---|---|---|---|---|---|---|
| COTTON | 7G | 8H | 3G | 0 | 7G | 2G | 0 | 3C,3G | 2G | 3C,9H | 5G | 0 |
| MORNING GLORY | 9G | 8G | 2C,5H | 0 | 0 | 0 | 0 | 8H | 0 | 8H | 8H | 0 |
| COCKLEBUR | 3C,6H | 4G | 0 | 0 | 2C,3G | 3C,3G | 0 | 8H | 3C,3G | 9H | 3C,9H | 0 |
| NUTSEDGE | 10E | 0 | 0 | 0 | 0 | 0 | 0 | 5G | 0 | 10E | 10E | 0 |
| CRABGRASS | 5G | 0 | 3G | 0 | 2G | 2C,3G | 0 | 3C,6G | 2C,5G | 3C,8G | 3C,7G | 3G |
| BARNYARD GRASS | 9H | 3C,7G | 3C,7H | 5G | 0 | 2G | 0 | 3C,9H | 3G | 9H | 9H | 3G |
| WILD OATS | 2G | 0 | 3C,8G | 0 | 0 | 0 | 0 | 4C,7G | 0 | 3C,8G | 3G | 0 |
| WHEAT | 4G | 3G | 3G | 0 | 3G | 2G | 0 | 3C,8G | 0 | 3C,9G | 5G | 0 |
| CORN | 3C,9G | 3C,8G | 3C,9G | 3C,8G | 2C,2G | 0 | 3G | 3C,5G | 0 | 3C,9H | 3C,7G | 2C,2G |
| SOYBEAN | 4C,9G | 3C,7H | 3C,7H | 2C,3G | 3C,5G | 2G | 0 | 3C,6H | 3C,3H | 3C,8G | 3C,7G | 0 |
| RICE | 5C,9G | 2C,7G | 10H | 9G | 8G | 0 | 0 | 3C,8H | 1C | 10H | 9H | 3G |
| SORGHUM | 3C,9G | 4C,9G | 3C,9G | 3C,8G | 3C,8G | 2C,5G | 0 | 5C,9H | 3C,7G | 5C,9H | 3C,8G | 2C,3G |
| CHEATGRASS | 8G | 2G | 5G | 0 | — | — | 0 | 9G | 3C,4G | 9G | 7H | 3G |
| SUGAR BEETS | 4C,9G | 8G | 5C,9G | 3G | 0 | 0 | 0 | 9G | 7G | 9G | 9G | 2G |
| VELVETLEAF | 3C,9G | 8G | 3C,3H | 0 | 3G | 0 | 0 | 3C,8H | 0 | 3C,8H | 3C,7H | 0 |
| GIANT FOXTAIL | 8G | 6G | 1C | 0 | 2G | 3G | 0 | 9H | 7G | 9H | 3C,8G | 0 |
| BARLEY | 3C,4G | 2C,3G | 3C,7G | 2G | 2C,3G | 0 | 0 | 3C,7G | 0 | 3C,7G | 7G | 2C,4G |
| DOWNY BROME | — | — | — | — | 3G | 0 | 0 | — | 2C,4G | — | — | — |

| | CMPD 58 | | CMPD 59 | | CMPD 60 | |
|---|---|---|---|---|---|---|
| RATE = KG/HA | 0.05 | 0.01 | 0.05 | 0.01 | 0.05 | 0.01 |
| POSOL | | | | | | |
| COTTON | 4C,9H | 3C,6G | 9C | 5C,9G | 9C | 4C,9H |
| MORNING GLORY | 3C,8H | 3C,5G | 10C | 10C | 10C | 10C |
| COCKLEBUR | 4C,9H | 3C,8G | 10C | 10C | 10C | 10C |
| NUTSEDGE | 7G | 0 | 5G | 5G | 5G | 5G |
| CRABGRASS | 0 | 0 | 3C,8G | 3G | 5G | 2G |
| BARNYARD GRASS | 5C,9H | 4C,9G | 5C,9H | 4C,9G | 9G | 5G |
| WILD OATS | 2G | 0 | 3C,9G | 8G | 9G | 9G |
| WHEAT | 3G | 0 | 3C,9G | 9G | 9G | 9G |
| CORN | 1C,1H | 6G | 9C | 3C,9G | 3C,9H | 3G |
| SOYBEAN | 2H | 0 | 5C,9G | 3C,8H | 5C,9G | 3C,9H |
| RICE | 5C,9G | 4C,9H | 5C,9G | 5C,9G | 9C | 9C |
| SORGHUM | 9C | 0 | 5C,9G | 9C | 9G | 8G |
| CHEATGRASS | 3C,5G | 4C,9H | 10C | 10C | 9G | 4C,9G |
| SUGAR BEETS | 4C,8H | 3C,7HH | 10C | 10C | 10C | 10C |
| VELVETLEAF | 3C,7H | 5G | — | — | 10C | 10C |
| GIANT FOXTAIL | 0 | 0 | 10C | 9C | 5C,9G | 5C,9G |
| BARLEY | 2C,5G | 0 | 3C,8G | 2C,8G | 3C,9G | 5G |
| PRSOL | | | | | | |
| COTTON | 0 | 0 | 3C,9G | 3C,8H | 7H | 5G |
| MORNING GLORY | 4H | 0 | 9G | 3C,7H | 8H | 2G |
| COCKLEBUR | — | 3C,5G | 9H | 0 | 3C,8H | 2C,2G |
| NUTSEDGE | 0 | 0 | 3C,8G | 3C,7G | 3C,9G | 0 |
| CRABGRASS | 3C,5G | 2G | 6H | 0 | 7G | 2G |
| BARNYARD GRASS | 9H | 3G | 6H | 2G | 3C,7G | 2G |
| WILD OATS | 2G | 0 | 3C,8G | 2G | 3C,8G | 3C,5G |
| WHEAT | 2G | 0 | 3C,9H | 8G | 3C,9H | 7G |
| CORN | 3C,3H | 0 | 4C,8G | 3C,5H | 3C,7H | 2G |
| SOYBEAN | 0 | 0 | 10E | 10E | 9H | 2C,2H |
| RICE | 9H | 8H | | | | 3C,8H |

TABLE A-continued

| | | | | | | | |
|---|---|---|---|---|---|---|---|
| SORGHUM | 4C,9H | 8G | 5C,9H | 4C,9H | 3C,9H | 3C,8G |
| CHEATGRASS | 5G | 0 | 9H | 8H | 9H | 2C,8G |
| SUGAR BEETS | 4C,9H | 3H | 4C,9G | 9G | 7H | 7G |
| VELVETLEAF | 0 | 0 | 3C,9H | 3C,7H | 3C,8H | 2C,5G |
| GIANT FOXTAIL | 3G | 0 | 9H | 9H | 9H | 3C,8H |
| BARLEY | 5G | 0 | 9G | 7G | 3C,8G | 2C,6G |

TEST B

Seeds of weeds and crops and purple nutsedge tubers were planted in sassafras sandy loam. Test chemicals were applied preemergence or postemergence (plants 2 to 18 cm tall) then the plantings were maintained in a greenhouse 16 days before visual ratings were made for response to treatment. Ratings were based on a 0 to 100 scale where 0=no injury and 100=complete kill. These data show that some important weeds can be selectively controlled in wheat and barley.

TABLE B

| | CMPD 14 | | | | CMPD 26 | | | | CMPD 27 | | | | CMPD 28 | |
|---|---|---|---|---|---|---|---|---|---|---|---|---|---|---|
| RATE = G/HA | 0062 | 0016 | 0004 | 0001 | 0062 | 0016 | 0004 | 0001 | 0062 | 0016 | 0004 | 0001 | 0062 | 0016 |
| | | | | | POST | | | | | | | | | |
| GIANT FOXTAIL | 40 | 30 | 0 | — | 100 | 80 | 30 | 0 | 0 | 0 | 0 | 0 | 90 | 30 |
| VELVETLEAF | 100 | 100 | 60 | 30 | 100 | 100 | 90 | 60 | 90 | 80 | 70 | 50 | 70 | 50 |
| SUGAR BEETS | 100 | 100 | 100 | — | 100 | 100 | 100 | 100 | 100 | 100 | 50 | 30 | 100 | 100 |
| CRABGRASS | 70 | 0 | 0 | 0 | 100 | 70 | 60 | 30 | 70 | 50 | 30 | 0 | 60 | 30 |
| TEAWEED | 100 | 80 | 50 | 30 | 90 | 70 | 50 | 30 | 70 | 50 | 30 | 0 | 70 | 50 |
| JIMSONWEED | 100 | 90 | 70 | 40 | 100 | 90 | 60 | 30 | 100 | 90 | 70 | 30 | 100 | 90 |
| RICE | 80 | 40 | 20 | 0 | 100 | 90 | 60 | 30 | 100 | 100 | 100 | 60 | 90 | 80 |
| COCKLEBUR | 100 | 100 | 100 | 30 | 100 | 100 | 90 | 60 | 100 | 80 | 30 | 0 | 100 | 90 |
| COTTON | 100 | 80 | 0 | 0 | 70 | 60 | 50 | 30 | 60 | 30 | 0 | 0 | 70 | 40 |
| SOYBEAN | 100 | 100 | 100 | — | 100 | 100 | 100 | 70 | 100 | 50 | 0 | 0 | 70 | 50 |
| BARNYARD GRASS | 100 | 100 | 80 | 40 | 100 | 100 | 90 | 60 | 90 | 30 | 0 | 0 | 100 | 70 |
| WILD OATS | 40 | 30 | 20 | — | 90 | 60 | 30 | 0 | 90 | 60 | 30 | 0 | 90 | 70 |
| MORNINGGLORY | 100 | 80 | 30 | 0 | 100 | 100 | 80 | 60 | 100 | 80 | 30 | 0 | 100 | 90 |
| WHEAT | 30 | 20 | 0 | — | 100 | 60 | 30 | 0 | 100 | 50 | 0 | 0 | 90 | 70 |
| CASSIA | 100 | 90 | 80 | 30 | 100 | 100 | 100 | 80 | 80 | 50 | 30 | 0 | 100 | 70 |
| JOHNSONGRASS | 90 | 40 | 30 | 0 | 100 | 100 | 70 | 50 | 100 | 70 | 50 | 30 | 100 | 80 |
| NUTSEDGE | 100 | 90 | 80 | 20 | 100 | 100 | 100 | 50 | 0 | 0 | 0 | 0 | 50 | 30 |
| CORN | 100 | 90 | 70 | — | 100 | 100 | 90 | 60 | 100 | 60 | 30 | 0 | 100 | 90 |
| WILD BUCKWHEAT | 90 | 90 | 60 | — | 100 | 100 | 100 | 70 | 100 | 50 | 0 | 0 | 100 | 60 |
| BLACK GRASS | 80 | 70 | 40 | — | 100 | 100 | 90 | 60 | 100 | 70 | 50 | 30 | 90 | 70 |
| RAPESEED | 100 | 100 | 100 | — | 100 | 100 | 100 | 100 | 100 | 100 | 100 | 70 | 100 | 100 |
| BARLEY | 60 | 40 | 30 | — | 80 | 50 | 30 | 0 | 100 | 60 | 30 | 0 | 70 | 30 |
| GREEN FOXTAIL | 50 | 40 | 0 | 0 | 100 | 60 | 30 | 0 | 30 | 0 | 0 | 0 | 50 | 30 |
| CHEAT GRASS | 80 | 70 | 30 | — | 100 | 100 | 70 | 50 | 100 | 70 | 50 | 30 | 100 | 60 |
| LAMBSQUARTER | 100 | 80 | 70 | 20 | 100 | 100 | 100 | 80 | 100 | 90 | 70 | 50 | 100 | 50 |
| CHICK WEED | 100 | 100 | 80 | — | 100 | 100 | 100 | 90 | 100 | 90 | 80 | 60 | 100 | 100 |
| DOWNY BROME | | | | | | | | | | | | | | |

| | CMPD 14 | | | | CMPD 26 | | | | CMPD 27 | | | | CMPD 28 | |
|---|---|---|---|---|---|---|---|---|---|---|---|---|---|---|
| RATE = G/HA | 0062 | 0016 | 0004 | 0001 | 0062 | 0016 | 0004 | 0001 | 0250 | 0062 | 0016 | 0004 | 0250 | 0062 |
| | | | | | PRE | | | | | | | | | |
| GIANT FOXTAIL | 30 | 20 | 0 | 0 | 100 | 70 | 30 | — | 90 | 30 | 0 | — | 90 | 40 |
| VELVETLEAF | 100 | 90 | 30 | 0 | 100 | 100 | 90 | 80 | 100 | 100 | 90 | 60 | 90 | 80 |
| SUGAR BEETS | 100 | 100 | 100 | 70 | 100 | 100 | 100 | — | 100 | 100 | 70 | — | 100 | 90 |
| CRABGRASS | 80 | 70 | 50 | 20 | 100 | 70 | 30 | 0 | 70 | 30 | 0 | 0 | 90 | 60 |
| TEAWEED | 100 | 90 | 70 | 30 | 100 | 90 | 70 | 50 | 90 | 60 | 30 | 0 | 90 | 70 |
| JIMSONWEED | 100 | 100 | 50 | 30 | 100 | 90 | 50 | 30 | 100 | 90 | 60 | 30 | 90 | 80 |
| RICE | 90 | 90 | 30 | 0 | 100 | 100 | 70 | 60 | 100 | 100 | 100 | 90 | 100 | 100 |
| COCKLEBUR | 90 | 80 | 20 | 0 | 100 | 90 | 60 | 30 | 90 | 60 | 30 | 0 | 80 | 70 |
| COTTON | 0 | 0 | 0 | 0 | 80 | 70 | 50 | 30 | 60 | 50 | 30 | 0 | 70 | 30 |
| SOYBEAN | 60 | 50 | 20 | 0 | 100 | 100 | 50 | — | 80 | 50 | 0 | — | 80 | 60 |
| BARNYARD GRASS | 30 | 20 | 0 | 0 | 100 | 100 | 90 | — | 100 | 90 | 50 | — | 100 | 90 |
| WILD OATS | 60 | 40 | 30 | 20 | 90 | 60 | 30 | — | 90 | 70 | 50 | — | 70 | 50 |
| MORNINGGLORY | 100 | 90 | 30 | 0 | 100 | 100 | 80 | 60 | 100 | 100 | 90 | 70 | 100 | 90 |
| WHEAT | 20 | 0 | 0 | 0 | 100 | 80 | 50 | — | 90 | 60 | 30 | — | 100 | 70 |
| CASSIA | 100 | 100 | 30 | 0 | 100 | 90 | 50 | 30 | 100 | 100 | 100 | 70 | 100 | 100 |
| JOHNSONGRASS | 80 | 70 | 40 | 30 | 100 | 100 | 80 | 50 | 100 | 90 | 70 | 60 | 90 | 70 |
| NUTSEDGE | 100 | 100 | 70 | 30 | 100 | 100 | 90 | 70 | 90 | 70 | 50 | 30 | 70 | 50 |
| CORN | 100 | 90 | 20 | 0 | 100 | 100 | 30 | — | 100 | 90 | 60 | — | 90 | 70 |
| WILD BUCKWHEAT | 100 | 90 | 90 | 60 | 100 | 100 | 90 | — | 100 | 90 | 70 | — | 90 | 80 |
| BLACK GRASS | 100 | 90 | 60 | 30 | 100 | 100 | 90 | — | 90 | 85 | 80 | — | 100 | 100 |
| RAPESEED | 100 | 100 | 100 | 60 | 100 | 100 | 90 | — | 80 | 50 | 30 | — | 100 | 90 |
| BARLEY | 60 | 30 | 0 | 0 | 90 | 80 | 70 | — | 100 | 70 | 30 | — | 90 | 70 |
| GREEN FOXTAIL | 60 | 40 | 30 | 0 | 100 | 60 | 30 | 0 | 70 | 30 | 0 | 0 | 70 | 50 |
| CHEAT GRASS | 90 | 70 | 30 | 0 | 100 | 100 | 100 | — | 100 | 100 | 90 | — | 100 | 100 |
| LAMBSQUARTER | 100 | 100 | 30 | 20 | 100 | 100 | 90 | 60 | 100 | 90 | 70 | 60 | 100 | 90 |
| CHICK WEED | 90 | 90 | 80 | 60 | 100 | 90 | 80 | — | 90 | 80 | 70 | — | 100 | 100 |
| DOWNY BROME | | | | | | | | | | | | | | |

| | CMPD 28 | | CMPD 50 | | | | CMPD 59 | | | | CMPD 61 | | | |
|---|---|---|---|---|---|---|---|---|---|---|---|---|---|---|
| RATE = G/HA | 0004 | 0001 | 0062 | 0016 | 0004 | 0001 | 0062 | 0016 | 0004 | 0001 | 0062 | 0016 | 0004 | 0001 |
| GIANT FOXTAIL | 0 | 0 | 100 | 80 | 50 | 30 | 100 | 100 | 100 | 80 | 100 | 80 | 30 | 0 |
| VELVETLEAF | 30 | 0 | 100 | 100 | 80 | 50 | 100 | 100 | 90 | 60 | 100 | 90 | 70 | 60 |
| SUGAR BEETS | 100 | 70 | 100 | 100 | 100 | 50 | 100 | 100 | 80 | 50 | 100 | 100 | 70 | 50 |
| CRABGRASS | 0 | 0 | 60 | 30 | 0 | 0 | 100 | 100 | 90 | 50 | 90 | 70 | 50 | 30 |
| TEAWEED | 30 | 0 | 90 | 60 | 30 | 0 | 90 | 80 | 70 | 50 | 80 | 60 | 30 | 0 |
| JIMSONWEED | 80 | 60 | 70 | 50 | 30 | 0 | 100 | 90 | 80 | 60 | 100 | 100 | 90 | 80 |
| RICE | 70 | 50 | 100 | 90 | 60 | 30 | 90 | 80 | 70 | 60 | 90 | 80 | 70 | 60 |
| COCKLEBUR | 70 | 30 | 100 | 80 | 30 | 0 | 100 | 100 | 100 | 90 | 100 | 100 | 90 | 50 |
| COTTON | 0 | 0 | 80 | 70 | 50 | 0 | 100 | 100 | 90 | 60 | 90 | 70 | 50 | 30 |
| SOYBEAN | 0 | 0 | 100 | 100 | 100 | 70 | 100 | 100 | 90 | 70 | 90 | 70 | 50 | 0 |

TABLE B-continued

| | | | | | | | | | | | | | |
|---|---|---|---|---|---|---|---|---|---|---|---|---|---|
| BARNYARD GRASS | 50 | 30 | 100 | 100 | 80 | 50 | 80 | 50 | 40 | 30 | 60 | 30 | 0 | 0 |
| WILD OATS | 50 | 30 | 50 | 30 | 0 | 0 | 70 | 30 | 0 | 0 | 50 | 30 | 0 | 0 |
| MORNINGGLORY | 70 | 50 | 100 | 90 | 80 | 70 | 100 | 100 | 70 | 60 | 100 | 80 | 70 | 60 |
| WHEAT | 50 | 30 | 60 | 30 | 0 | 0 | 60 | 50 | 40 | 30 | 0 | 0 | 0 | 0 |
| CASSIA | 50 | 0 | 100 | 90 | 70 | 30 | 100 | 100 | 90 | 80 | 90 | 60 | 30 | 0 |
| JOHNSONGRASS | 60 | 30 | 70 | 50 | 30 | 0 | 100 | 100 | 90 | 70 | 100 | 100 | 80 | 50 |
| NUTSEDGE | 0 | 0 | 100 | 90 | 60 | 30 | 100 | 90 | 60 | 30 | 70 | 50 | 30 | 0 |
| CORN | 60 | 30 | 100 | 100 | 100 | 70 | 100 | 100 | 80 | 40 | 0 | 0 | 0 | 0 |
| WILD BUCKWHEAT | 30 | 0 | 100 | 70 | 50 | 30 | 100 | 100 | 100 | 80 | 100 | 90 | 60 | 30 |
| BLACK GRASS | 50 | 30 | 100 | 70 | 50 | 30 | 100 | 100 | 70 | 50 | 90 | 70 | 50 | 30 |
| RAPESEED | 70 | 50 | 100 | 100 | 100 | 70 | 100 | 100 | 90 | 70 | 100 | 100 | 80 | 60 |
| BARLEY | 0 | 0 | 0 | 0 | 0 | 0 | 90 | 70 | 50 | 30 | 0 | 0 | 0 | 0 |
| GREEN FOXTAIL | 0 | 0 | 100 | 70 | 50 | 30 | 100 | 100 | 100 | 70 | 100 | 90 | 70 | 50 |
| CHEAT GRASS | 30 | 0 | 90 | 60 | 30 | 0 | | | | | | | | |
| LAMBSQUARTER | 30 | 0 | | | | | 100 | 100 | 100 | 90 | 90 | 80 | 70 | 50 |
| CHICK WEED | 100 | 70 | 90 | 70 | 50 | 30 | 100 | 100 | 90 | 70 | 100 | 90 | 70 | 60 |
| DOWNY BROME | | | | | | | 90 | 70 | 50 | 30 | 80 | 50 | 30 | 0 |
| RATE = G/HA | 0016 | 0004 | 0250 | 0062 | 0016 | 0004 | 0250 | 0062 | 0016 | 0004 | 0250 | 0062 | 0016 | |

PRE

| | | | | | | | | | | | | | |
|---|---|---|---|---|---|---|---|---|---|---|---|---|---|
| GIANT FOXTAIL | 0 | — | 100 | 90 | 70 | 50 | 100 | 100 | 100 | — | 100 | 60 | 30 |
| VELVETLEAF | 70 | 60 | 100 | 80 | 50 | 30 | 100 | 90 | 80 | 50 | 60 | 30 | 0 |
| SUGAR BEETS | 80 | — | 100 | 100 | 90 | — | 90 | 80 | 60 | — | 50 | 30 | 0 |
| CRABGRASS | 30 | 0 | 100 | 80 | 30 | 0 | 100 | 90 | 70 | 50 | 80 | 50 | 30 |
| TEAWEED | 50 | 30 | 100 | 90 | 70 | 50 | 90 | 80 | 70 | 50 | 60 | 30 | 0 |
| JIMSONWEED | 50 | 30 | 100 | 90 | 80 | 70 | 100 | 90 | 80 | 70 | 70 | 50 | 30 |
| RICE | 90 | 70 | 100 | 100 | 100 | 70 | 100 | 100 | 90 | 85 | 100 | 100 | 100 |
| COCKLEBUR | 50 | 30 | 90 | 70 | 50 | 30 | 90 | 80 | 70 | 50 | 80 | 30 | 0 |
| COTTON | 0 | 0 | 70 | 50 | 30 | 0 | 90 | 80 | 60 | — | 40 | 0 | 0 |
| SOYBEAN | 0 | — | 90 | 70 | 50 | 0 | 80 | 30 | 0 | — | 0 | 0 | 0 |
| BARNYARD GRASS | 60 | — | 100 | 90 | 80 | 70 | 100 | 100 | 70 | — | 60 | 30 | 0 |
| WILD OATS | 30 | — | 80 | 50 | 30 | — | 70 | 50 | 30 | — | 0 | 0 | 0 |
| MORNINGGLORY | 80 | 60 | 100 | 90 | 70 | 60 | 100 | 90 | 85 | 80 | 90 | 60 | 0 |
| WHEAT | 50 | — | 50 | 30 | 0 | — | 70 | 30 | 0 | — | 50 | 30 | 0 |
| CASSIA | 70 | 50 | 100 | 90 | 60 | 30 | 100 | 90 | 80 | 30 | 70 | 30 | 0 |
| JOHNSONGRASS | 50 | 30 | 100 | 90 | 70 | 50 | 100 | 95 | 90 | — | 100 | 100 | 90 |
| NUTSEDGE | 30 | 0 | 100 | 90 | 50 | 30 | 100 | 90 | 80 | 50 | 60 | 50 | 30 |
| CORN | 30 | — | 90 | 70 | 30 | — | 90 | 70 | 0 | — | 0 | 0 | 0 |
| WILD BUCKWHEAT | 50 | — | 90 | 80 | 70 | — | 70 | 50 | 30 | — | 0 | 0 | 0 |
| BLACK GRASS | 90 | — | 100 | 100 | 90 | — | 90 | 80 | 70 | — | 90 | 60 | 30 |
| RAPESEED | 30 | — | 100 | 90 | 80 | — | 70 | 50 | 30 | — | 100 | 30 | 0 |
| BARLEY | 50 | — | 90 | 70 | 30 | — | 0 | 0 | 0 | — | 30 | 0 | 0 |
| GREEN FOXTAIL | 30 | 0 | 100 | 90 | 70 | 50 | 100 | 100 | 100 | 80 | 100 | 70 | 30 |
| CHEAT GRASS | 80 | — | 100 | 90 | 60 | — | | | | | | | |
| LAMBSQUARTER | 80 | 50 | 100 | 100 | 90 | 80 | 100 | 100 | 90 | 70 | 90 | 70 | 50 |
| CHICK WEED | 50 | — | 100 | 90 | 80 | — | 90 | 70 | 50 | — | 0 | 0 | 0 |
| DOWNY BROME | | | | | | | 100 | 100 | 50 | — | 70 | 30 | 0 |

What is claimed is:

1. A compound having the formula I:

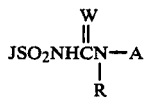

wherein J is

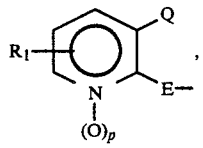 , 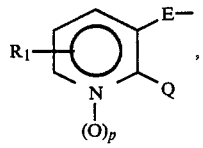 ,

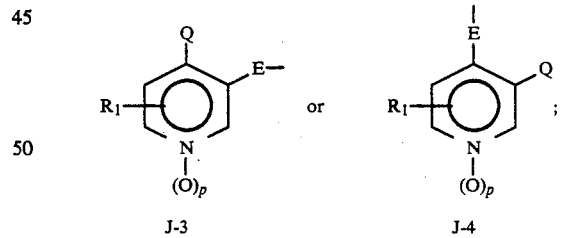

R is H or CH$_3$;
E is a single bond or CH$_2$;
W is O, S or NR$_x$;
p is 0 or 1;
R$_x$ is H, OH, C$_1$-C$_3$ alkyl, C$_1$-C$_3$ haloalkyl, C$_1$-C$_3$ alkoxy, C$_1$-C$_3$ haloalkoxy, allyloxy, propargyloxy or NR$_y$R$_z$;
R$_y$ is H or C$_1$-C$_3$ alkyl;
R$_z$ is C$_1$-C$_3$ alkyl;
R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$C$_3$ alkylsulfinyl, C$_1$-C$_3$ alkylsulfonyl, CN, CO$_2$R$_c$, C$_1$-C$_3$ haloalkoxy, C$_1$-C$_3$ haloalkylthio, amino, $C_1$-$C_2$ alkylamino, di($C_1$-$C_3$ alkyl)amino, L or C(O)NR$_d$R$_e$;

R$_a$ is H, $C_1$-$C_4$ alkyl, $C_1$-$C_3$ cyanoalkyl, methoxy or ethoxy;

R$_b$ is H, $C_1$-$C_4$ alkyl or $C_3$-$C_4$ alkenyl; or

R$_a$ and R$_b$ may be taken together as —(CH$_2$)$_3$—, —(CH$_2$)$_4$—, —(CH$_2$)$_5$— or —CH$_2$CH$_2$OCH$_2$CH$_2$—;

R$_c$ is $C_1$-$C_4$ alkyl, $C_3$-$C_4$ alkenyl, $C_3$-$C_4$ alkynyl, $C_2$-$C_4$ haloalkyl, $C_1$-$C_2$ cyanoalkyl, $C_5$-$C_6$ cycloalkyl, $C_4$-$C_7$ cycloalkylalkyl or $C_2$-$C_4$ alkoxyalkyl;

R$_d$ is H or $C_1$-$C_3$ alkyl;

R$_e$ is $C_1$-$C_3$ alkyl;

L is

L-1, L-2, L-3, L-4, L-5, L-6, L-7, L-8, L-9, L-10, L-11, L-12, L-13, L-14, L-15, L-16, L-17, L-18, L-19, L-20, L-21, L-22, L-23, L-24, L-25

Q is $C_1$-$C_4$ alkyl substituted with R$_2$;

R$_2$ is OR$_3$, S(O)$_n$R$_4$, CO$_2$R$'_4$, CONR$_5$R$_6$,

C(W$_1$R$_8$)$_2$, [cyclic structure with C, R$_7$, W$_1$, R$_9$, ($ )$_m$], C=NOR$_{10}$ with R$_7'$, SCR$_{11}$ with W$_1$,

CN, NO$_2$, $\overset{O}{\underset{\|}{P}}$R$_{14}$R$_{15}$ or $\overset{S}{\underset{\|}{P}}$R$_{14}$R$_{15}$;

R$_3$ is H, $C_1$-$C_4$ alkyl, $C_3$-$C_4$ alkenyl, $C_3$-$C_4$ alkynyl, $C_1$-$C_4$ haloalkyl, $C_3$-$C_4$ haloalkenyl, $C_3$-$C_4$ haloalkynyl, $C_2$-$C_4$ alkylcarbonyl, $C_2$-$C_4$ haloalkylcarbonyl, $C_1$-$C_4$ alkylsulfonyl, $C_2$-$C_4$ alkoxyalkyl, $C_2$-$C_4$ alkylthioalkyl or $C_2$-$C_4$ cyanoalkyl;

R$_4$ is $C_1$-$C_4$ alkyl, $C_3$-$C_4$ alkenyl, $C_3$-$C_4$ alkynyl, $C_1$-$C_4$ haloalkyl, $C_3$-$C_4$ haloalkenyl, $C_3$-$C_4$ haloalkynyl $C_2$-$C_4$ alkoxyalkyl, $C_2$-$C_4$ alkylthioalkyl or $C_2$-$C_4$ cyanoalkyl;

R$'_4$ is $C_1$-$C_4$ alkyl, $C_3$-$C_4$ alkenyl, $C_3$-$C_4$ alkynyl, $C_2$-$C_4$ haloalkyl, $C_3$-$C_4$ haloalkenyl, $C_3$-$C_4$ haloalkynyl, $C_2$-$C_4$ alkoxyalkyl, $C_2$-$C_4$ alkylthioalkyl or $C_2$-$C_4$ cyanoalkyl;

R$_5$ is H or $C_1$-$C_3$ alkyl;

R$_6$ is $C_1$-$C_4$ alkyl, $C_1$-$C_4$ haloalkyl, cyclopropyl, allyl or propargyl;

R$_5$ and R$_6$ may be taken together to form ${\text{+CH}_2\text{+}}_3$, ${\text{+CH}_2\text{+}}_4$, ${\text{+CH}_2\text{+}}_5$ or —CH$_2$CH$_2$OCH$_2$CH$_2$—;

R$_7$ is H, $C_1$-$C_4$ alkyl or $C_1$-$C_4$ haloalkyl;

R$'_7$ is H, $C_1$-$C_4$ alkyl, $C_1$-$C_4$ haloalkyl, Cl or CN;

R$_8$ is $C_1$-$C_2$ alkyl;

R$_9$ is H or CH$_3$;

R$_{10}$ is H, $C_1$-$C_4$ alkyl, $C_3$-$C_4$ alkenyl or $C_3$-$C_4$ alkynyl;

R$_{11}$ is $C_1$-$C_4$ alkyl, $C_1$-$C_4$ alkoxy, $C_1$-$C_4$ alkylthio, $C_1$-$C_4$ alkylamino or di($C_1$-$C_4$ alkyl)–amino;

W$_1$ is I or S;

n is 0, 1 or 2;

m is 1 or 2;

R$_{12}$ is H or CH$_3$;

R$_{13}$ is H or CH$_3$;

R$_{14}$ and R$_{15}$ are independently $C_1$-$C_2$ alkyl, $C_1$-$C_2$ alkoxy, $C_1$-$C_2$ alkylthio, NHCH$_3$ or N(CH$_3$)$_2$;

A is

A-1, A-6

X is H, $C_1$-$C_4$ alkyl, $C_1$-$C_4$ alkoxy, $C_2$-$C_4$ haloalkoxy, $C_1$-$C_4$ haloalkyl, $C_1$-$C_4$ haloalkylthio, $C_1$-$C_4$ alkylthio, $C_2-C_5$ alkoxyalkyl, $C_2-C_5$ alkoxyalkoxy, amino, $C_1-C_3$ alkylamino or di($C_1-C_3$ alkyl)amino;

Y is H, $C_1-C_4$ alkyl, $C_1-C_4$ alkoxy, $C_2-C_4$ haloalkoxy, $C_1-C_4$ haloalkylthio, $C_1-C_4$ alkylthio, $C_2-C_5$ alkoxyalkyl, $C_2-C_5$ alkoxyalkoxy, amino, $C_1-C_3$ alkylamino, di($C_1-C_3$ alkyl)amino, $C_3-C_4$ alkenyloxy, $C_3-C_4$ alkynyloxy, $C_2-C_5$ alkylthioalkyl, $C_2-C_5$ alkylsulfinylalkyl, $C_2-C_5$ alkylsulfonylalkyl, $C_1-C_4$ haloalkyl, $C_3-C_5$ cycloalkyl, azido, cyano,

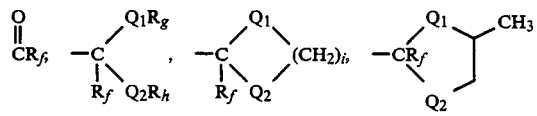

or $N(OCH_3)CH_3$;

i is 2 or 3;

$Q_1$ and $Q_2$ are independently O or S;

$R_f$ is H or $C_1-C_3$ alkyl;

$R_g$ and $R_h$ are independently $C_1-C_3$ alkyl;

Z in N;

and their agriculturally suitable salts; provided that (1) when W is S, then R is H, E is a single bond, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

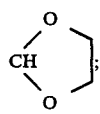

(2) when the total number of carbon atoms of X and Y is greater than four, then the combined number of carbons of $R_1$ and Q is less than or equal to six;

(3) when Y is CN then Q is other than $CH_2OCH_3$ or $CH_2OCH_2CH_3$;

(4) when J is J-1, A is A-1, $R_1$ is H, Q is $CH_2OR_3$ and both of X and Y are selected from $CH_3$, $OCH_3$ or $OCH_2CH_3$, then $R_3$ is other than $C_1-C_4$ alkyl or $C_1-C_4$ haloalkyl.

2. Compounds of claim 1 wherein

X is $C_1-C_2$ alkyl, $C_1-C_2$ alkoxy, $CH_2F$, $CF_3$, $OCH_2CH_2F$, $OCH_2CHF_2$, $OCH_2CF_3$, $CH_2Cl$ or $CH_2Br$; and Y is H, $C_1-C_2$ alkyl, $C_1-C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, $C(O)R_f$,

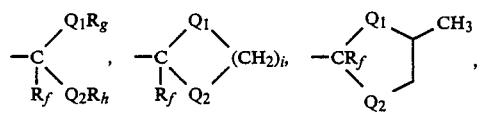

$SCF_2H$, cyclopropyl, $C\equiv CH$ or $C\equiv CCH_3$; and $R_f$ is H or $CH_3$.

3. Compounds of claim 2 wherein

E is a single bond;

W is O.

4. Compounds of claim 3 where $R_1$ is H, $CH_3$, $C_1$ haloalkyl, halogen, $NO_2$, $OCH_3$, $SO_2N(CH_3)_2$, $SCH_3$, $S(O)CH_3$, $SO_2CH_3$, , $SO_2CH_3$, $CO_2R_c$, $C_1$ haloalkoxy, $C_1$ haloalkylthio, $NH_2$, $NHCH_3$, $N(CH_3)_2$, $N(CH_3)CH_2CH_3$ or $CON(CH_3)_2$;

$R_c$ is $C_1-C_3$ alkyl, allyl, propargyl, $CH_2CH_2OCH_3$ or $CH_2CH_2Cl$;

Q is $C_1-C_2$ alkyl substituted with $R_2$;

$R_2$ is $OR_3$, $S(O)_nR_4$, $CO_2R'_4$, $CONR_5R_6$;

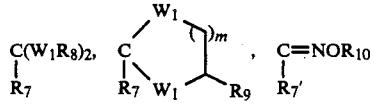

or CN;

$R_3$ is H, $C_1-C_2$ alkyl, allyl, propargyl, $C-C_2$ haloalkyl, $C_2-C_3$ alkylcarbonyl or $SO_2CH_3$;

$R_4$ is $C_1-C_2$ alkyl, allyl, propargyl, $C_1-C_2$ haloalkyl or $C_2-C_3$ alkoxycarbonyl;

$R_5$ is H or $CH_3$;

$R_6$ is $C_1-C_2$ alkyl;

$R_7$ is H or $CH_3$; and $R_{10}$ is $CH_3$ or $CH_2CH_3$.

5. Compounds of claim 4 wherein J is J-1.

6. Compounds of claim 4 wherein J is J-2.

7. Compounds of claim 4 wherein J is J-3.

8. Compounds of claim 4 wherein J is J-4.

9. Compounds of claim 5 wherein p is 0;

R is H;

A is A-1;

X is $CH_3$, $OCH_3$, $OCH_2CH_3$, or $OCH_2CF_3$; and

Y is $CH_3$, $OCH_3$, $C_2H_5$, $CH_2OCH_3$, $NHCH_3$ or $CH(OCH_3)_2$.

10. Compounds of claim 6 wherein is 0;

R is H;

A is A-1;

X is $CH_3$, $OCH_3$, $OCH_2CH_3$, or $OCH_2CF_3$; and

Y is $CH_3$, $OCH_3$, $C_2H_5$, $CH_2OCH_3$, $NHCH_3$ or $CH(OCH_3)_2$.

11. Compounds of claim 7 wherein is 0;

R is H;

A is A-1;

X is $CH_3$, $OCH_3$, $OCH_2CH_3$, or $OCH_2CF_3$; and

Y is $CH_3$, $OCH_3$, $C_2H_5$, $CH_2OCH_3$, $NHCH_3$ or $CH(OCH_3)_2$.

12. Compounds of claim 8 wherein p is 0;

R is H;

A is A-1;

X is $CH_3$, $OCH_3$, $OCH_2CH_3$, or $OCH_2CF_3$; and

Y is $CH_3$, $OCH_3$, $C_2H_5$, $CH_2OCH_3$, $NHCH_3$ or $CH(OCH_3)_2$.

13. A composition suitable for controlling the growth of undesired vegetation which comprises a herbicidally effective amount of a compound of claim 1 and a diluent, surfactant, or mixtures thereof.

14. A composition suitable for controlling the growth of undesired vegetation which comprises a herbicidally effective amount of a compound of claim 2 and a diluent, surfactant, or mixtures thereof.

15. A composition suitable for controlling the growth of undesired vegetation which comprises a herbicidally effective amount of a compound of claim 3 and a diluent, surfactant, or mixtures thereof.

16. A composition suitable for controlling the growth of undesired vegetation which comprises a herbicidally effective amount of a compound of claim 4 and a diluent, surfactant, or mixtures thereof.

17. A composition suitable for controlling the growth of undesired vegetation which comprises a herbicidally effective amount of a compound of claim 5 and a diluent, surfactant, or mixtures thereof.

18. A composition suitable for controlling the growth of undesired vegetation which comprises a herbicidally effective amount of a compound of claim 6 and a diluent, surfactant, or mixtures thereof.

19. A composition suitable for controlling the growth of undesired vegetation which comprises a herbicidally effective amount of a compound of claim 7 and a diluent, surfactant, or mixtures thereof.

20. A composition suitable for controlling the growth of undesired vegetation which comprises a herbicidally effective amount of a compound of claim 8 and a diluent, surfactant, or mixtures thereof.

21. A composition suitable for controlling the growth of undesired vegetation which comprises a herbicidally effective amount of a compound of claim 9 and a diluent, surfactant, or mixtures thereof.

22. A composition suitable for controlling the growth of undesired vegetation which comprises a herbicidally effective amount of a compound of claim 10 and a diluent, surfactant, or mixtures thereof.

23. A composition suitable for controlling the growth of undesired vegetation which comprises a herbicidally effective amount of a compound of claim 11 and a diluent, surfactant, or mixtures thereof.

24. A composition suitable for controlling the growth of undesired vegetation which comprises a herbicidally effective amount of a compound of claim 12 and a diluent, surfactant, or mixtures thereof.

25. A method for the control of undesired vegetation which comprises applying to the locus of the undesired vegetation a herbicidally effective amount of a compound of claim 1.

26. A method for the control of undesired vegetation which comprises applying to the locus of the undesired vegetation a herbicidally effective amount of a compound of claim 2.

27. A method for the control of undesired vegetation which comprises applying to the locus of the undesired vegetation a herbicidally effective amount of compound of claim 3.

28. A method for the control of undesired vegetation which comprises applying to the locus of the undesired vegetation a herbicidally effective amount of a compound of claim 4.

29. A method for the control of undesired vegetation which comprises applying to the locus of the undesired vegetation a herbicidally effective amount of a compound of claim 5.

30. A method for the control of undesired vegetation which comprises applying to the locus of the undesired vegetation a herbicidally effective amount of a compound of claim 6.

31. A method for the control of undesired vegetation which comprises applying to the locus of the undesired vegetation a herbicidally effective amount of a compound of claim 7.

32. A method for the control of undesired vegetation which comprises applying to the locus of the undesired vegetation a herbicidally effective amount of a compound of claim 8.

33. A method for the control of undesired vegetation which comprises applying to the locus of the undesired vegetation a herbicidally effective amount of a compound of claim 9.

34. A method for the control of undesired vegetation which comprises applying to the locus of the undesired vegetation a herbicidally effective amount of a compound of claim 10.

35. A method for the control of undesired vegetation which comprises applying to the locus of the undesired vegetation a herbicidally effective amount of a compound of claim 11.

36. A method for the control of undesired vegetation which comprises applying to the locus of the undesired vegetation a herbicidally effective amount of a compound of claim 12.

* * * * *

UNITED STATES PATENT AND TRADEMARK OFFICE
CERTIFICATE OF CORRECTION

PATENT NO. : 4,948,419
DATED : August 14, 1990
INVENTOR(S) : Mary A. Hanagan and Barry A. Wexler It is certified that error appears in the above—identified patent and that said Letters Patent is hereby corrected as shown below:

Claim 1, in the definition of $R_1$ change "$C_1C_3$" to -- $C_1 - C_3$ --.

Claim 1, in the definition of $R_a$ change "$C_1-C_3$ cyanoalkyl" to -- $C_2 - C_3$ cyanoalkyl --.

Claim 1, in the definition of $R_a$ and $R_b$, change " $-(CH_2)_3$ " to -- $-(CH_2)_3-$ --.

Claim 1, in the definition of $W_1$, change " 1 " to -- O --.

Claim 1, in the definition of Z, change " in " to -- is --.

Claim 1, after the definition of "Z" add the definition -- $X_3$ is $CH_3$ or $OCH_3$, --.

Claims 10 and 11, before the definition of " R " change "is 0" to --p is 0--.

Signed and Sealed this

Twelfth Day of May, 1992

Attest:

DOUGLAS B. COMER

Attesting Officer      Acting Commissioner of Patents and Trademarks